US012614635B2

(12) United States Patent
Stergiou et al.

(10) Patent No.: US 12,614,635 B2
(45) **Date of Patent: *Apr. 28, 2026**

(54) SYSTEMS AND TECHNIQUES FOR ESTIMATING THE SEVERITY OF CHRONIC OBSTRUCTIVE PULMONARY DISEASE IN A PATIENT

(71) Applicant: Board of Regents of the University Of Nebraska, Lincoln, NE (US)

(72) Inventors: Nicholas Stergiou, Bennington, NE (US); Jennifer Yentes, Omaha, NE (US); Stephen I. Rennard, Omaha, NE (US); Amol Patil, Omaha, NE (US); William Denton, Omaha, NE (US)

( * ) Notice: Subject to any disclaimer, the term of this patent is extended or adjusted under 35 U.S.C. 154(b) by 854 days.

This patent is subject to a terminal disclaimer.

(21) Appl. No.: 17/834,114

(22) Filed: Jun. 7, 2022

(65) Prior Publication Data
US 2022/0301720 A1 Sep. 22, 2022

Related U.S. Application Data

(63) Continuation of application No. 15/327,339, filed as application No. PCT/US2015/044048 on Aug. 6, 2015, now Pat. No. 11,386,998.
(Continued)

(51) Int. Cl.
*G16H 50/20* (2018.01)
*A61B 5/00* (2006.01)
(Continued)

(52) U.S. Cl.
CPC .............. *G16H 50/20* (2018.01); *A61B 5/08* (2013.01); *A61B 5/1118* (2013.01); *A61B 5/113* (2013.01);
(Continued)

(58) Field of Classification Search
CPC .......... G16H 50/20; G16H 50/30; A61B 5/08; A61B 5/1118; A61B 5/113; A61B 5/6823;
(Continued)

(56) References Cited

U.S. PATENT DOCUMENTS

| 5,730,144 | A | * | 3/1998 | Katz | .................... | A61N 1/3925 |
| | | | | | | 600/526 |
| 6,159,147 | A | * | 12/2000 | Lichter | .................. | A61B 5/308 |
| | | | | | | 600/323 |

(Continued)

FOREIGN PATENT DOCUMENTS

WO      WO 2013/0177621      12/2013

OTHER PUBLICATIONS

Webber et al. "Dynamic assessment of physiological systems and states using recurrence plot strategies". Jouranl of Applied Physiology, 76(2), 965-73, Mar. 1994.
(Continued)

*Primary Examiner* — Rene T Towa
(74) *Attorney, Agent, or Firm* — The Roy Gross Law Firm, LLC; Roy D. Gross

(57) ABSTRACT

Disclosed herein are embodiments of systems and techniques for estimating the severity of chronic obstructive pulmonary disease (COPD) in a patient. For example, in some embodiments, a system for estimating COPD severity in a patient may include logic to receive a breathing signal representative of breathing activity of the patient over a time interval, receive a locomotion signal representative of locomotive activity of the patient over the time interval, and provide breathing data and locomotion data to additional logic, wherein the additional logic is to generate an estimate of COPD severity in the patient by comparison of 1) a cross-recurrence quantification analysis (cRQA) parameter between the breathing data and the locomotion data and 2)
(Continued)

*1100*

```
RECEIVE BREATHING SIGNAL
1102
        ↓
RECEIVE LOCOMOTION SIGNAL
1104
        ↓
ADEQUATE SIGNAL CHARACTERISTICS? ──NO──→ GENERATE NOTIFICATION TO PATIENT 1108
1106
        ↓ YES
UP/DOWN CONVERSION TO BE PERFORMED? ──YES──→ PERFORM UP/DOWN CONVERSION 1112
1110
        ↓ NO
DETERMINE AN EMBEDDING DIMENSION
1114
        ↓
DETERMINE A TIME DELAY
1116
        ↓
DETERMINE A RADIUS
1118
        ↓
GENERATE CROSS-RECURRENCE DATA 1120
        ↓
GENERATE PARAMETER OF CROSS-RECURRENCE DATA 1122
        ↑
COMPARE PARAMETER TO A REFERENCE VALUE 1124
        ↑
GENERATE COPD SEVERITY ESTIMATE BASED ON COMPARISON 1126
        ↑
STORE COPD SEVERITY ESTIMATE 1128
        ↑
PROVIDE COPD SEVERITY ESTIMATE TO CARE PROVIDER COMPUTING DEVICE 1130
        ↑
PROVIDE COPD SEVERITY ESTIMATE TO PATIENT COMPUTING DEVICE 1132
``` a reference value. The breathing data may be based on the breathing signal, and the locomotion data may be based on the locomotion signal.

22 Claims, 17 Drawing Sheets

Related U.S. Application Data

(60) Provisional application No. 62/042,465, filed on Aug. 27, 2014, provisional application No. 62/034,396, filed on Aug. 7, 2014.

(51) Int. Cl.

| | |
|---|---|
| *A61B 5/08* | (2006.01) |
| *A61B 5/11* | (2006.01) |
| *A61B 5/113* | (2006.01) |
| *G16H 50/30* | (2018.01) |
| *G16Z 99/00* | (2019.01) |

(52) U.S. Cl.
CPC .......... *A61B 5/6823* (2013.01); *A61B 5/6831* (2013.01); *A61B 5/7278* (2013.01); *A61B 5/742* (2013.01); *G16H 50/30* (2018.01); *G16Z 99/00* (2019.02)

(58) Field of Classification Search
CPC ..... A61B 5/6831; A61B 5/7278; A61B 5/742; G16Z 99/00
See application file for complete search history.

(56) References Cited

U.S. PATENT DOCUMENTS

| | | | |
|---|---|---|---|
| 2006/0178591 A1 | 8/2006 | Hempfling | |
| 2007/0239220 A1* | 10/2007 | Greenhut ................. | A61B 5/29 607/32 |
| 2008/0162088 A1* | 7/2008 | DeVaul ................... | G01R 29/00 702/189 |
| 2009/0292180 A1 | 11/2009 | Mirow | |
| 2010/0083968 A1 | 4/2010 | Wondka et al. | |
| 2010/0244818 A1* | 9/2010 | Atwood ............... | G01N 37/005 324/233 |
| 2010/0275921 A1 | 11/2010 | Schindhelm et al. | |
| 2011/0021928 A1 | 1/2011 | Giovangrandi et al. | |
| 2012/0121697 A1 | 5/2012 | Rennard et al. | |
| 2012/0330114 A1 | 12/2012 | Cheung et al. | |
| 2013/0323698 A1 | 12/2013 | Gifford et al. | |
| 2014/0107501 A1 | 4/2014 | Komanduri et al. | |
| 2014/0180036 A1 | 6/2014 | Bukkapatnam et al. | |
| 2015/0096026 A1* | 4/2015 | Kolacinski ............... | G06N 7/01 726/23 |
| 2022/0301720 A1 | 9/2022 | Stergiou et al. | |

OTHER PUBLICATIONS

International Search Report and Written Opinion in PCT International Application Serial No. PCT/US2015/044048 mailed on May 12, 2016 (10 pages).

Conte, E., et al., "A brief note on possible detection of physiological singularities in respiratory dynamics by recurrence quantification analysis of lung sounds," Dec. 5, 2003, 9 pages; http://www.sciencedirect.com.

Temprado, J.J., et al., "A dynamic pattern analysis of coordination between breathing and rhythmic arm movements in humans," Neuroscience Letters, vol. 329, Sep. 6, 2002, 4 pages.

Thelen, E., et al., "A dynamic systems analysis of treadmill stepping during the first year," Monographs of the Society for Research in Child Development, vol. 56, No. 1, 1991, 108 pages.

Veiga, J., et al., "Airflow pattern complexity and airway obstruction in asthma," Journal of Applied Physiology, vol. 111, May 12, 2011, 9 pages.

Dames, K., et al., "Airflow pattern complexity during resting breathing in patients with COPD: Effect of airway obstruction," Respiratory Physiology & Neurobiology, vol. 192, 2014, 9 pages.

Gonem, S., et al., "Airway impedance entropy and exacerbations in severe asthma," European Respiratory Journal, vol. 40, No. 5, Mar. 9, 2012, 8 pages.

Fabre, N., et al., "Anaerobic threshold assessment through the ventilatory method during roller-ski skating testing: right or wrong?," Journal of Strength and Conditioning Research, vol. 26, No. 2, Feb. 2012, 7 pages.

Bernasconi, P., et al., "Analysis of co-ordination between breathing and exercise rhythms in man," Journal of Physiology, vol. 471, Nov. 1993, 14 pages.

Rassler, B., et al., "Analysis of coordination between breathing and walking rhythms in humans," Respiration Physiology, vol. 106, Dec. 1996, 12 pages.

Hramov, A., et al., "An approach to chaotic synchronization," Chaos, vol. 14, No. 3, Aug. 24, 2004, 9 pages.

Elliott, A., et al., "An examination of exercise mode on ventilatory patterns during incremental exercise," European Journal of Applied Physiology, vol. 110, Jun. 17, 2010, 7 pages.

Veiga, J., et al., "Approximate entropy as a measure of the airflow pattern complexity in asthma," 32nd Annual International Conference of the IEEE EMBS, Aug. 2010, 4 pages.

Haescher, M., et al., "A study on measuring heart- and respiration-rate via wrist-worn accelerometer-based seismocardiography (SCG) in comparison to commonly applied technologies," WOAR '15, Jun. 25, 2015, 6 pages.

Chien, J., et al., "Asynchronous Thoraco-abdominal Motion Contributes to Decreased 6-Minute Walk Test in Patients with COPD," Respiratory Care, vol. 58, No. 2, Feb. 2013, 7 pages.

Hessler, E., et al., "Attentional demands on motor-respiratory coordination," Research Quarterly for Exercise and Sport, vol. 80, No. 3, Sep. 2009, 14 pages.

Kundu, Su., et al., "A wearable capacitive sensor for monitoring human respiratory rate," Japanese Journal of Applied Physics, vol. 52, Apr. 22, 2013, 7 pages.

Zbilut, J., "Biosignatures of Health," Biological Research for Nursing, vol. 11, No. 2, Oct. 2009, 14 pages.

Guz, A., "Brain, breathing and breathlessness," Respiration Physiology, vol. 109, Jun. 17, 1997, 9 pages.

Benarroch, E., "Brainstem respiratory chemosensitivity," AAN Enterprises, Inc., Jun. 12, 2007 4 pages.

Schiermeier, S., et al., "Breathing and locomotion in patients with Parkinson's disease," European Journal of Physiology, vol. 443, Jul. 17, 2001, 5 pages.

Niizeki, K., et al., "Cardiac, respiratory, and locomotor coordination during walking in humans," Folia Primatologica, vol. 66, Issue 1-4, 1996, 16 pages.

Novak, V., et al., "Cardiolocomotor Coupling in Young and Elderly People," Journal of Gerontology: Medical Sciences, vol. 62A, No. 1., Jan. 2007, 7 pages.

Winterstein, H., "Chemical control of pulmonary ventilation," The New England Journal of Medicine, vol. 255, No. 5, Aug. 2, 1956, 8 pages.

Shockley, K., et al., "Conversation and coordinative structures," Topics in Cognitive Science, vol. 1, Apr. 2009, 15 pages.

Ebert, D., et al., "Coordination between breathing and forearm movements during sinusoidal tracking," European Journal of Applied Physiology, vol. 81, 2000, 10 pages.

Rassler, B., et al., "Coordination-related changes in the rhythms of breathing and walking in humans," European Journal of Applied Physiology, vol. 82, Jul. 2000, 9 pages.

Morin, D., et al., "Coordinations of locomotor and respiratory rhythms in vitro are critically dependent on hindlimb sensory inputs," The Journal of Neuroscience, vol. 22, No. 11, Jun. 1, 2002, 10 pages.

Castermans, T., et al., "Corticomuscular coherence revealed during treadmill walking: further evidence of supraspinal control in human locomotion," The Journal of Physiology, vol. 591, Mar. 2013, 2 pages.

(56)　　　References Cited

OTHER PUBLICATIONS

Amazeen, P., et al., "Coupling of Breathing and Movement During Manual Wheelchair Propulsion," Journal of Experimental Psychology: Human Perception and Performance, vol. 27, No. 5., Jan. 22, 2001, 17 pages.

Shockley, K., "Cross recurrence quantification of interpersonal postural activity," Tutorials in Contemporary Nonlinear Methods for the Behavioral Sciences, Chapter 4, 36 pages; http://www.nsf.gov/sbe/bcs/pac/nmbs/nmbs.jsp.

Jenner, J.R., et al., "Cutaneous reflex responses and their central nervous pathways studied in man," The Journal of Physiology, vol. 333, May 1982, 15 pages.

Garcio-Rio, F., et al., "Daily physical activity in patients with chronic obstructive pulmonary disease is mainly associated with dynamic hyperinflation," American Journal Respiratory Critical Care Medicine, vol. 180 Jun. 19, 2009, 7 pages.

Nichols, J. M., et al., "Damage detection using multivariate recurrence quantification analysis," Mechanical Systems and Signal Processing, vol. 20, Issue 2, Feb. 2006, 17 pages.

Fabre, N., et al., "Degree of coordination between breathing and rhythmic arm movements during hand rim wheelchair propulsion," International Journal Sports Medicine, vol. 27, Jan. 2006, 9 pages.

Ghosh, D., et al., "Design of coupling for synchronization in time-delayed systems," Chaos, vol. 22, Jul. 17, 2012, 9 pages.

Zbilut, J., et al., "Detecting deterministic signals in exceptionally noisy environments using cross-recurrence quantification," Physics Letters A, vol. 246, Sep. 7, 1998, 7 pages.

Williamson, M., et al., "Detection of bifurcations in noisy coupled systems from multiple time series," Chaos, Feb. 18, 2015, 13 pages, http://aip.scitation.org/doi/10.1063/1.4908603.

Loring, S., et al., "Determinants of breathing frequency during walking," Respiration Physiology, vol. 82, 1990, 11 pages.

Kennel, M., et al., "Determining embedding dimension for phasespace reconstruction using a geometrical construction," Physical Review A, The American Physical Society, vol. 45, No. 6, Mar. 15, 1992, 9 pages.

Taube, W., et al., "Direct corticospinal pathways contribute to neuromuscular control of perturbed stance," Journal of Applied Physiology, vol. 101, Apr. 6, 2006, 11 pages.

Hessler, E., et al., "Displays that facilitate performance on multifrequency ratios during motor-respiratory coordination," Acta Psychologica, vol. 133, Nov. 17, 2009, 11 pages.

Stefanucci, J., et al., "Distances appear different on hills," Perception & Psychophysics, vol. 67, Aug. 2005, 9 pages.

Maclennan, S., et al., "Does entrained breathing improve the economy of rowing?," Medicine and Science in Sports and Exercise, vol. 26, No. 5, 1994 , 5 pages.

Kito, T., et al., "Dominance of gait cycle duration in casual walking," Human Movement Science, vol. 25, Mar. 24, 2006, 10 pages; http://www.sciencedirect.com.

Daffertshofer, A., et al., "Dynamical coupling between locomotion and respiration," Biological Cybernetics, vol. 90, Mar. 3, 2004, 9 pages.

Glass, L., "Dynamical disease: Challenges for nonlinear dynamics and medicine," Chaos, Mar. 24, 2015, 12 pages; http://aip.scitation.org/doi/10.1063/1.4915529.

Schoner, G., et al., "Dynamic pattern generation in behavioral and neural systems," Science, vol. 239, No. 4847, Mar. 25, 1998, 9 pages.

Hoffmann, C., et al., "Dynamics of the locomotor-respiratory coupling at different frequencies," Springer-Verlag Berlin Heidelberg, vol. 233, Feb. 10, 2015, 11 pages.

Villard, S., et al., "Dynamic stability of locomotor respiratory coupling during cycling in humans," Neuroscience Letters, vol. 383, Aug. 5, 2005, 6 pages.

Garlando, F., et al., "Effect of coupling the breathing—and cycling rhythms on oxygen uptake during bicycle ergometry," European Journal of Applied Physiology, vol. 54, Issue 5, Sep. 27, 1985, 6 pages.

Kuznetsov, N., et al., "Effect of precision aiming on respiration and the postural-respiratory synergy," Neuroscience Letters, vol. 502, Jul. 20, 2011, 5 pages.

Sun, Y., et al., "Effects of noise on the outer synchronization of two unidirectionally coupled complex dynamical networks," Chaos, vol. 22, May 29, 2012, 11 pages.

Van Alphen, J., et al., "Entrained breathing and oxygen consumption during treadmill walking," Canadian Journal of Applied Physiology, vol. 19, No. 4, Dec. 1994, 6 pages.

Nassar, P., et al., "Entraining the natural frequencies of running and breathing in guinea fowl (Numida meleagris)," The Journal of Experimental Biology, vol. 204, Apr. 5, 2001, 11 pages.

Jasinskas, C.L., et al., "Entrainment of breathing rate to movement frequency during work at two intensities," Respiratory Physiology, vol. 42, 1980, 12 pages.

Persegol, L., et al., "Evidence for the entrainment of breathing by locomotor pattern in human," Journal of Physiology (Paris), vol. 85, 1991, 6 pages.

Petersen, N., et al., "Evidence that a transcortical pathway contributes to stretch reflexes in the tibialis anterior muscle in man," Journal of Physiology, vol. 512, Oct. 1998, 10 pages.

Peng, H., et al., "Feature selection based on mutual information: criteria of max-dependency, max-relevance, and min-redundancy," IEEE Transactions on Pattern Analysis and Machine Intelligence, vol. 27, No. 8, Aug. 2005, 13 pages.

Veiga, J., et al., "Fluctuation analysis of respiratory impedance waveform in asthmatic patients: effect of airway obstruction," Medical & Biological Engineering & Computing, vol. 50, Dec. 2012, 11 pages.

Muskulus, M., et al., "Fluctuations and determinism of respiratory impedance in asthma and chronic obstructive pulmonary disease," Journal of Applied Physiology, vol. 109, Sep. 2, 2010, 10 pages.

Turvey, M.T., et al., "Fluctuations and phase symmetry in coordinated rhythmic movements," Journal of Experimental Phychology: Human Perception and Performance, vol. 12, No. 4, Nov. 1986, 20 pages.

Pecora, L., et al., "Fundamentals of synchronization in chaotic systems, concepts, and applications," Chaos, vol. 7, No. 4, Sep. 29, 1997, 25 pages.

Seebauer, M., et al., "Gender differences in workload effect on coordination between breathing and cycling," Medicine and Science in Sports and Exercise, vol. 35, Issue 5, 2003, 6 pages.

Harris-Warrick, R., "General Principles of Rhythmogenesis in Central Pattern Generator Networks," Progress in Brain Research, vol. 187, Dec. 2010, 10 pages.

Hessler, E., et al., "Grouping feedback components by common fate benefits motor-respiratory coordination," Oct. 23, 2014, 12 pages; http://www.tandfonline.com/doi/abs/10.1080/00222895.2014.958976.

Jahn, K., et al., "Imaging human supraspinal locomotor centers in brainstem and cerebellum," NeuroImage, vol. 39, Sep. 25, 2007, 7 pages.

Seebauer, M., et al., "Influence of hypoxia on coordination between breathing and cycling rhythms in women," European Journal of Physiology, vol. 89, Jan. 15, 2003, 5 pages.

Boggs, D., "Interactions between locomotion and ventilation in tetrapods," Comparative Biochemistry and Physiology Part A, vol. 133, Apr. 21, 2002, 20 pages.

Hamill, J., et al., "Issues in quantifying variability from a dynamical systems perspective," Journal of Applied Biomechanics, vol. 16, Issue 4, Nov. 2000, 12 pages.

Houck, J., et al., "Knee and hip angle and moment adaptations during cutting tasks in subjects with anterior cruciate ligament deficiency classified as noncopers," Journal of Orthopaedic & Sports Physical Therapy, vol. 35, No. 8, Aug. 2005, 10 pages.

Hessler, E., et al., "Learning and transfer in motor-respiratory coordination," Nov. 28, 2013, 22 pages; http://www.sciencedirect.com/science/article/pii/S0167945713001589?via%3Dihub.

Banzett, R.B., et al., "Locomotion in men has No. appreciable mechanical effect on breathing," American Physiological Society, 1992, 6 pages; http://jap.physiology.org/.

(56) References Cited

OTHER PUBLICATIONS

Huys, R., et al., "Locomotion-respiration coupling: an account of the underlying dynamics," Journal of Applied Physiology, vol. 96, 2004, 3 pages.

Hurst, C., et al. "Locomotor-respiratory coupling during axillary crutch ambulation," American Journal of Physical Medicine & Rehabilitation, CME Article, 2001 Series, No. 11, Nov. 2001, 8 pages.

O'Halloran, J., et al., "Locomotor-respiratory coupling patterns and oxygen consumption during walking above and below preferred stride frequency," European Journal of Applied Physiology, vol. 112, Mar. 2012, 12 pages.

Macdonald, M., et al., "Locomotor-respiratory coupling during wheelchair propulsion," Journal of Applied Physiology, vol. 72, Apr. 1992, 5 pages.

Pride, N.B., et al., "Lung mechanics," Chronic Obstructive Pulmonary Disease, 2nd Edition, Dec. 11, 2012, 26 pages.

Bramble, D., et al., "Mammalian Locomotor-Respiratory Integration: Implications for Diaphragmatic and Pulmonary Design," Science, vol. 262, Oct. 8, 1993, 6 pages.

Chiarugi, F. et al., "Measurement of Heart Rate and Respiratory Rate Using a Textile-Based Wearable Device in Heart Failure Patients," Computers in Cardiology, vol. 35, Sep. 2008, 4 pages.

Lee, H-t., et al., "Mechanical links between locomotion and breathing: can you breathe with your legs?," News in Physiological Science, vol. 12, Dec. 1997, 7 pages; http://physiologyonline.physiology.org/content/12/6/273.full.

Macintyre, N., "Mechanisms of functional loss in patients with chronic lung disease," Repiratory Care, vol. 53, No. 9, Sep. 2008, 8 pages.

Harbourne, R., et al., "Movement variability and the use of nonlinear tools: principles to guide physical therapist practice," Journal of the American Physical Therapy Association, Jan. 23, 2009, 18 pages; http://www.ptjournal.apta.org/content/89/3/267.

Hamilton, AI., et al., "Muscle strength, symptom intensity, and exercise capacity in patients with cardiorespiratory disorders," American Journal of Respiratory Critical Care Medicine, vol. 152, Dec. 1995, 12 pages.

Hess, A., et al., "Neural mechanisms underlying breathing complexity," PLOS One, vol. 8, Issue 10, Oct. 3, 2013, 16 pages.

Fabre, N., et al., "Neuro-mechanical and chemical influences on locomotor respiratory coupling in humans," Respiratory Physiology & Neurobiology, vol. 155, Apr. 20, 2006, 11 pages; www.sciencedirect.com.

Fabre, N., et al., "No influence of hypoxia on coordination between respiratory and locomotor rhythms during rowing at moderate intensity," Journal of Sports Science and Medicine, vol. 6, Dec. 1, 2007, 6 pages.

Rathnayake, S., et al., "Nonlinear features for single-channel diagnosis of sleep-disordered breathing diseases," IEEE Transactions on Biomedical Engineering, vol. 57, No. 8, Aug. 2010, 9 pages.

Bradley, E., et al., "Nonlinear time-series analysis revisited," Chaos, Apr. 13, 2015, 11 pages; http://aip.scitation.org/doi/10.1063/1.4917289.

Von Euler, C., "On the central pattern generator for the basic breathing rhythmicity," Journal of Applied Physiology, vol. 55, No. 6, 1983, 13 pages.

Euler, C., "On the central pattern generator for the basic breathing rhythmicity," 1983, 14 pages; http://jap.physiology.org/.

Maltais, Francois et al., "Oxidative enzyme activities of the vastus lateralis muscle and the functional status in patients with COPD," Thorax, vol. 55, 2000, 7 pages; http://thorax.bmj.com/.

Allaire, J. et al., "Peripheral muscle endurance and the oxidative profile of the quadriceps in patients with COPD," Thorax, vol. 59, Apr. 18, 2004, 6 pages.

Bernard, S., et al., "Peripheral muscle weakness in patients with chronic obstructive pulmonary disease," American Journal of Respiratory and Critical Care Medicine, vol. 158, Aug. 1998, 6 pages.

Takano, N., "Phase relation and breathing pattern during locomotor/respiratory coupling in uphill and downhill running," Japanese Journal of Physiology, vol. 45, 1995, 12 pages.

Smith, J., et al., "Pre-Botzinger complex: A brainstem region that may generate respiratory rhythm in mammals," Science, vol. 254, No. 5032, Nov. 1, 1991, 5 pages, Feb. 21, 2025.

Janssens, Lo., et al., "Proprioceptive changes impair balance control in individuals with chronic obstructive pulmonary disease," PLOS One, vol. 8, Mar. 1, 2013, 6 pages.

Steinacker, J.M., et al., "Pulmonary mechanics and entrainment of respiration and stroke rate during rowing," International Journal of Sports Medicine, vol. 14, Suppl. 1, Sep. 1993, 6 pages.

Mador, M., et al., "Quadriceps fatigability after single muscle exercise in patients with chronic obstructive pulmonary disease," American Journal of Respiratory Critical Care Medicine, vol. 168, Apr. 10, 2003, 7 pages.

Peng, C.-K., et al., "Quantifying fractal dynamics of human respiration: age and gender effects," Annals of Biomedical Engineering, vol. 30, May 2002, 10 pages.

Zbilut, J., et al., "Recurrence quantification analysis: introduction and historical context," International Journal of Bifurcation and Chaos, vol. 17, No. 10, 2007, 6 pages.

Zbilut, J., et al., "Recurrence quantification analysis," Wiley Encyclopedia of Biomedical Engineering, Apr. 14, 2006, 9 pages.

Webber, C., "Recurrence quantification of fractal structures," Frontiers in Physiology, vol. 3, Article 382, Oct. 2012, 11 pages.

Webber, Jr., C., "Recurrence quantification analysis of nonlinear dynamical systems," Tutorials in Contemporary Nonlinear Methods for the Behavioral Sciences, Chapter 2, 69 pages; http://www.nsf.gov/sbe/bcs/pac/nmbs/nmbs.jsp.

Webber, Jr., C., et al., "Recurrence quantifications: feature extractions from recurrence plots," International Journal of Bifurcation and Chaos, vol. 17, No. 10, 2007, 10 pages.

Crutchfield, J., et al., "Regularities unseen, randomness observed: Levels of entropy convergence," Chaos, vol. 13, No. 1, Jan. 10, 2003, 31 pages.

Kohl, J., et al., "Relation between pedaling and breathing rhythm," European Journal of Applied Physiology and Occupational Physiology, vol. 47, Issue 3, Jun. 1, 1981, 16 pages.

Romaniuk, J., et al., "Respiratory responses to stimulation of spinal or medullary locomotor structures in decerebrate cats," Acta Neurogologiae Experimentalis, vol. 54, Feb. 20, 1994, 7 pages.

Bramble, D., et al., "Running and breathing in mammals," Science, New Series, vol. 219, No. 4582, Jan. 21, 1983, 7 pages.

Bernasconi, P., et al., "Running training and co-ordination between breathing and running rhythms during aerobic and anaerobic conditions in humans," European Journal of Applied Physiology and Occupational Physiology, 1995, 7 pages.

McDermott, W., et al., "Running training and adaptive strategies of locomotor-respiratory coordination," European Journal of Applies Physiology, vol. 89, Apr. 24, 2003, 11 pages.

Larsson, M., "Self-generated sounds of locomotion and ventilation and the evolution of human rhythmic abilities," Animal Cognition, vol. 17, Jan. 2014, 14 pages.

Tarkka, I.M., et al., "Short and long latency reflex responses elicited by electrical and mechanical stimulation in human hand muscle," Acta Physiologica Scandinavica, vol. 128, Apr. 1986, 7 pages.

Hill, A.R., et al., "Short-term entrainment of ventilation to the walking cycle in humans," Journal of Applied Physiology, vol. 65, 1988, 10 pages.

Gosker, H.R., et al., "Skeletal muscle fibre-type shifting and metabolic profile in patients with chronic obstructive pulmonary disease," European Respiratory Journal, vol. 19, 2002, 9 pages.

Casaburi, R., et al., A Statement of the American Thoracic Society and European Respiratory Society, "Skeletal muscle dysfunction in chronic obstructive pulmonary disease," American Journal of Respiratory and Critical Care Medicine, vol. 159, 1999, 40 pages.

Bello, P., et al., "Somnus: A sleep diagnostics shirt employing respiratory patters through chest expansion," Proceedings of the 2011 Design of Medical Devices Conference, Massachusetts Institute of Technology, Apr. 12-14, 2011, 5 pages.

(56) References Cited

OTHER PUBLICATIONS

Bardy, B., et al., "Sound-induced stabilization of breathing and moving," Annals of the New York Academy of Sciences, Issue: The Neurosciences and Music V, Mar. 15, 2015, 7 pages.

Hoffmann, C., et al., "Sound stabilizes locomotor-respiratory coupling and reduces energy cost," PLOS One, vol. 7, Sep. 27, 2012, 13 pages.

Gariepy, J., et al., "Specific neural substrate linking respiration to locomotion," Proceedings of the National Academy of Sciences of the United States of America, vol. 109, No. 2, Jan. 10, 2012, 12 pages.

Giraudin, A., et al., "Spinal and pontine relay pathways mediating respiratory rhythm entrainment by limb proprioceptive inputs in the neonatal rat," The Journal of Neuroscience, vol. 32 Aug. 22, 2012, 13 pages.

Eldridge, F., et al., "Stimulation by central command of locomotion, respiration and circulation during exercise," University of Nebraska Medical Center, Respiratory Physiology, vol. 59, 1985, 26 pages.

Kelso, J.A.S., et al., "Symmetry breaking dynamics of human multilimb coordination," Journal of Experimental Psychology: Human Perception and Performance, vol. 18, No. 3, 1992, 24 pages.

Hamilton, A., et al., "Symptom intensity and subjective limitation to exercise in patients with cardiorespiratory disorders," Chest, vol. 110, Nov. 1996, 9 pages.

Glass, L., "Synchronization and rhythmic processes in physiology," Nature, vol. 410, Mar. 8, 2001, 8 pages.

Pecora, L., et al., "Synchronization of chaotic systems," Chaos, Apr. 16, 2015, 13 pages; http://aip.scitation.org/doi/10.1063/1.4917383.

Wouters, E., et al., "Systemic Effects in COPD," Chest, vol. 121, Suppl., May 2002, 4 pages.

Frey, U., et al., "Temporal complexity in clinical manifestations of lung disease," Journal of Applied Physiology, vol. 110, Feb. 3, 2011, 10 pages.

Gariepy, J., et al., "The interactions between locomotion and respiration," Progress in Brain Research, vol. 187, 2010, 18 pages.

Haldane, M.D., F.R.S., J.S., et al., "The regulation of the lung-ventilation," Journal of Physiology, vol. 32, May 9, 1905, 42 pages.

Tierney, A., et al., "The ability to move to a beat is linked to the consistency of neural responses to sound," The Journal of Neuroscience, vol. 33, Sep. 18, 2013, 8 pages.

O'Donnell, D., et al., "The clinical importance of dynamic lung hyperinflation in COPD," Journal of Chronic Obstructive Pulmonary Disease, vol. 3, Dec. 2006, 15 pages.

Huys, R., et al., "The coupling between point-of-gaze and ball movements in three-ball cascade juggling: the effects of expertise, pattern and tempo," Journal of Sports Sciences, vol. 20, 2002, 17 pages.

Phillips-Silver, J., et al., "The ecology of entrainment: foundations of coordinated rhythmic movement," Music Perception, vol. 28, Sep. 2010, 18 pages.

Huang, N., et al., "The empirical mode decomposition and the Hilbert spectrum for nonlinear and non-stationary time series analysis," The Royal Society, Proceedings: Mathematical, Physical and Engineering Sciences, vol. 454, No. 1971, Mar. 8, 1998, 94 pages.

Bechbache, R. R., et al., "The Entrainment of Breathing Frequency by Exercise Rhythm," The Journal of Physiology, vol. 272, Nov. 1, 1977, 9 pages.

Paterson, D., et al., "The entrainment of ventilation frequency to exercise rhythm," The European Journal of Applied Physiology, vol. 55, 1986, 8 pages.

Petersen, T. H., et al., "The motor cortex drives the muscles during walking in human subjects," Journal of Physiology, vol. 590, May 15, 2012, 10 pages.

Krogh, A., et al., "The regulation of respiration and circulation during the initial stages of muscular work," The Journal of Physiology, vol. 47, Oct. 17, 1913, 25 pages.

Young, I., et al., "The synchronization of ventilation and locomotion in horses (*Equus caballus*)," The Journal of Experimental Biology, May 1992, 13 pages.

Blain, G., et al., "Time-frequency analysis of heart rate variability reveals cardiolocomotor coupling during dynamic cycling exercise in humans," American Journal of Physiology, vol. 296, Feb. 27, 2009, 10 pages.

Godin, P., et al., "Uncoupling of biological oscillators: A complementary hypothesis concerning the pathogenesis of multiple organ dysfunction syndrome," Critical Care Medicine, vol. 24, No. 7, Jul. 1996, 12 pages.

Pompe, B., et al., "Using mutual information to measure coupling in the cardiorespiratory system," IEEE Engineering in Medicine and Biology, Nov./Dec. 1998, 8 pages.

Bonsignore, M., et al., "Ventilation and entrainment of breathing during cycling and running in triathletes," Medicine & Science in Sports & Exercise, vol. 30, Issue 2, Feb. 1998, 8 pages.

Siegmund, G., et al., "Ventilation and locomotion coupling in varsity male rowers," Journal of Applied Physiology, vol. 87, Jul. 1999, 10 pages.

Stickford, A., et al., "Ventilation and locomotion in humans: mechanisms, implications, and perturbations to the coupling of these two rhythms," Springer Science Reviews, vol. 2, Aug. 2, 2014, 24 pages.

Mahler, D., et al., "Ventilatory responses and entrainment of breathing during rowing," Medicine and Science in Sports and Exercise, vol. 23, No. 2, Feb. 1991, 7 pages.

Huys, R., et al., "Visual perception and gaze control in judging versus producing phase relations," Human Movement Science, vol. 24, Jun. 2005, 26 pages.

Kiefer, Ad., et al., "Walking changes the dynamics of cognitive estimates of time intervals," Journal of Experimental Psychology: Human Perception and Performance, vol. 35, No. 5, 2009, 10 pages.

* cited by examiner

100

WEARABLE COMPUTING DEVICE 102

COPD ESTIMATION COMPONENT 112

PATIENT PERSONAL COMPUTING DEVICE 104

COPD ESTIMATION COMPONENT 114

DOCK COMPUTING DEVICE 106

COPD ESTIMATION COMPONENT 116

REMOTE COMPUTING DEVICE 108

COPD ESTIMATION COMPONENT 118

CARE PROVIDER COMPUTING DEVICE 110

COPD ESTIMATION COMPONENT 120

400

700

1300

| | 12:27:14 - 08:30 | 01:12:15 - 18:02 | 02:02:15 - 09:47 |
|---|---|---|---|
| DATE/TIME | | | |
| EMBEDDING DIMENSION | 5 | 6 | 5 |
| DELAY | 12 | 12 | 14 |
| RADIUS | 15.1 | 14.5 | 15.9 |
| % RECURRENCE | 2.1 | 2.3 | 2.3 |
| % DETERMINISM | 90.2 | 92.4 | 94.4 |
| ENTROPY | 9.4 | 4.3 | 4.6 |
| MAX LINE LENGTH | 129.1 | 140.2 | 145.4 |
| MEAN LINE LENGTH | 15.4 | 17.2 | 21.5 |
| FREQUENCY RATIO | 2 | 2 | 2 |
| MAX CROSS-CORRELATION | 0.24 | 0.32 | 0.35 |
| BODE INDEX | 4 | - | 4 |
| GOLD CLASS | STAGE 11 | - | - |
| EXACT SCORE | - | - | 32 |

% DETERMINISIM

1420

1430

TIME

1412

1422

PERCENT RECURRENCE

1432

TIME

1414

1424

MEAN LINE LENGTH

1434

TIME

BODE INDEX

3

05/26/14

GOLD CLASS

N/A

04/12/14

EXACT SCORE

65

04/11/14

HEART RATE

97

06/25/14

PATIENT NAME: Lorem Ipsum
DOB: 02/29/64
PULMONOLOGIST: Dolor S. Amet
ACTIVITY: Steps per day = 2242 (last measured 06/27/14)

PATIENT NOTES:
Patient has been experiencing episodes of breathlessness...

1404

1406

SYSTEMS AND TECHNIQUES FOR ESTIMATING THE SEVERITY OF CHRONIC OBSTRUCTIVE PULMONARY DISEASE IN A PATIENT

CROSS-REFERENCE TO RELATED APPLICATIONS

This application is a Continuation Application of U.S. application Ser. No. 15/327,339, Filed Jan. 18, 2017, and entitled: "Systems and techniques for estimating the severity of chronic obstructive pulmonary disease in a patient", which in turn claims priority to U.S. Provisional Application No. 62/034,396, filed on Aug. 7, 2014, entitled "SYSTEMS AND METHODS USING BIO RHYTHMS," and U.S. Provisional Application No. 62/042,465, filed Aug. 27, 2014, entitled "MONITORING SYSTEM FOR COPD", all of which are incorporated herein by reference in their entireties.

TECHNICAL FIELD

The present disclosure relates generally to the field of diagnostic systems and, more particularly, to systems and techniques for estimating the severity of chronic obstructive pulmonary disease in a patient.

BACKGROUND

Chronic obstructive pulmonary disease (COPD) is a chronic lung disease that causes obstructed airflow from the lungs. Existing techniques for classifying the severity of COPD in a patient involve lung function testing, spirometry, symptom questionnaires, body mass measurements, and exercise capacity measurements, among others.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

FIG. 13 is a representation of an illustrative data structure for storing data generated and/or used by the COPD severity estimation system of FIG. 2, in accordance with various embodiments.

DETAILED DESCRIPTION

Figure 1:
FIG. 1 is a block diagram of a computing system that may be configured for estimating the severity of chronic obstructive pulmonary disease (COPD) in a patient, in accordance with various embodiments.

Disclosed herein are embodiments of systems and techniques for estimating the severity of chronic obstructive pulmonary disease (COPD) in a patient. For example, in some embodiments, a system for estimating COPD severity in a patient may include logic to receive a breathing signal representative of breathing activity of the patient over a time interval, receive a locomotion signal representative of locomotive activity of the patient over the time interval, and provide breathing data and locomotion data to additional logic, wherein the additional logic is to generate an estimate of COPD severity in the patient by comparison of 1) a cross-recurrence quantification analysis (cRQA) parameter between the breathing data and the locomotion data and 2) a reference value. The breathing data may be based on the breathing signal, and the locomotion data may be based on the locomotion signal.

Conventional techniques for COPD severity classification may not provide a resolution sufficient to detect small and gradual worsening of a patient's condition. As a result, patients may suffer dangerous and costly exacerbations of their symptoms without warning. The magnitude of this problem is growing; COPD is the only chronic disease currently on the rise in the United States. The systems and techniques disclosed herein may provide a more accurate and timely estimate of COPD severity that may enable patients and care providers to track the progress of the disease more closely (e.g., as the disease worsens).

In the following detailed description, reference is made to the accompanying drawings that form a part hereof wherein like numerals designate like parts throughout, and in which is shown, by way of illustration, embodiments that may be practiced. It is to be understood that other embodiments may be utilized and structural or logical changes may be made without departing from the scope of the present disclosure. Therefore, the following detailed description is not to be taken in a limiting sense.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order from the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The description uses the phrases "in an embodiment" or "in embodiments," which may each refer to one or more of the same or different embodiments. Furthermore, the terms "comprising," "including," "having," and the like, as used with respect to embodiments of the present disclosure, are synonymous. As used herein, the term "logic" may refer to an Application Specific Integrated Circuit (ASIC), an electronic circuit, a processor (shared, dedicated, or group) and/or memory (shared, dedicated, or group) that execute one or more software or firmware programs, a combinational logic circuit, and/or other suitable hardware that provide the described functionality. As used herein, the term "housing" may refer to an enclosure (partial or full) for logic (e.g., a plastic or metal "box" used to at least partially contain circuitry) or another physical support for logic (e.g., a rack or a circuit board substrate).

FIG. 1 depicts an illustrative computing system 100 configured for COPD severity estimation, in accordance with various embodiments. In some embodiments, the computing system 100 may be configured to receive a breathing signal representative of breathing activity of the patient over a time interval, receive a locomotion signal representative of locomotive activity of the patient over the time interval, and provide breathing data and locomotion data to additional logic. The additional logic (which may be included in the computing system 100 or may be separate from the computing system 100, as discussed below) may be configured to generate an estimate of COPD severity in the patient by comparison of 1) a cRQA parameter between the breathing data and the locomotion data and 2) a reference value. The breathing data may be based on the breathing signal, and the locomotion data may be based on the locomotion signal.

The computing system 100 may include a wearable computing device 102, a patient personal computing device 104, a dock computing device 106, a remote computing device 108, and a care provider computing device 110. Each of the wearable computing device 102, the patient personal computing device 104, the dock computing device 106, the remote computing device 108, and the care provider computing device 110 may include COPD estimation components (illustrated in FIG. 1 as COPD estimation components 112, 114, 116, 118, and 120, respectively). COPD estimation operations may be distributed between the COPD estimation components 112, 114, 116, 118, and 120 of the computing system 100 as suitable. Several examples of the distribution of operations between the components of the computing system 100 are discussed herein, but any other combination of more or fewer components and distribution of the operations may be used. In some embodiments, the computing system 100 may be configured as a COPD severity estimation system 200, discussed below with reference to FIG. 2. One or more of the computing devices of the computing system 100 may be implemented in accordance with the embodiments discussed below with reference to the computing device 2100 of FIG. 21.

Communication within the computing system 100 may be enabled by the communication pathways illustrated in FIG. 1. The communication pathways may each include wired communication pathways and/or wireless communication pathways, over direct couplings, and/or over personal, local, and/or wide area networks. Each of the wearable computing device 102, the patient personal computing device 104, the dock computing device 106, the remote computing device 108, and the care provider computing device 110 may include suitable hardware for supporting the communication pathways, such as network interface cards, modems, Wi-Fi devices, Bluetooth devices, and so forth. In some embodiments, the communication pathways may be direct communication pathways between the components as illustrated in FIG. 1. As used herein, references to "direct" communication pathways between two components of the computing system 100 of FIG. 1 (or any system or device disclosed herein) may refer to a communication pathway that does not route through another illustrated component but that may route through other non-illustrated devices (e.g., routers and/or switches). Not all of the communication pathways illustrated in FIG. 1 may be present in every embodiment of the computing system 100. For example, in some embodiments, the wearable computing device 102 and/or the patient personal computing device 104 may not communicate directly with the care provider computing device 110 but may instead do so through an intermediate device (e.g., the dock computing device 106 and/or the remote computing device 108).

Each of the computing devices included in the computing system 100 may include a processing device and a storage device (not shown). The processing device may include one or more processing devices, such as one or more processing cores, ASICs, electronic circuits, processors (shared, dedicated, or group), combinational logic circuits, and/or other suitable components that may be configured to process electronic data. The storage device may include any suitable memory or mass storage devices (such as solid-state drive, diskette, hard drive, compact disc read only memory (CD-ROM), and so forth). Each of the computing devices included in the computing system 100 may include one or more buses (and bus bridges, if suitable) to communicatively couple the processing device, the storage device, and any other devices included in the respective computing devices. The storage device may include a set of computational logic, which may include one or more copies of computer readable media having instructions stored therein, which, when executed by the processing device of the computing device, may cause the computing device to implement any of the techniques and methods disclosed herein, or any portion thereof. The wearable computing device 102, the patient personal computing device 104, the dock computing device 106, the remote computing device 108, and the care provider computing device 110 may each include peripheral devices, which may communicate via wired or wireless communication pathways, such as cameras, printers, scanners, radio frequency identification (RFID) readers, credit card swipe devices, or any other peripheral devices. Except for the COPD severity estimation teachings of the present disclosure incorporated therein, the wearable computing device 102, the patient personal computing device 104, the dock computing device 106, the remote computing device 108, and the care provider computing device 110 may be a broad range of such devices known in the art. Specific, but not limiting, examples are described below. In some embodiments, the computational logic may include any of the logic discussed below with reference to FIG. 2.

The wearable computing device 102 may be a computing device that is integrated into a garment, accessory, or other support structure that is configured to be worn on the body of the user (or "wearer"). Examples of suitable support structures for the wearable computing device 102 may include glasses, a headset, a hair accessory (e.g., headband or barrette), an ear piece, jewelry (e.g., brooch, earrings, or necklace), a wristband (e.g., wristwatch), a neckband (e.g., tie or scarf), a garment (e.g., shirt, pants, dress skirt, or jacket), a hat, shoes, a lanyard or nametag, or an implantable support structure, among others. In some embodiments, the wearable computing device 102 may include (e.g., as a support structure) a wearable sensor for measuring physiological signals or other signals representative of the wearer's behavior. For example, as discussed below with reference to FIG. 7, a wearable computing device 102 may include a chest strap sensor that wraps around a wearer's torso and measures the expansion and contraction of the wearer's torso during breathing. In some embodiments, the wearable computing device 102 may include a wrist-mounted computing device. A wrist-mounted computing device may itself include a sensor (e.g., for measuring pulse rate and/or locomotion) and/or may be in wired or wireless communication with a sensor (e.g., a chest strap sensor). In some embodiments, the wearable computing device 102 may be a glasses-mounted computing device and may take the form of any of the embodiments discussed above with reference to the wrist-mounted computing device. COPD severity estimation and other operations performed by the wearable computing device 102 may be controlled by an app or plug-in on the wearable computing device 102, for example.

The patient personal computing device 104 may be a computing device accessible by a patient and configured for carrying in a pocket, a backpack, or other carrying case, or configured to rest semipermanently on a surface (e.g., as a server does in a rack or a desktop computer does on a desk). Examples of personal computing devices that may serve as the patient personal computing device 104 include cellular phones, smartphones, other personal mobile communication devices, tablets, electronic book readers, personal digital assistants, laptops, desktops, or other such computing devices. COPD severity estimation and other operations performed by the patient personal computing device 104 may be controlled by an app or plug-in on the patient personal computing device 104, for example. In some embodiments, the patient personal computing device 104 may have more computing resources (e.g., processing power, memory, and/or communication bandwidth) than the wearable computing device 102. Thus, in some embodiments, data captured and preliminarily processed by the wearable computing device 102 (e.g., sensor data representative of a patient's physiology or behavior) may be transmitted over a communication pathway to the patient personal computing device 104 for further processing.

The dock computing device 106 may be a computing device accessible by a patient and configured with one or more connectors to receive mating connectors of another computing device (e.g., the wearable computing device 102 or the patient personal computing device 104). In some embodiments, when another computing device is mated with the dock computing device 106, data may be transferred from the other computing device to the dock computing device 106, from the dock computing device 106 to the other computing device, or both. In some embodiments, when another computing device is mated with the dock computing device 106, the dock computing device 106 may provide power to the other computing device to charge one or more batteries or other energy storage devices of the other computing device. In some embodiments, the dock computing device 106 may have more computing resources (e.g., processing power, memory, and/or communication bandwidth), then the other computing device (e.g., a wearable computing device 102 or a patient personal computing device 104). Thus, in some embodiments, data captured and preliminarily processed by the other computing device may be transmitted over a communication pathway to the dock computing device 106 for further processing. In some embodiments, the dock computing device 106 may include a Raspberry Pi single-board computing device for performing inter-computing device communication and data transfer and storage.

In some embodiments, the dock computing device 106 may be in wired or wireless communication with the patient personal computing device 104 (e.g., a laptop or tablet), and a wearable computing device 102 may be mated with the dock computing device 106. In such an embodiment, data may be transferred from the wearable computing device 102 to the dock competing device 106, and then from the dock computing device 106 to the patient personal computing device 104. The data may remain on the patient personal computing device 104, or may be transferred by the patient personal computing device 104 to another computing device (e.g., the remote computing device 108, discussed below). Thus, in some such embodiments, the dock computing device 106 may act as an intermediary between a wearable computing device 102 and a patient personal computing device 104. Further examples of such arrangements are discussed in detail below.

In some embodiments, the dock computing device 106 may not be in wired or wireless communication with a patient personal computing device 104, but may include its own communication device for communication between the dock computing device 106 of the remote computing device (e.g., the remote computing device 108). An example communication device may be a wireless transceiver (e.g., for wireless cellular communications). In some such embodiments, when a wearable computing device 102 is mated with the dock computing device 106, data may be transferred from the wearable computing device 102 to the dock computing device 106, and the dock computing device 106 may use its own communication device to transfer the data to a remote computing device. Further examples of such arrangements are discussed in detail below.

The remote computing device 108 may include one or more servers (e.g., arranged in a "cloud" computing configuration) or other computing devices remote from the wearable computing device 102, the patient personal computing device 104, and the dock computing device 106. The communication pathway between the wearable computing device 102 and the remote computing device 108, the communication pathway between the patient personal computing device 104 and the remote computing device 108, and the communication pathway between the dock computing device 106 on the remote computing device 108 may be configured according to any remote wired or wireless communication protocol. In some embodiments, the remote computing device 108 may have more computing resources (e.g., processing power, memory, and/or communication bandwidth) than the wearable computing device 102, the patient personal computing device 104, or the dock computing device 106. Thus, in some embodiments, data captured and preliminarily processed by the wearable computing device 102, the patient personal computing device 104, and/or the dock computing device 106 (e.g., sensor data representative of a patient's physiology or behavior) may be transmitted over the appropriate communication pathways to the remote computing device 108 for further processing. In some embodiments, the remote computing device 108 may perform most of the COPD severity estimation conversational operations discussed below with reference to FIG. 2, including those performed by the estimate generation logic 228.

The care provider computing device 110 may be a computing device accessible by a care provider (e.g., doctor, nurse, care facility, or other entity that monitors a patient's health) and configured for carrying in a pocket, backpack, or other carrying case or configured to rest semipermanently on a surface (e.g., as discussed above with reference to the patient personal computing device 104). COPD severity estimation and other operations performed by the care provider personal computing device 110 may be controlled by an app or plug-in on the care provider computing device 110, for example. In some embodiments, the care provider computing device 110 may be in direct communication with the wearable computing device 102, the patient personal computing device 104, and/or the dock computing device 106, while in other embodiments, the care provider computing device 110 may be in indirect communication with one or more of the wearable computing device 102, the patient personal computing device 104, and/or the dock computing device 106 via the remote computing device 108.

In some embodiments, the remote computing device 108 may communicate with multiple personal computing devices (configured similarly to the patient personal computing device 104) corresponding to multiple different patients and/or multiple wearable computing devices (configured similarly to the wearable computing device 102) corresponding to multiple different patients. The remote computing device 108 may perform similar processing and storage operations for each personal or wearable computing device (and thus for each of the different patients). In some embodiments, a single care provider computing device 110 may be in communication with the remote computing device 108 and may access the data for the multiple patients. The remote computing device 108 may devote different resources to different ones of the plurality of personal or wearable computing devices in communication with the remote computing device 108 (e.g., different memory partitions or databases for each device).

Although a single wearable computing device 102, a single patient personal computing device 104, a single dock computing device 106, a single remote computing device 108, and a single care provider computing device 110 are illustrated in FIG. 1, this is simply for convenience, and the computing system 100 may include multiple ones of any of the computing devices. For example, in some embodiments, a patient may wear a first wearable computing device 102 on her wrist (e.g., to measure heart rate) and a second wearable computing device 102 on her chest (e.g., coupled with a chest strap sensor to measure breathing); these wearable computing devices 102 may be in communication with each other and/or with a patient personal computing device 104 or a dock computing device 106 as discussed above. A single care provider may have access to multiple care provider computing devices 110 (e.g., a desktop computer in her office and a portable tablet). The remote computing device 108 may include a first remote computing device 108 for nonvolatile storage of COPD severity estimation data and a second remote computing device 108 for processing of COPD severity estimation data. The above embodiments are simply examples, and any suitable number of various types of computing devices may be included in the computing system 100.

In some embodiments of the COPD severity estimation systems disclosed herein, one or more of the components of the computing system 100 shown in FIG. 1 may not be included. For example, in some embodiments, the computing system 100 may not include a wearable computing device 102. In some embodiments, the computing system 100 may not include a patient personal computing device 104. In some embodiments, the computing system 100 may not include a dock computing device 106. In some embodiments, the computing system 100 may not include a remote computing device 108. In some embodiments, the computing system 100 may not include a care provider computing device 110. In some embodiments, one or more of the communication pathways illustrated in FIG. 1 between components of the computing system 100 may not be included, as noted above.

Figure 2:
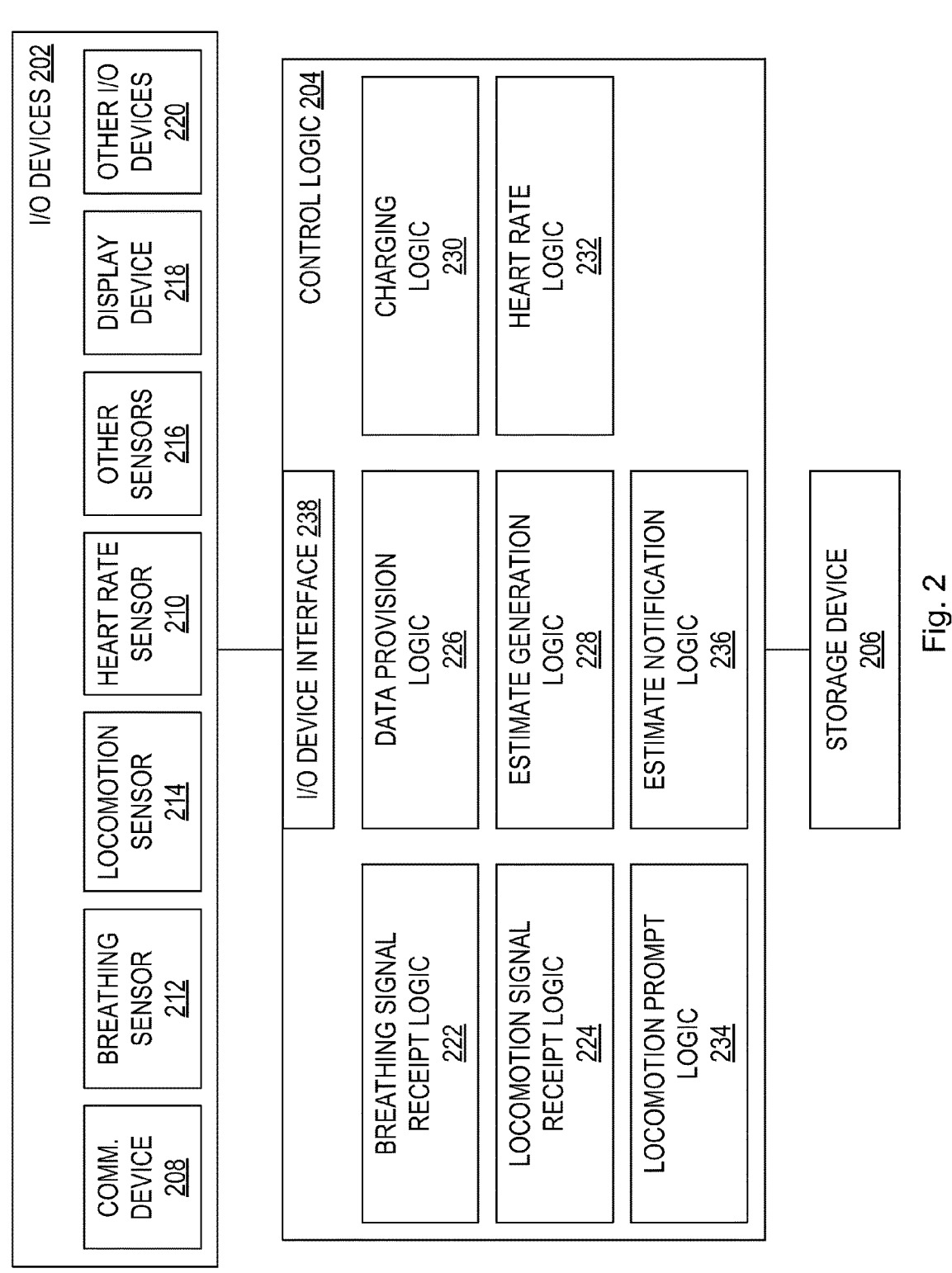
FIG. 2 is a block diagram of an illustrative COPD severity estimation system, in accordance with various embodiments.

FIG. 2 depicts an illustrative COPD severity estimation system 200. As discussed above with reference to the computing system 100, the COPD severity estimation system 200 may be configured to perform any of a number of COPD severity estimation operations. For example, the COPD severity estimation system 200 may be configured to receive a breathing signal representative of breathing activity of the patient over a time interval, receive a locomotion signal representative of locomotive activity of the patient over the time interval, and provide breathing data and locomotion data for generation of an estimate of COPD severity in the patient by comparison of 1) a cRQA parameter between the breathing data and the locomotion data and 2) a reference value. The breathing data may be based on the breathing signal, and the locomotion data may be based on the locomotion signal.

The COPD severity estimation system 200 may be implemented by the computing system 100 of FIG. 1, in accordance with various embodiments. In particular, the components of the COP severity estimation system 200 may be distributed in any suitable manner among one or more of the COPD estimation components 112, 114, 116, 118, and 120 of the computing system 100. Although a number of components are illustrated in FIG. 2, various embodiments may omit components as appropriate for the COPD severity estimation operations to be performed. For example, some embodiments of the COPD severity estimation system 200 may not be configured for heart rate data processing, and thus may not include the heart rate sensor 210 or the heart rate logic 232. In another example, some embodiments of the COPD severity estimation system 200 may not be configured for patient locomotion prompting, and thus may not include a locomotion prompt logic 234. In some embodiments, the components of the COPD severity estimation system 200 may be implemented by one or more computing devices, such as a computing device 2100 of FIG. 21 (discussed below).

The COPD severity estimation system 200 may include one or more input/output (I/O) devices 202. The one or more I/O devices 202 may include a communication device 208, a breathing sensor 212, a locomotion sensor 214, a heart rate sensor 210, other sensors 216, a display device 218, and/or other I/O devices 220. Although various ones of the I/O devices 202 (and other components described herein) may be referred to in the singular, any number of I/O devices 202 of any type may be included in the I/O devices 202 (and similarly, any component may include multiple such components). As noted above, various ones of the I/O devices 202 included in an embodiment of the COPD severity estimation system 200 may be distributed as suitable between computing devices of the computing system 100. For example, in some embodiments, a breathing sensor 212 may be included in a wearable computing device 102, while a display device 218 may be included in the care provider computing device 110. In another example, wired communication devices of the communication device 208 may be included in the wearable computing device 102 and the dock computing device 106 for wired communication therebetween, and the dock computing device 106 and the remote computing device 108 may include wireless communication devices 208 for communication therebetween.

The I/O devices 202 may include a breathing sensor 212. In some embodiments, the breathing sensor may include a chest strap sensor configured to be worn around the patient's chest. The breathing sensor may be a resistive sensor and formed of a conductive material; as the patient breathes, the expansion and contraction of the patient's chest may stretch and then release the conductive material, changing the resistance between contact points located at different locations around the circumference of the patient's chest. The changing resistance of the conductive material may be monitored by a breathing signal receipt logic 222, and may be used as the breathing signal. Alternatively, a constant current or voltage may be provided to the resistive chest strap sensor, and changes in voltage across or current through the sensor, respectively, may be used as the breathing signal. In some embodiments, a chest strap sensor may be a capacitive sensor and may have portions that act as capacitive plates separated by the patient's chest (which acts as a dielectric the value of which changes as the patient breathes). The breathing signal receipt logic 222 may apply a fixed frequency voltage signal to the capacitive plates, and the distortion of that fixed frequency voltage signal (measured as, e.g., changes in duty cycle), may provide the breathing signal.

In some embodiments, the breathing sensor 212 may measure the flow of air out of a patient's nose and/or mouth. For example, the breathing sensor 212 may include a nasal cannula. 214 may include one or more sensors able to detect locomotive activity of a patient (e.g., walking, running, or other locomotive activity). The locomotion sensor 214 may be located in any suitable computing device or computing devices of the computing system 100 (e.g., in the wearable computing device 102). In some embodiments, the locomotion sensor 214 may include a pressure sensor configured for use inside a patient's shoe or sock; as the patient takes steps, the changing pressure on the sensor may be used as the locomotion signal.

In some embodiments, the locomotion sensor 214 may include one or more accelerometers. As is well known, acceleration data generated by an accelerometer may be integrated once to provide velocity data, and twice to provide location data. Any of these types of data may be used as locomotion data, as suitable. In some embodiments, the locomotion data may include a step count, an altitude change, or any other suitable quantification of the patient's movement. An accelerometer may be a one-, two-, or three-axis accelerometer. In some embodiments, the locomotion sensor 214 may be an inertial measurement unit (IMU) that includes a gyroscope and a three-axis accelerometer. In such embodiments, some or all of the data generated by the IMU may be utilized to provide the locomotion sensor 214. For example, in some embodiments, the gyroscope data may be ignored, and data from one or more axis of the three-axis accelerometer may be used to generate the locomotion data. One or more accelerometers may be located at any suitable location or locations on the patient's body. For example, one or more accelerometers may be mounted in an eyeglasses-type support, in a bracelet-type support designed to be worn on the patient's ankle, in a bracelet-type support designed to be worn on the patient's wrist, in a garter-type support designed to be worn on the patient's thigh, in a band designed to be worn around the patient's waist or chest, or in a housing designed to clip to a patient's belt, pants, or skirt. These are simply illustrative examples, and any suitable support may be used to mount one or more accelerometers. In some embodiments, one accelerometer may be positioned at one location on a patient's body, while another accelerometer may be positioned at another location on the user's body (e.g., on the wrist and on the torso).

In some embodiments, the locomotion sensor 214 may include one or more image capture devices, such as one or more digital cameras included in the wearable computing device 102. In such embodiments, the locomotion of the patient may be determined by analysis of the images captured by the image capture device as the patient moves. This analysis may include conventional video processing techniques for determining speed of motion, direction of motion, and type of motion, for example. One or more image capture devices may be located in a suitable location or locations on the patient's body. For example, one or more image capture devices may be mounted in an eyeglasses-type support and may be "outward" facing to image the environment around the patient as the patient moves.

In some embodiments, the locomotion sensor 214 may be configured to stream locomotion data (e.g., accelerometer or video data) to other devices via a wired or wireless communication pathway. For example, the locomotion sensor 214 may be included in the wearable computing device 102, and may stream locomotion data wirelessly to the patient personal computing device 104. In other embodiments, the locomotion sensor 214 may be included in the wearable computing device 102, and the wearable computing device 102 may store the locomotion data generated by the locomotion sensor 214 in a storage device local to the wearable computing device 102 (e.g., a storage device 206). In some such embodiments, the wearable computing device 102 may provide the locomotion data to the dock computing device 106 upon mating the wearable computing device 102 with the dock computing device 106, or the wearable computing device 102 may provide the locomotion data to the patient personal computing device 104 via a wired or wireless communication pathway. In other embodiments, the wearable computing device 102 may provide the locomotion data directly to the remote computing device 108 (e.g., via a wireless communication pathway).

In some embodiments, the I/O devices 202 may include a heart rate sensor 210. The heart rate sensor 210 may be any commercially available heart rate sensor 210, such as a chest strap sensor and associated processing electronics. In some embodiments, the breathing sensor 212 and the heart rate sensor 210 may share components. For example, the breathing sensor 212 and the heart rate sensor may both utilize a chest strap substrate; the breathing sensor 212 may generate a breathing signal from the chest strap substrate by monitoring changes in resistance or capacitance, as discussed above, while the heart rate sensor 210 may generate heart rate data from the chest strap substrate by monitoring an electrocardiogram (EKG) sensed by electrodes mounted on or included in the chest strap substrate. In some embodiments, the heart rate sensor 210 may generate heart rate data by monitoring another part of the body, such as the wrist. The heart rate data generated by the heart rate sensor 210 may be a raw or processed EKG, or may be a signal expressed in beats per time unit.

In some embodiments, the I/O devices 202 may include one or more other sensors 216. In some embodiments, the other sensors 216 may include any buttons, switches, dials, or other interface devices configured to be actuated by a user (e.g., the patient or a care provider). For example, the other sensors 216 may include buttons that are pressable by a user to start receipt of a breathing or locomotion signal, reset receipt of a breathing or locomotion signal (e.g., by wiping breathing or locomotion information stored in the storage device 206), end receipt of a breathing or locomotion signal, or control any other operation of the COPD severity estimation system 200. In some embodiments, the other sensors 216 may include an altimeter, a humidity sensor, an ambient pressure sensor, and/or a temperature sensor (e.g., a micro-electromechanical systems (MEMS) sensor that may measure temperature and pressure). The data from these sensors may be used to inform the level of a patient's effort during locomotion.

In some embodiments, the I/O devices 202 may include one or more communication devices 208. The communication device 208 may enable wired and/or wireless communications for the transfer of data to, from, and/or between components of the COPD severity estimation system 200 (e.g., to, from, and/or between components of the computing system 100). The communication device 208 may include multiple communication devices, with one or more communication devices included in each component of the computing system 100. For example, the communication device 208 may support one or more wired communication protocols, such as I2C, universal serial bus (USB), SPI, or any other communication protocol.

The term "wireless" and its derivatives may be used to describe circuits, devices, systems, methods, techniques, communications channels, etc., that may communicate data through the use of modulated electromagnetic radiation through a nonsolid medium. The term does not imply that the associated devices do not contain any wires, although in some embodiments they might not. The communication device 208 may implement any of a number of wireless standards or protocols, including but not limited to Institute for Electrical and Electronic Engineers (IEEE) standards including Wi-Fi (IEEE 802.11 family), IEEE 802.16 standards (e.g., IEEE 802.16-2005 Amendment), Long-Term Evolution (LTE) project along with any amendments, updates, and/or revisions (e.g., advanced LTE project, ultra mobile broadband (UMB) project (also referred to as "3GPP2"), etc.). IEEE 802.16-compatible Broadband Wireless Access (BWA) networks are generally referred to as WiMAX networks, an acronym that stands for Worldwide Interoperability for Microwave Access, which is a certification mark for products that pass conformity and interoperability tests for the IEEE 802.16 standards. The communication device 208 may operate in accordance with a Global System for Mobile Communication (GSM), General Packet Radio Service (GPRS), Universal Mobile Telecommunications System (UMTS), High Speed Packet Access (HSPA), Evolved HSPA (E-HSPA), or LTE network. The communication device 208 may operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication device 208 may operate in accordance with Code Division Multiple Access (CDMA), Time Division Multiple Access (TDMA), Digital Enhanced Cordless Telecommunications (DECT), Evolution-Data Optimized (EV-DO), and derivatives thereof, as well as any other wireless protocols that are designated as 3G, 4G, 5G, and beyond. The communication device 208 may operate in accordance with other wireless protocols in other embodiments.

Multiple communication devices included in the communication device 208 may enable communication in accordance with different communication protocols. For instance, a first communication chip may be dedicated to shorter-range wireless communications such as Wi-Fi and Bluetooth, and a second communication chip may be dedicated to longer range wireless communications such as GPS, EDGE, GPRS, CDMA, WiMAX, LTE, EV-DO, and others. In another example, a first communication chip may be dedicated to wired communications, and a second communication chip may be dedicated to wireless communications.

In some embodiments, the I/O devices 202 may include a display device 218. The display device 218 may provide a visual representation of data captured by the COPD severity estimation system 200 and/or data generated by the COPD severity estimation system 200 (e.g., COPD severity estimates). The display device 218 may include one or more heads-up displays (i.e., displays including a projector arranged in an optical collimator configuration and a combiner to provide data without requiring a user to look away from his or her typical viewpoint), computer monitors, projectors, touchscreen displays, liquid crystal displays (LCDs), light-emitting diode displays or flat panel displays, for example.

In some embodiments, the I/O devices 202 may include other I/O devices 220. Examples of other I/O devices 220 may include a keyboard, a cursor control device such as a mouse, a stylus, a touchpad, a bar code reader, a Quick Response (QR) code reader, an RFID reader, a GPS receiver, an audio capture device (which may include one or more microphones arranged in various configurations), one or more speakers or other audio transducers (which may be, e.g., mounted in one or more earphones or earbuds), printers, projectors, or any suitable I/O device.

The COPD severity estimation system 200 may include a control logic 204. The control logic 204 may include an I/O device interface 238 configured to receive data from and/or provide data to the I/O devices 202, and logic components configured to control the operation of the COPD severity estimation system 200. The I/O device interface 238 may include hardware to support any suitable communications between the I/O devices 202 and the control logic 204. Examples of communications protocols that may be supported by the I/O device interface 238 may include any of the wired and/or wireless communication protocols discussed above with reference to the communication device 208. In some embodiments, the I/O device interface 238 may support the inter-integrated circuit (I2C) protocol and/or the serial peripheral interface (SPI) protocol. For example, various ones of the sensors of the I/O devices 202 may communicate with a processor of the control logic 204 via the I2C protocol (e.g., an altimeter, a humidity sensor, a temperature sensor, and the locomotion sensor 214) and other ones of the sensors may communicate with a processor of the control logic 204 via the SPI protocol (e.g., the breathing sensor 212 and a USB connector of the other I/O devices 220). The I/O device interface 238 may also include hardware to support communication with the storage device 206. For example, communication between the control logic 204 and a micro secure digital (SD) card of the storage device 206 may be conducted via SPI protocol.

Although the components of the control logic 204 are illustrated separately, the components may be combined or divided as suitable, and each may use one or more of the results generated by others in performing its own analysis. Data may be communicated between the components of the control logic 204 over a physical bus, a long-distance wired communication pathway, a short- or long-distance wireless communication pathway, or any combination of communication pathways (e.g., any of the communication pathways or protocols discussed above with reference to the communication device 208 and the I/O device interface 238).

The COPD severity estimation system 200 may include a storage device 206 (which may, as discussed above, include multiple storage devices). In some embodiments, the storage device 206 may include a database or other data storage structure which may include memory structures for storing any of the data described herein used for COPD severity estimation operations (e.g., as discussed below with reference to FIG. 13). The storage device 206 may include any volatile or nonvolatile memory device, such as one or more hard drives, solid-state logic, or portable storage media, for example.

The control logic 204 may include breathing signal receipt logic 222, which may be configured to receive a breathing signal representative of breathing activity of a patient. The breathing signal receipt logic 222 may be coupled with the I/O devices 202, and may receive the breathing signal from the breathing sensor 212 (e.g., via the I/O device interface 238). In some embodiments, the breathing signal receipt logic 222 may be implemented by a programmed microcontroller that may be coupled with a breathing sensor 212. This coupling may be permanent or selectable in that the breathing signal receipt logic 222 and the breathing sensor 212 can be readily coupled and uncoupled. In some embodiments, the breathing signal receipt logic 222 may receive the breathing signal by storing the breathing signal (and/or a processed version of the breathing signal) in the storage device 206.

The breathing signal may take any suitable form to represent breathing activity of the patient. For example, in some embodiments, the breathing signal may represent contraction/expansion of the patient's chest during breathing (e.g., as measured by a resistive or capacitive chest strap sensor that at least partially encircles the patient's chest, or as measured by another motion sensor responsive to the motion of a patient's chest during breathing). In some embodiments, the breathing signal may represent the volume and/or rate of airflow during breathing (e.g., as measured by a nasal cannula). In some embodiments, the breathing signal may be expressed in breaths per time unit.

The breathing signal receipt logic 222 may receive a breathing signal over a time interval. The duration of that time interval may be dictated by the amount of data storage to which the breathing signal receipt logic 222 has access in the storage device 206; once receipt of a breathing signal commences, it may continue until there is no available data storage, and may be recommenced once storage is available. The duration of that time interval may be predetermined to a fixed amount, and the breathing signal receipt logic 222 may include a timer for ceasing receipt (or storage) of the breathing signal after the fixed amount has elapsed. The duration of breathing signal received should be adequate to capture the breathing phenomena of interest. In some embodiments, at least 45 seconds of breathing data may be received by the breathing signal receipt logic 222. The breathing signal receipt logic 222 may normalize a received breathing signal such that the maximum magnitude of the breathing signal over the time interval has a value of 1.

Receipt of the breathing signal by the breathing signal receipt logic 222 (e.g., storage of the breathing signal in the storage device 206) may be initiated in any suitable manner. For example, in some embodiments, the breathing signal receipt logic 222 may initiate receipt of the breathing signal in response to detection of breathing activity of the patient (e.g., by detecting activity from the breathing sensor 212 above a predetermined threshold that distinguishes likely noise from breathing activity). In some embodiments, the breathing signal receipt logic 222 may initiate receipt of the breathing signal in response to the patient or a care provider pressing an "on" or "start" button. In some embodiments, the breathing signal receipt logic 222 may initiate receipt of the breathing signal at a predetermined time (e.g., 9:00 AM every day). In some embodiments, the breathing sensor 212 may include a chest strap sensor, and the breathing signal receipt logic 222 may be configured to receive the breathing signal from the chest strap sensor. In some embodiments, the breathing signal receipt logic 222 may be configured with an analog or digital filter to filter the breathing signal upon receipt (e.g., to generate locomotion data). For example, the breathing signal receipt logic 222 may low-pass filter the breathing signal with an appropriate cutoff frequency to reduce noise. A cutoff frequency of 0.5 Hertz may be suitable. In other embodiments, no filtering or different filtering may be performed.

The control logic 204 may include a locomotion signal receipt logic 224, which may be configured to receive a locomotion signal representative of locomotive activity of the patient. The locomotion signal receipt logic 224 may be coupled with the I/O devices 202, and may receive the locomotion signal from the locomotion sensor 214 (e.g., via the I/O device interface 238). In some embodiments, the locomotion signal receipt logic 224 may be implemented by a programmed microcontroller that may be coupled with a locomotion sensor 214. This coupling may be permanent or selectable in that the locomotion signal receipt logic 224 and the locomotion sensor 214 can be readily coupled and uncoupled. In some embodiments, the locomotion signal receipt logic 224 may receive the locomotion signal by storing the locomotion signal (and/or a processed version of the locomotion signal) in the storage device 206.

The locomotion signal may take any suitable form to represent locomotive activity of the patient. For example, the locomotion signal may represent the up-and-down and/or forward-and-backward motion of one or more body parts of the patient during locomotion (e.g., as measured by an accelerometer). In some embodiments, the locomotion signal may represent a pressure experienced by the patient's foot against a shoe or the ground during walking (e.g., as measured by a pressure sensor in the patient's shoe or sock). In some embodiments, the locomotion signal may be expressed in steps per time unit.

The locomotion signal receipt logic 224 may receive a locomotion signal over a time interval. The duration of that time interval may be dictated by the amount of data storage to which the locomotion signal receipt logic 224 has access in the storage device 206; once receipt of a locomotion signal commences, it may continue until there is no available data storage, and may be recommenced once storage is available. The duration of that time interval may be predetermined to a fixed amount, and the locomotion signal receipt logic 224 may include a timer for ceasing receipt (or storage) of the locomotion signal after the fixed amount has elapsed. The duration of locomotion signal received should be adequate to capture the locomotion phenomena of interest. In some embodiments, at least 45 seconds of locomotion data may be received by the locomotion signal receipt logic 224. The locomotion signal receipt logic 224 may normalize a received locomotion signal such that the maximum magnitude of the locomotion signal over the time interval has a value of 1 (as measured, e.g., in multiples of the acceleration due to gravity).

In some embodiments, the locomotion signal receipt logic 224 may be configured with an analog or digital filter to filter the locomotion signal upon receipt (e.g., to generate locomotion data). For example, the locomotion signal receipt logic 224 may low-pass filter the locomotion signal with an appropriate cutoff frequency to reduce noise. A cutoff frequency of 10 Hertz may be suitable. In other embodiments, no filtering or different filtering may be performed.

Receipt of the locomotion signal by the locomotion signal receipt logic 224 (e.g., storage of the locomotion signal in the storage device 206) may be initiated in any suitable manner. For example, in some embodiments, the locomotion signal receipt logic 224 may initiate receipt of the locomotion signal in response to detection of locomotive activity of the patient (e.g., by detecting activity from the locomotion sensor 214 above a predetermined threshold that distinguishes likely noise from locomotive activity). In some embodiments, the locomotion signal receipt logic 224 may initiate receipt of the locomotion signal in response to the patient or a care provider pressing an "on" or "start" button. In some embodiments, the locomotion signal receipt logic 224 may initiate receipt of the locomotion signal at a predetermined time.

The control logic 204 may include a data provision logic 226, which may be configured to provide breathing data and locomotion data to the estimate generation logic 228 (discussed in detail below). The data provision logic 226 may be coupled with the breathing signal receipt logic 222, and the breathing data may be based on the breathing signal received by the breathing signal receipt logic 222. The data provision logic 226 may be coupled with the locomotion signal receipt logic 224, and the locomotion data may be based on the locomotion signal received by the locomotion signal receipt logic 224. In some embodiments, the data provision logic 226 may normalize the breathing data and/or the locomotion data so that the maximum magnitude of the data over a time interval of interest is 1 to facilitate cRQA.

In some embodiments, the data provision logic 226 may be configured with an analog or digital filter to filter the breathing signal and/or the locomotion signal to generate the breathing data and/or locomotion data, respectively, before providing the breathing data and/or locomotion data, respectively, to other logic (e.g., instead of or in addition to a filter applied by the breathing signal receipt logic 222 and/or the locomotion signal receipt logic 224, respectively). For example, the data provision logic 226 may low-pass filter the breathing signal with an appropriate cut-off frequency (e.g., 0.5 Hertz). For example, the data provision logic 226 may low-pass filter the locomotion signal with an appropriate cut-off frequency (e.g., 10 Hertz). In some embodiments, the breathing data provided by the data provision logic 226 may be the breathing signal (or a portion thereof) received by the breathing signal receipt logic 222. In some embodiments, the locomotion data provided by the data provision logic 226 may be the locomotion signal (or a portion thereof) received by the locomotion signal receipt logic 224. The data provision logic 226 may access the breathing data (or generate the breathing data based on access to the breathing signal) from a storage device 206 commonly accessible to the data provision logic 226 and the breathing signal receipt logic 222. The breathing data and/or locomotion data may be stored as comma delimited text files, in some embodiments.

The data provision logic 226 may access the locomotion data (or generate the locomotion data based on access to the locomotion signal) from a storage device 206 commonly accessible to the data provision logic 226 and the locomotion signal receipt logic 224. For example, the data provision logic 226 may interface with a storage device 206 that is also accessible to the breathing signal receipt logic 222 and the locomotion signal receipt logic 224 (e.g., via a USB connection from the data provision logic 226 to the storage device 206). The data provision logic 226 may enumerate the storage device 206 as a mass storage device, and upon successful enumeration, the data from the storage device may be transferred to the data provision logic 226 (e.g., via USB). In some embodiments, the data provision logic 226 may compress the breathing and locomotion data before providing the breathing and locomotion data to the estimate generation logic 228 (e.g., using a ZIP protocol).

In some embodiments, the data provision logic 226 may provide the respiration data and the locomotion data to the estimate generation logic 228 by providing the respiration data and the locomotion data for storage in a storage device (e.g., the storage device 206) that is accessible to the estimate generation logic 228. This commonly accessible storage device may be remote from one or both of the data provision logic 226 and the estimate generation logic 228. Examples of such embodiments are discussed below with reference to FIG. 9.

The control logic 204 may include estimate generation logic 228, which may be configured to generate an estimate of COPD severity in the patient by comparison of 1) a cRQA parameter comparing the breathing data and the locomotion data and 2) a reference value. The estimate generation logic 228 may be coupled with the data provision logic 226 and may receive the respiration data and the locomotion data from the data provision logic 226. In some embodiments, the estimate generation logic 228 may be implemented by a high-performance computing device, such as a computing cluster or server-based computing device.

The estimate generation logic 228 may generate a cross-recurrence data set as part of generation of a cRQA parameter. A cross-recurrence data set comparing a series of vectors $X_i$ to a series of vectors $Y_j$ may be denoted $R_{XY}(i,j)$, and may be computed in accordance with $$R_{XY}(i, j) = \begin{cases} 1 & \|X_i - Y_j\| < \varepsilon \\ 0 & \text{otherwise} \end{cases}$$

where the radius E is positive and the norm is the Euclidean norm. Other norms may be used, and a value (i,j) for which $R_{XY}(i, j)$ is positive may be referred to as a "point." The vector $X_i$ may be an embedding of a time series $x_i$ such that $$X_i = [x_i, x_{i+\tau}, x_{i+2\tau}, \ldots, x_{i+m\tau}]$$

where m is the embedding dimension and $\tau$ is the delay associated with the embedding. Consequently, the vector $X_i$ may be an m-dimensional vector. The vector $Y_j$ may be analogously embedded based on a time series Examples of techniques for determining an appropriate radius, embedding dimension, and delay are discussed below with reference to FIG. 11. The vectors $X_i$ may represent the breathing data, and the vectors $Y_j$ may represent the locomotion data in the notation herein.

Figure 12:
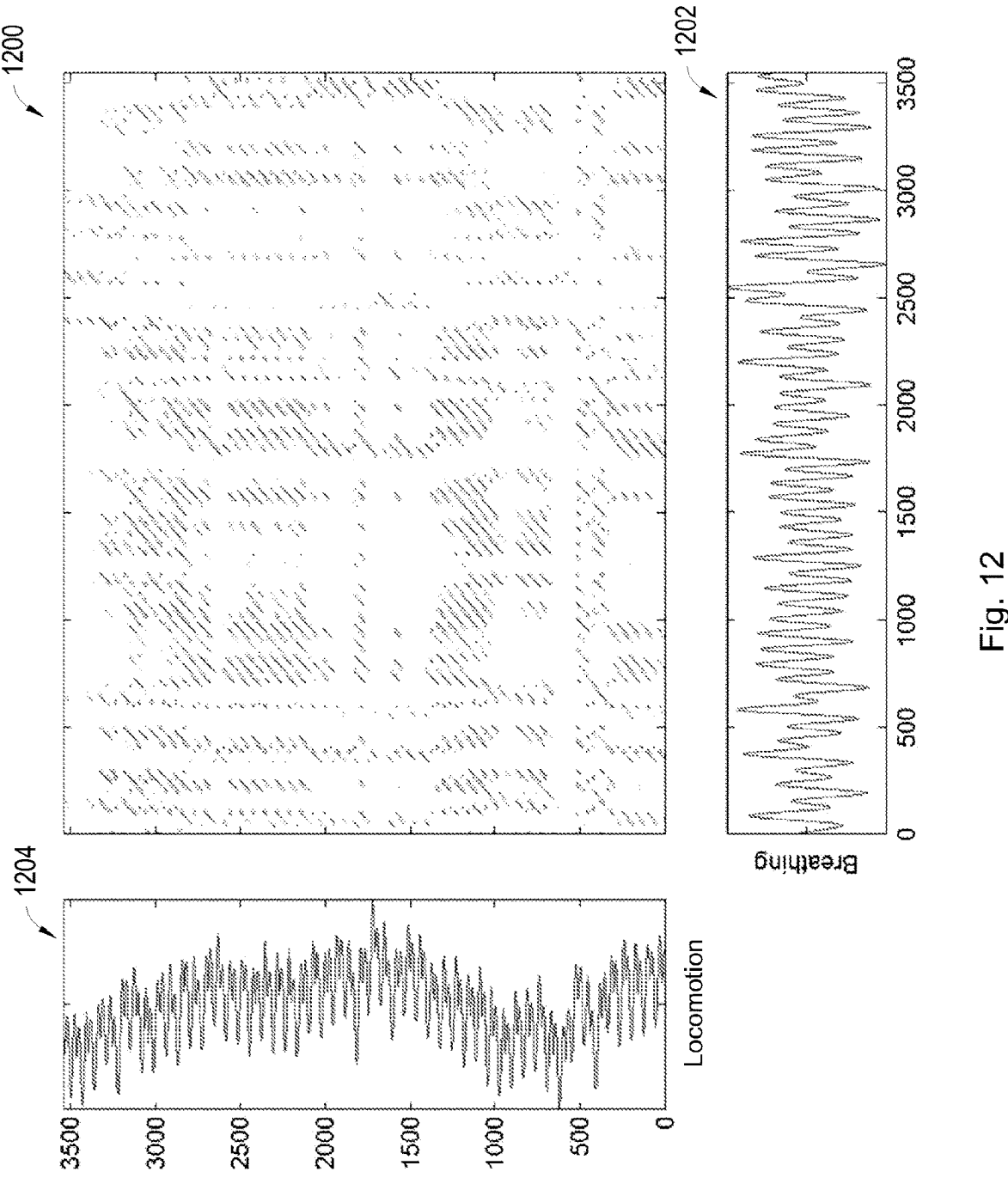
FIG. 12 is an example recurrence plot of breathing and locomotion data for a COPD patient, along with the associated time series, that may be generated by the COPD severity estimation system of FIG. 2, in accordance with various embodiments.

In some embodiments, the estimate generation logic 228 may generate a recurrence plot of the cross-recurrence data. FIG. 12 is an example recurrence plot 1200 of normalized breathing and locomotion data for a COPD patient, along with plots of an associated breathing data time series 1202 and an associated locomotion data time series 1204, that may be generated by the estimate generation logic 228 of the COPD severity estimation system 200. In a recurrence plot, a point is positioned at location (i,j) when $R_{XY}(i,j)$ is equal to 1, and no point is positioned at other locations.

In some embodiments, the estimate generation logic 228 may generate the percent determinism of the cross-recurrence data set as a parameter comparing the breathing data and the locomotion data. "Percent determinism" is defined herein as the percentage of points that fall on a diagonal line within the recurrence plot. The estimate generation logic 228 may identify a diagonal line in the cross-recurrence data set when at least N points are diagonally adjacent (e.g., {(i,j), (i+1,j+1), . . . , (i+N−1, j+N−1)}), where N is a predetermined integer. A suitable choice for N may represent a sufficient duration of data to capture the phenomena of interest; a value of N that is too small may spuriously capture noise as coordinated signals. For example, in embodiments where the data sampling rate is 60 Hertz, a choice of N=6 may represent 100 milliseconds of data. This duration may be appropriate, as it may account for corticospinal latency and as any coupling happening under this time frame may be spurious and/or represent reflex movement. The estimate generation logic 228 may generate the percent determinism by calculating the number of points included in a diagonal line divided by the total points (and multiplying by 100). In a perfectly periodic system, a percent determinism will be 100%, while in a system without any periodicity, the percent determinism will be closer to 0%. A patient's COPD severity may be estimated using percent determinism; in particular, an increased percent determinism value may indicate an increased COPD severity.

In some embodiments, the estimate generation logic 228 may generate a maximum diagonal line length of the cross-recurrence data set as a parameter comparing the breathing data and the locomotion data. A diagonal line in the cross-recurrence data set may be defined as discussed above, and the estimate generation logic 228 may compute all of the lengths of the diagonal lines in the cross-recurrence data set and identify the maximum value of these lengths as the maximum diagonal line length.

In some embodiments, the estimate generation logic 228 may generate a mean diagonal line length of the cross-recurrence data set as a parameter comparing the breathing data and the locomotion data. A diagonal line in the cross-recurrence data set may be defined as discussed above, and the estimate generation logic 228 may compute all of the lengths of the diagonal lines in the cross-recurrence data set and identify the mean value of these lengths as the mean diagonal line length. A patient's COPD severity may be estimated using mean diagonal line length; in particular, an increased mean diagonal line length value may indicate an increased COPD severity.

In some embodiments, the estimate generation logic 228 may generate a percent recurrence of the cross-recurrence data set as a parameter comparing the breathing data and the locomotion data. The estimate generation logic 228 may generate the percent recurrence by dividing the number of points in the cross-recurrence data set by the total number of possible points (and multiplying by 100). The percent recurrence may analogously be defined as the percentage of the area of a recurrence plot of the cross-recurrent data set that is occupied by points. A patient's COPD severity may be estimated using percent recurrence; in particular, a decreased percent recurrence value may indicate an increased COPD severity.

In some embodiments, the estimate generation logic 228 may generate an entropy of diagonal line lengths of the cross-recurrence data set as a parameter comparing the breathing data and the locomotion data. The estimate generation logic 228 may calculate the entropy of diagonal line lengths in accordance with $$-\sum_l P_l \log_2 P_l$$

where $P_l$ is the probability that a diagonal line (defined as discussed above) has a length 1. The values $P_l$ may be generated from the estimate generation logic 228 from a histogram of the diagonal line lengths of the cross-recurrence data set. The entropy of diagonal line lengths may represent the probability that the length of a diagonal line was repeated, and thereby represent the variety of patterns or complexity within the two data sets. A patient's COPD severity may be estimated using entropy; in particular, an increased entropy value may indicate an increased COPD severity.

In some embodiments, the estimate generation logic 228 may generate any of a number of other parameters comparing the breathing data and the locomotion data. In some embodiments, one or more such parameters may not be cRQA parameters. For example, the estimate generation logic 228 may generate a cross-correlation of the breathing and locomotion data series. The estimate generation logic 228 may calculate the cross-correlation in accordance with $$r_{x,y} = \sum_{i=0}^{N-1} x_i y_i$$

where N is the number of data points in each data series, $x_i$ is the $i^{th}$ data point of the first data series, $y_i$ is the $i^{th}$ data point of the second data series, and $r_{x,y}$ is the correlation. Cross-correlation values range between −1 and +1. In some embodiments, the estimate generation logic may identify and store the maximum value of the cross-correlation.

In another example, the estimate generation logic 228 may generate a frequency ratio comparing the breathing data and the locomotion data. The frequency ratio may represent the number of steps per breath. In embodiments where the locomotion data represent the motion of the patient's heel, steps may be identified by locating heel strikes in the locomotion data (e.g., at local maxima of a heel acceleration signal). In some embodiments, the estimate generation logic 228 may calculate a discrete relative phase between the breathing data and the timing of heel strikes or other indication of steps, as known in the art. Based on the discrete relative phase value, the number of steps within a breath can be calculated. For instance, if the discrete relative phase is between 0° and 360°, there was one heel strike. However, if the returned value is between 360° and 720°, there were two heel strikes, and so forth.

As noted above, the estimate generation logic 228 may be configured to generate an estimate of COPD severity in the patient by comparison of 1) a cRQA parameter comparing the breathing data to and the locomotion data (e.g., one or more of the cRQA parameters discussed above) and 2) a reference value. In some embodiments, the reference value may be a value of a cRQA parameter from a reference population. For example, the reference value may be an average value of the cRQA parameter in the reference population. In another example, the reference value may be an average value of the cRQA parameter in the reference population, plus or minus one or more standard deviations. In another example, the reference value may be a value of the cRQA parameter from the reference population at a predetermined percentile (e.g., the 90th percentile). The reference population may be, for example, a population without COPD (age-matched to the patient or not age-matched to the patient), a population with COPD (age-matched to the patient or not age-matched to the patient), a population with COPD of a particular Body mass index, airflow Obstruction, Dyspnea, and Exercise (BODE) index, a population with COPD of a particular GOLD Global initiative for chronic Obstructive Lung Disease) classification, or any other suitable reference population.

In some embodiments, the reference value may be a previously obtained value of the cRQA parameter from the patient. For example, the reference value may be a value of the cRQA parameter obtained from the patient at the time that the most recent past measurements were taken (e.g., at the last care provider appointment, or at the previous day). In another example, the reference value may aggregate several previously obtained values of the cRQA parameter from the patient (e.g., the average value over several past measurement periods, plus or minus one or more standard deviations).

The estimate generation logic 228 may use the cRQA parameter and the reference value to generate an estimate of COPD severity in the patient. In some embodiments, when the reference value is representative of a reference population, the estimate of COPD severity may be an indication that the patient's COPD is elevated with respect to a reference population. For example, when the cRQA parameter is percent determinism, entropy, or mean diagonal line length, if the value of the cRQA parameter is greater than a value of the same cRQA parameter for the reference population (e.g., an average, plus an optional one or more standard deviations), the estimate generation logic 228 may indicate that the patient's COPD is elevated with respect to the reference population. In another example, when the cRQA parameter is percent recurrence, if the value of the cRQA parameter is less than a value of the same cRQA parameter for the reference population (e.g., an average, plus an optional one or more standard deviations), the estimate generation logic 228 may indicate that the patient's COPD is elevated with respect to the reference population.

In some embodiments, the estimate of COPD severity may be an indication that the patient's COPD has increased in severity from a previous time. For example, when the cRQA parameter is percent determinism, entropy, or mean diagonal line length, and the reference value is a previously obtained value of the cRQA parameter from the patient (e.g., a single previously obtained value or aggregate of multiple previously obtained values), and the cRQA parameter is greater than the reference value, the estimate generation logic 228 may indicate that the patient's COPD has increased in severity. In another example, when the cRQA parameter is percent recurrence, the reference value is a previously obtained value of the cRQA parameter from the patient (e.g., a single previously obtained value or aggregate of multiple previously obtained values), and the cRQA parameter is less than the reference value, the estimate generation logic 228 may indicate that the patient's COPD has increased in severity.

Figure 14:
FIG. 14 is a representation of an illustrative display for displaying data generated and/or used by the COPD severity estimation system of FIG. 2, in accordance with various embodiments.

Returning to FIG. 2, the COPD severity estimation system 200 may include an estimate notification logic 236. The estimate notification logic 236 may be coupled to the estimate generation logic 228 and to the I/O devices 202 (via the I/O device interface 238) and may be configured to notify the patient or one or more care providers of the COPD severity estimate generated by the COPD severity estimation system 200. In some embodiments, the estimate notification logic 236 may be coupled to the display device 218, and may be configured to cause the estimate of COPD severity to be displayed on the display device 218. The estimate notification logic 236 may be configured to cause the display of additional information along with the estimate of COPD severity. This additional information may include a BODE index for the patient, a GOLD classification for the patient, or an EXAcerbations of Chronic pulmonary disease Tool (EXACT) score for the patient, for example. An illustrative display that may be displayed on the display device 218 upon the instruction of the estimate notification logic 236 is shown in FIG. 14 and discussed below.

In some embodiments, the estimate notification logic 236 may be configured to provide a notification of the COPD severity estimate by causing a textual and/or graphic message to be sent to the patient personal computing device 104 and/or the care provider computing device 110. This notification may take the form of an e-mail, a text message, a social media message, a message in a proprietary communication system (such as a messaging system provided by an insurance company or healthcare system), or any other suitable form. In some embodiments, the estimate notification logic 236 may be configured to provide a notification of the COPD severity estimate to an electronic patient record system maintained by a healthcare facility, and the electronic patient record system may update a patient's file or "chart" with the COPD severity estimate.

The COPD severity estimation system 200 may include a charging logic 230, which may be configured to charge an energy storage device (e.g., a battery) of the wearable computing device 102 when the wearable computing device 102 is appropriately coupled to the charging logic 230 (e.g., via a cable that supports charging, such as a universal serial bus (USB) cable, or via an inductive or other "wireless" charging apparatus). When sufficiently charged, the wearable computing device 102 may be decoupled from the charging logic 230 and worn by the patient.

The COPD severity estimation system 200 may include heart rate logic 232, which may be coupled to the heart rate sensor 210 and may be configured to receive a heart rate signal representative of a rate of heartbeats of the patient. In some such embodiments, the data provision logic 226 may be coupled to the heart rate logic 232, and the data provision logic 226 may be configured to provide heart rate data, based on the heart rate signal, to the estimate notification logic 236. The estimate notification logic 236 may in turn cause the estimate of COPD severity (generated by the estimate generation logic 228) to be displayed simultaneously with the heart rate of the patient (based on the heart rate data) on the display device 218. The illustrative display of FIG. 14, discussed in further detail below, includes the patient's heart rate, for example. The estimate notification logic 236 may notify the patient and/or care provider of the patient's heart rate in accordance with any of the embodiments discussed above with reference to notification of the COPD severity estimate.

The COPD severity estimation system 200 may include a locomotion prompt logic 234, which may be configured to generate a prompt to the patient to begin locomotion. In some embodiments, the locomotion prompt logic 234 may be coupled to the locomotion signal receipt logic 224 and may be configured to generate a prompt to the patient to begin locomotion upon a determination that the patient has not engaged in locomotive activity for a predetermined period of time. In some embodiments, the locomotion prompt logic 234 may be coupled to clock logic (not shown in FIG. 2) and may be configured to generate a prompt to the patient to begin locomotion at a particular time or times (e.g., at 9:00 AM each day). The prompt may take the form of a visual or audio message provided to the patient personal computing device 104 for display to the patient, or a tactile, visual, or audio message provided to the wearable computing device 102 (e.g., a vibration or a tone). In some embodiments, the prompt may include a temporal component that indicates to the patient a period of time over which he or she should engage in locomotive activity. For example, the wearable computing device 102 may emit a tone at regular intervals that ceases when the patient has moved for long enough for a sufficient locomotion signal to be received by the locomotion signal receipt logic 224.

As discussed above with reference to FIGS. 1 and 2, the components of the COPD severity estimation system 200 may be distributed in any suitable manner between the computing devices of the computing system 100, and the computing devices of the computing system 100 may be themselves distributed in any suitable manner among sub-computing devices. FIGS. 3-6 are block diagrams of various arrangements of various components of the control logic 204 of the COPD severity estimation system 200, in accordance with various embodiments.

Figures 3, 6:
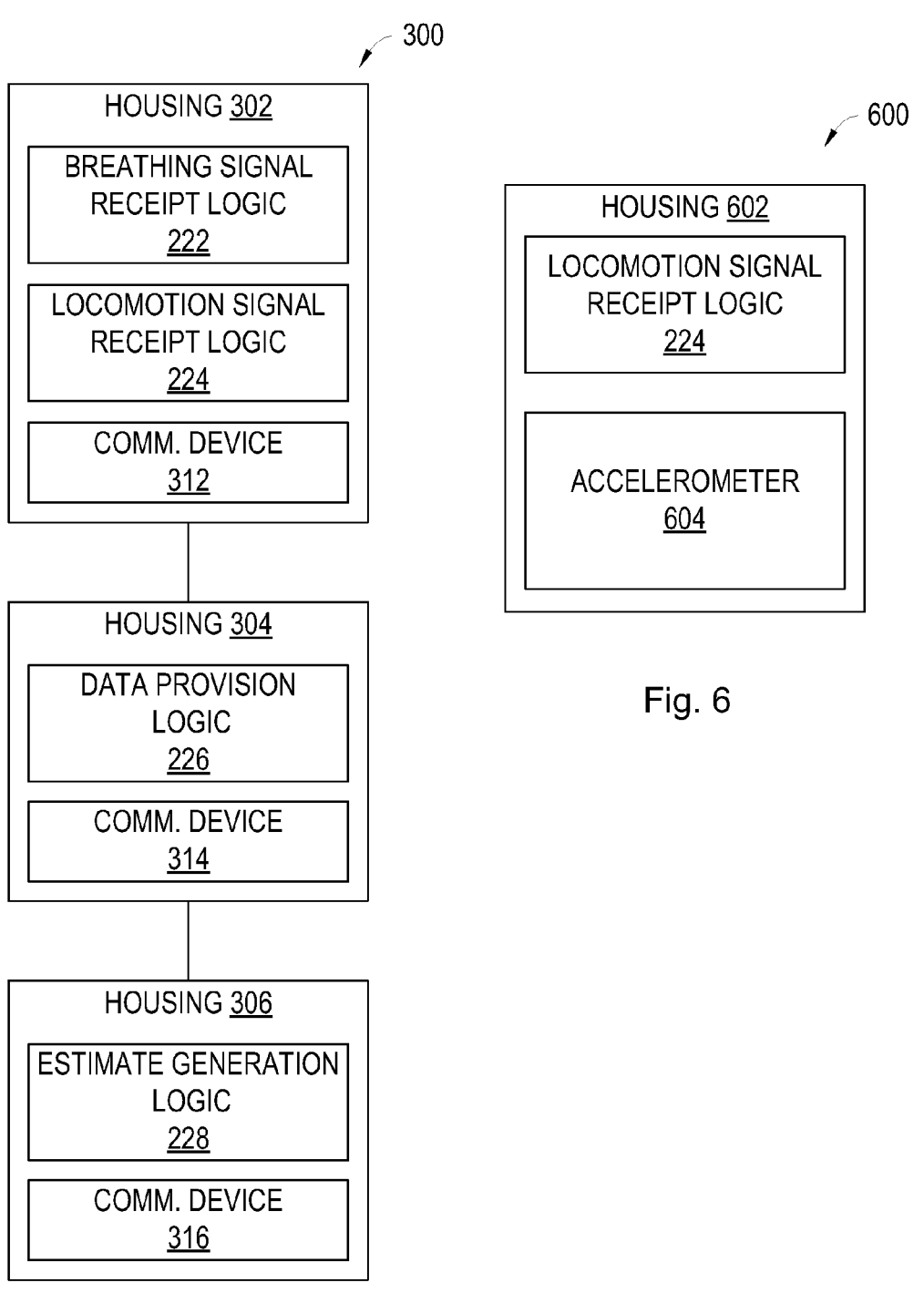
FIGS. 3-6 are block diagrams of various arrangements of various components of the control logic of the COPD severity estimation system of FIG. 2, in accordance with various embodiments.

FIG. 3 depicts an arrangement 300 in which the breathing signal receipt logic 222, the locomotion signal receipt logic 224, and a communication device 312 are included in a housing 302. The data provision logic 226 and a communication device 314 are included in a housing 304 that is different from the housing 302, but the housing 302 and the housing 304 may be in communication via the communication devices 312 and 314. The estimate generation logic 228 and a communication device 316 are included in a housing 306 that is different from the housing 302 and the housing 304, but the housing 304 and the housing 306 may be in communication via the communication devices 314 and 316. In some embodiments, the housing 302 and the housing 306 may not be in direct communication, but may communicate via intermediate components in the housing 304. In some embodiments, the housing 302 and the housing 304 may be in communication via a commonly accessible storage device (not shown in FIG. 3, but discussed below with reference to FIG. 9). In some embodiments, the housing 304 and the housing 306 may be in communication via a commonly accessible storage device (not shown). The communication devices 312, 314, and 316 may be included in, and may take the form of any of the embodiments of, the communication device 208 of the COPD severity estimation system 200.

In some embodiments of the arrangement 300 of FIG. 3, the housing 302 is a housing of the wearable computing device 102, the housing 304 is a housing of the dock computing device 106 or the patient personal computing device 104, and the housing 306 is a housing of the remote computing device 108 or the care provider computing device 110.

For example, when the housing 304 is a housing of the dock computing device 106, the housing 304 may have a connector to receive a mating connector of the housing 302. In such an embodiment, the breathing signal receipt logic 222 may be configured to store the breathing signal or breathing data in a storage device (not shown) in the housing 302, the locomotion signal receipt logic 224 may be configured to store the locomotion signal or locomotion data in a storage device (not shown) in the housing 302, and when the connectors of the housing 302 and the housing 304 are mated, the data provision logic 226 may be configured to read the information stored in the storage device(s) of the housing 302. Such an embodiment is discussed in further detail below with reference to FIG. 4.

In another example, when the housing 304 is a housing of a patient personal computing device 104 (e.g., a smartphone), the communication device 312 and the communication device 314 may be wireless communication devices (e.g., short-range wireless communication devices, such as Bluetooth devices). In such an embodiment, the breathing signal receipt logic 222 may be configured to store the breathing signal or breathing data in a storage device (not shown) in the housing 302, the locomotion signal receipt logic 224 may be configured to store the locomotion signal or locomotion data in a storage device (not shown) in the housing 302, and when the communication devices 312 and 314 are in communication, the data provision logic 226 may be configured to read the information stored in the storage device(s) of the housing 302.

In another example, the communication device 314 and the communication device 316 may be wireless communication devices (e.g., long-range wireless communication devices, such as cellular devices). In such an embodiment, the data provision logic 226 may provide the breathing data and the locomotion data to the estimate generation logic 228 wirelessly. In one particular example of such an embodiment, the housing 304 may be a housing of the dock computing device 106, and may wirelessly transmit the breathing data and the locomotion data to a cloud storage service, where it is accessible by a high-performance computer or other computing device instantiating the estimate generation logic 228 (e.g., the remote computing device 108 or the care provider computing device 110).

Figure 4:
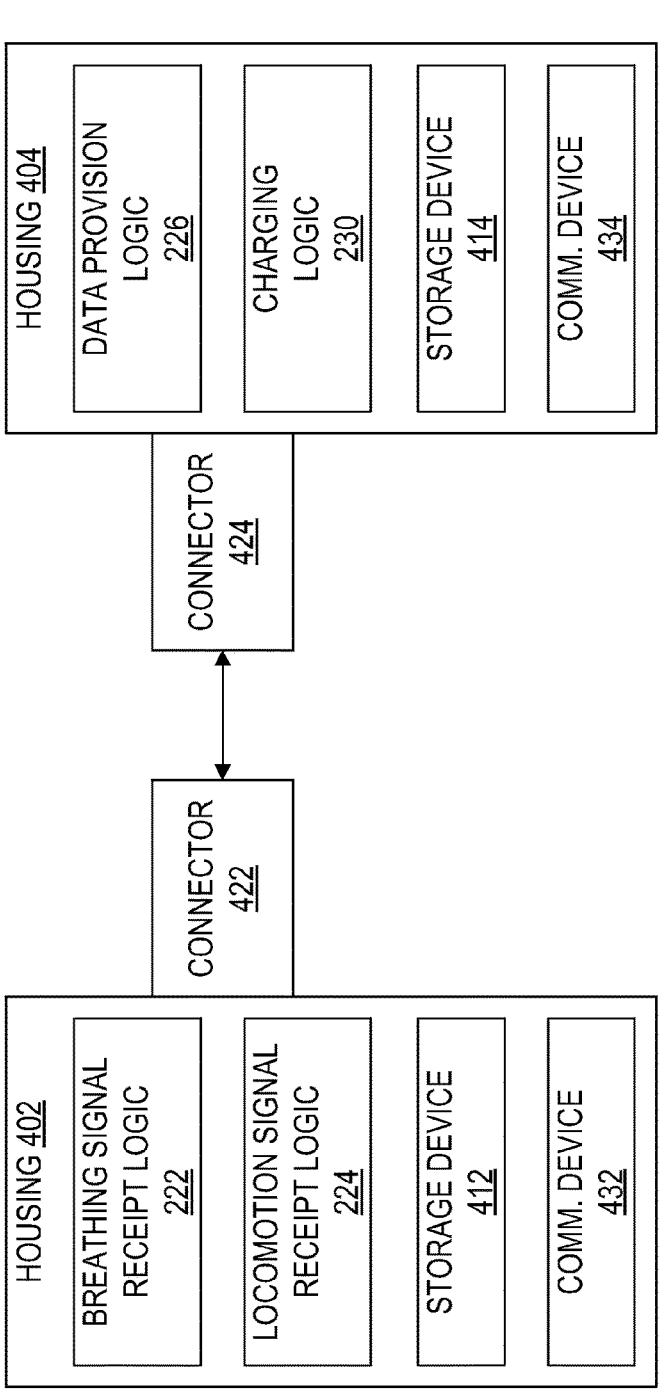

FIG. 4 depicts an arrangement 400 representing a portion of an embodiment of the arrangement 300 of FIG. 3. In FIG. 4, the breathing signal receipt logic 222, the locomotion signal receipt logic 224, and the communication device 312 are included in a housing 402, along with a storage device 412 and a communication device 432. The data provision logic 226, the charging logic 230, a storage device 414, and a communication device 434 are included in a housing 404 that is different from the housing 402, but the housing 402 and the housing 404 may be in communication via the communication devices 432 and 434. The housing 402 includes a connector 422 that removably mates with a connector 424 of the housing 404. The communication devices 432 and 434 may be included in, and may take the form of any of the embodiments of, the communication device 208 of the COPD severity estimation system 200. For example, the communication device 432 may support USB communication between the components of the housings 402 and 404 via the connectors 422 and 424. The storage devices 412 and 414 may be included in, and may take the form of any of the embodiments of, the storage device 206 of the COPD severity estimation system 200.

For example, when the housing 404 is a housing of the dock computing device 106, the breathing signal receipt logic 222 may be configured to store the breathing signal or breathing data in the storage device 412 in the housing 402, the locomotion signal receipt logic 224 may be configured to store the locomotion signal or locomotion data in the storage device 412 in the housing 402. When the connectors 422 and 424 are mated, the data provision logic 226 may be configured to read the information stored in the storage device 412 and store that information in the storage device 414. The charging logic 230 may charge an energy storage device (not shown) in the housing 402 when the connectors 422 and 424 are mated. Additionally, the communication device 434 of the housing 404 may be configured to provide the information stored by the data provision logic 226 in the storage device 414 to the estimate generation logic 228 (not shown).

Figure 5:
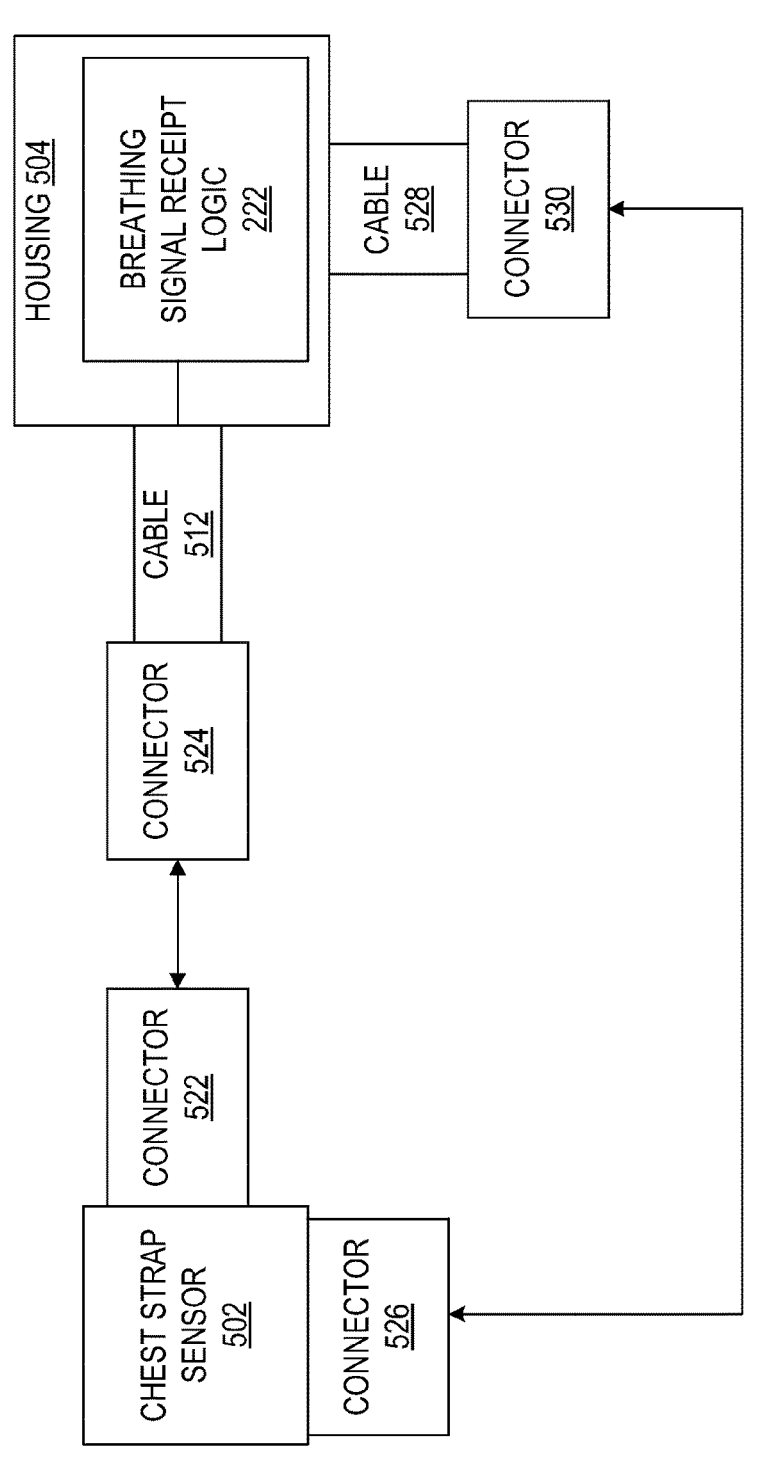

FIG. 5 depicts an arrangement 500 in which the breathing signal receipt logic 222 is included in a housing 504 having two cables 512 and 528 extending therefrom. The connectors 524 and 530 are disposed on the cables 512 and 528, respectively. The connectors 524 and 530 are removably mateable with the connectors 522 and 526 of a chest strap sensor 502. The chest strap sensor 502 may be included in the breathing sensor 212, and may take any of the forms of the chest strap sensor discussed above with reference to the breathing sensor 212. When the connector 522 is mated with the connector 524, the connector 526 is mated with the connector 530, and the chest strap sensor 502 is positioned around the patient's chest, the breathing signal receipt logic 222 may be able to receive a breathing signal from use of the chest strap sensor 502.

FIG. 6 depicts an arrangement 600 in which the locomotion signal receipt logic 224 and an accelerometer 604 are included in a housing 602. The accelerometer 604 may be included in the locomotion sensor 214, and may take any of the forms of the accelerometer discussed above with reference to the locomotion sensor 214. For example, in some embodiments, the accelerometer 604 may be an IMU. The locomotion signal receipt logic 224 may be coupled to the accelerometer 604 so that the locomotion signal receipt logic 224 is able to receive a locomotion signal from the accelerometer 604.

Figure 7:
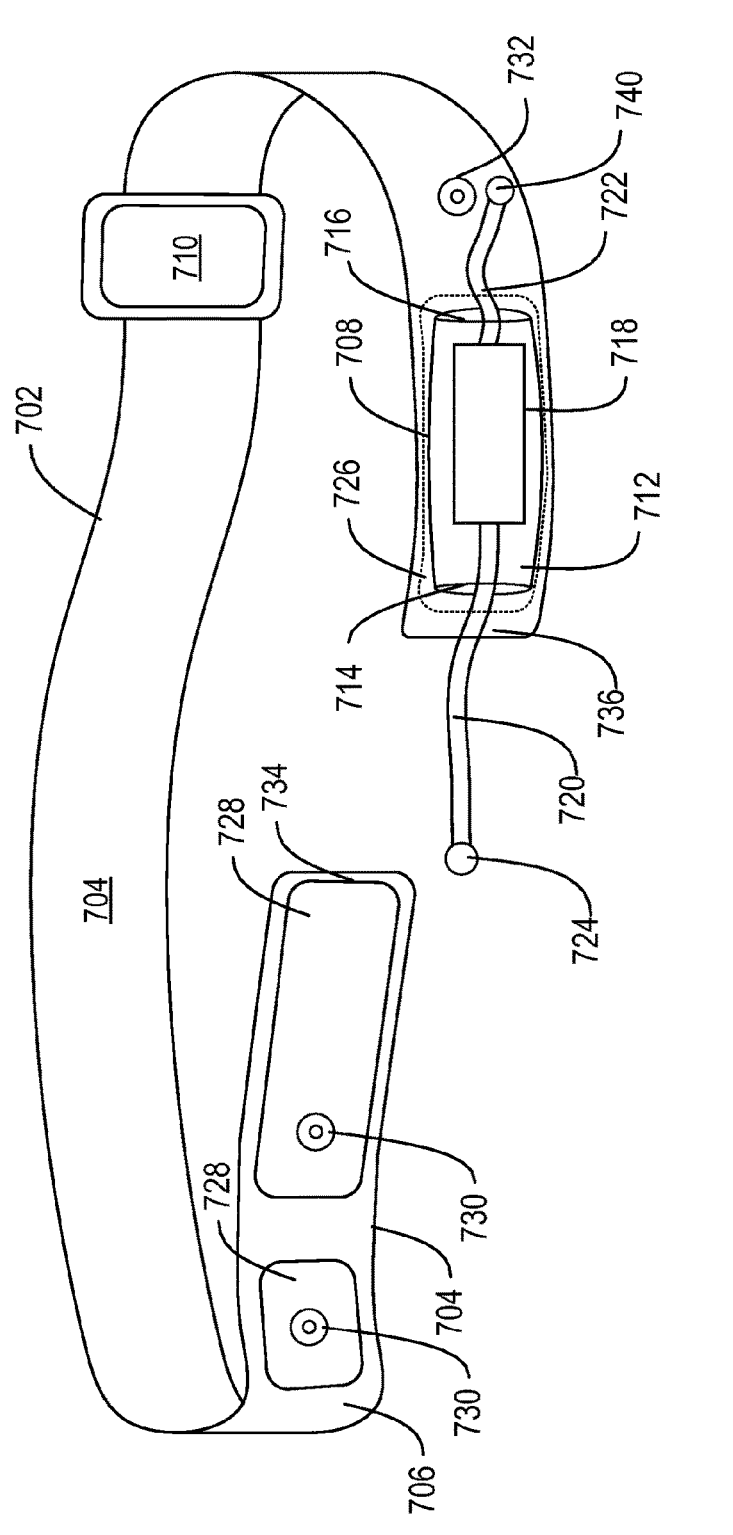
FIG. 7 is a perspective view of an example arrangement portion of a portion of the COPD severity estimation system of FIG. 2, in accordance with various embodiments.

FIG. 7 is a perspective view of an example arrangement 700 of a portion of the COPD severity estimation system 200, in accordance with various embodiments. In particular, the arrangement 700 may represent an embodiment of the arrangement 500 (FIG. 5) and the arrangement 600 (FIG. 6). In FIG. 7, a chest strap sensor 702 has a first end 734, a second end 736, an interior face 704, and an exterior face 706. When worn by a patient around his or her chest, the interior face 704 is arranged to face the patient's chest. A pocket 712 is disposed on the exterior face 706 proximate to the second end 736. The pocket 712 may have two openings: a first opening 714 proximate to the second end 736 and a second opening 716 distal to the second end 736. The pocket 712 may be sized to receive a housing 718 in which the breathing signal receipt logic 222 (not shown) and the locomotion signal receipt logic 224 (not shown) may be disposed. In this manner, the housing 718 may serve as both the housing 504 (FIG. 5) and the housing 602 (FIG. 6). In particular, the housing 718 may include both the breathing signal receipt logic 222 and the accelerometer 604 (not shown). In some embodiments, the housing 718 may have dimensions less than or equal to 1 inch by 2 inches by inch.

A first cable 720 may extend from the housing 718 through the first opening 714, and a second cable 722 may extend from the housing 718 through the second opening 716. The housing 718 and cables 720 and 722 may be removable from the pocket 712 and may be oriented in the "opposite" manner in the pocket 712 (i.e., so that the first cable 720 extends through the second opening 716 and the second cable 722 extends through the first opening 714). A first connector 724 may be disposed at an end of the first cable 720 opposite the housing 718, and a second connector 740 may be disposed at an end of the second cable 722 opposite the housing 718.

The first connector 724 may be mateable with one of multiple connectors 730 disposed on the exterior face 706 of the chest strap sensor 702 proximate to the first end 734. The connectors 730 are in electrical contact with the sensing material of the chest strap sensor 702, and thus provide electrical contact points for measuring a breathing signal using the chest strap sensor 702. The connectors 730 may be disposed on portions of hook material 728 that both reinforce the chest strap sensor 702 around the connectors 730 and may couple with corresponding loop material 726 disposed on the interior face 704 of the chest strap sensor 702 proximate to the second end 736. Multiple connectors 730 may enable a patient to adjust the diameter of the chest strap sensor 702 when in use and mate the first connector 724 with the appropriate one of the connectors 730 based on the diameter. Additionally, the coupling between the hook material 728 and the loop material 726 during use may provide strain relief to the first cable 720 when the first connector 724 is mated with a connector 730. In some embodiments, the first connector 724 may be a female snap, and the connectors 730 may be male snaps. In some embodiments, the first connector 724 and the connectors 730 may be complementary magnets.

The second connector 740 may be mateable with a connector 732 disposed on the exterior face 706 of the chest strap sensor 702 proximate to the second end 736. In some embodiments, the second connector 740 may be a female snap, and the connector 732 may be a male snap. In some embodiments, the second connector 740 and the connector 732 may be complementary magnets. The connector 732 is in electrical contact with the sensing material of the chest strap sensor 702, and thus provides an electrical contact point for measuring a breathing signal using the chest strap sensor 702. Thus, the arrangement 700 may serve as an embodiment of the arrangement 500 (FIG. 5): the chest strap sensor 702 may serve as the chest strap sensor 502, the connector 730 may serve as the connector 526, the connector 732 may serve as the connector 522, the second connector 740 may serve as the connector 524, the second cable 722 may serve as the cable 512, the first cable 720 may serve as the cable 528, and the first connector 724 may serve as the connector 530. When the first connector 724 and the second connector 740 are mated with the connectors 730 and 732, respectively, a closed circuit may be achieved and logic in the housing 718 (e.g., the locomotion signal receipt logic 224) may be able to receive a locomotion signal using the chest strap sensor 702.

The arrangement 700 may also include a slider 708 formed from a piece of fabric or other material wrapped around the chest strap sensor 702. The slider 708 may include a portion of a loop material 710 arranged on the interior face 704 of the chest strap sensor 702, and may "slide" along the chest strap sensor 702 and be positioned to provide an extra contact point with the hook material 728 on the exterior face 706 to further secure the chest strap sensor 702 around the patient's chest.

In some embodiments, the housing 718 may be an embodiment of the housing 402 of FIG. 4. In particular, the housing 718 may include the breathing signal receipt logic 222, the locomotion signal receipt logic 224, the storage device 412, and the communication device 432. The housing 718 may also include an additional connector (not shown) to serve as the connector 422. For example, the housing 718 may include a mini-USB socket or other connector that can mate with a mini-USB or other connector 424 from the housing 404 (which may be, for example, the dock computing device 106). In such an embodiment, after the chest strap sensor 702 has been worn and the logic in the housing 718 has received the breathing and locomotion signals (and stored them in the storage device 412), the housing 718 may be removed from the pocket 712 and a micro-USB or other cable may be coupled with the connector 422 to "dock" the housing 718 with the housing 404. Operation of this "docked" arrangement may proceed as discussed above with reference to FIG. 4. In other embodiments, the housing 718 may include the wireless communication device 432 (not shown) to wirelessly transmit information stored in the storage device 412 to the data provision logic 226 in the housing 404.

Figures 8, 9, 10:
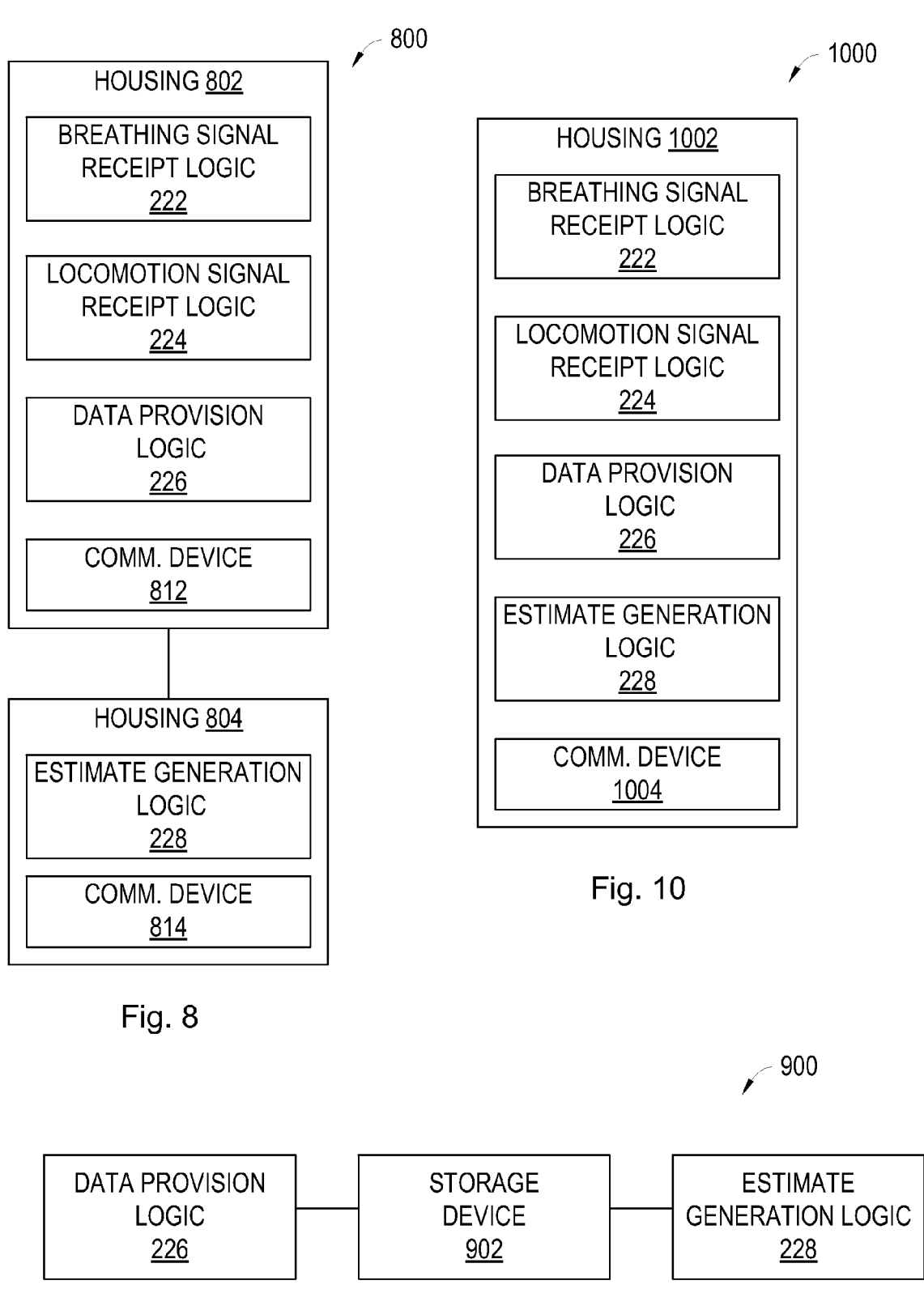
FIGS. 8-10 are block diagrams of various arrangements of various components of the control logic of the COPD severity estimation system of FIG. 2, in accordance with various embodiments.

FIG. 8 depicts an arrangement 800 in which the breathing signal receipt logic 222, the locomotion signal receipt logic 224, the data provision logic 226, and a communication device 812 are included in a housing 802. The estimate generation logic 228 and a communication device 814 are included in a housing 804 that is different from the housing 802, but the housing 802 and the housing 804 may be in communication via the communication devices 812 and 814. In some embodiments, the housing 802 and the housing 804 may be in communication via a commonly accessible storage device (not shown in FIG. 8, but discussed below with reference to FIG. 9). The communication devices 812 and 814 may be included in, and may take the form of any of the embodiments of, the communication device 208 of the COPD severity estimation system 200.

In some embodiments of the arrangement 800 of FIG. 8, the housing 802 is a housing of the wearable computing device 102, and the housing 804 is a housing of the remote computing device 108 or the care provider computing device 110.

In one example, the communication device 812 and the communication device 814 may be wireless communication devices (e.g., long-range wireless communication devices, such as cellular devices). In such an embodiment, the data provision logic 226 may provide the breathing data and the locomotion data to the estimate generation logic 228 wirelessly. In one particular example of such an embodiment, the housing 802 may be a housing of the wearable computing device 102 and may wirelessly transmit the breathing data and the locomotion data to a cloud storage service, where it is accessible by a high-performance computer or other computing device instantiating the estimate generation logic 228 (e.g., the remote computing device 108 or the care provider computing device 110).

FIG. 9 depicts an arrangement 900 in which the data provision logic 226 and the estimate generation logic 228 are in communication via a commonly accessible storage device 902. The storage device 902 may be included in, and may take any of the forms described above with reference to, the storage device 206 of FIG. 2. In some embodiments, the storage device 902 may be included in a common housing with the data provision logic 226, while the estimate generation logic 228 is included in a different housing. In some embodiments, the storage device 902 may be included in a common housing with the estimate generation logic 228, while the data provision logic 226 is included in a different housing. In some embodiments, the storage device 902 may be included in a common housing with the data provision logic 226 and the estimate generation logic 228. In some embodiments, the storage device 902 may be included in a housing different from a housing of the data provision logic 226 and a housing of the estimate generation logic 228. For example, the storage device 902 may be remote from both the data provision logic 226 and the estimate generation logic 228 (e.g., in a cloud storage system).

FIG. 10 depicts an arrangement 1000 in which the breathing signal receipt logic 222, the locomotion signal receipt logic 224, the data provision logic 226, and the estimate generation logic 228 are all included in a common housing 1002 with a communication device 1004. Upon generation of the COPD severity estimate by the estimate generation logic 228, the communication device 1004 may be used to provide the COPD severity estimate to estimate notification logic 236 (not shown, but may be included in the housing 1002 or in a different housing).

Figure 11:
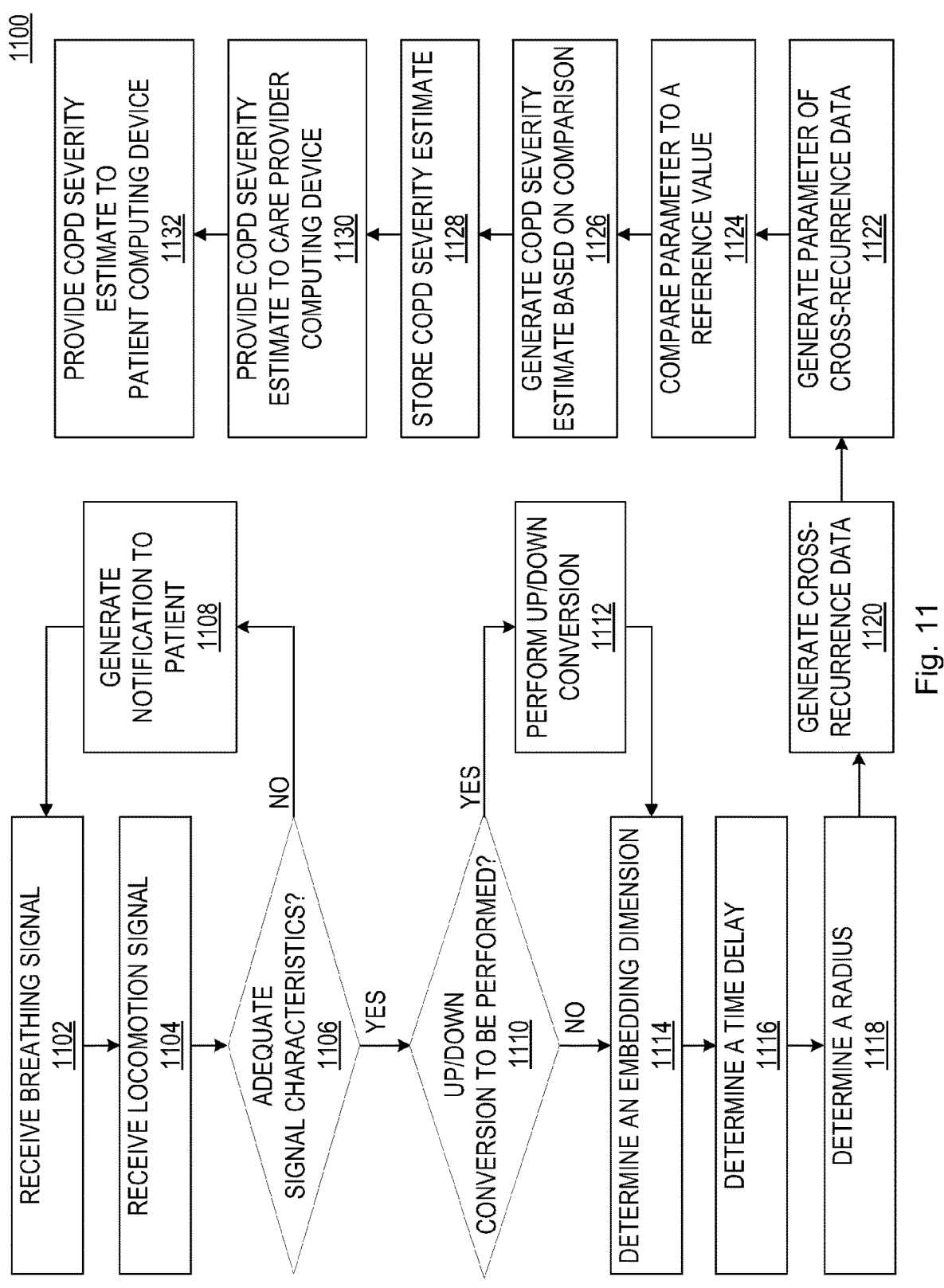
FIG. 11 is a flow diagram of an illustrative process for COPD severity estimation, in accordance with various embodiments.

FIG. 11 is a flow diagram of an illustrative process 1100 for COPD severity estimation, in accordance with various embodiments. While the operations of the process 1100 are arranged in a particular order in FIG. 11 and illustrated once each, in various embodiments, one or more of the operations may be repeated, omitted, or performed out of order. In particular, various operations of the process 1100, although illustrated as performed in a particular sequence for the sake of illustration, may be performed in parallel as suitable. Operations of the process 1100 may be described as performed by the COPD severity estimation system 200, as embodied in the computing system 100, for illustrative purposes, but the operations of the process 1100, including individual operations of the process 1100, may be performed by any suitably configured computing device or collection of computing devices. Any of the operations of the process 1100 may be performed in accordance with any of the embodiments of the computing system 100 and COPD severity estimation system 200 described herein.

At 1102, the COPD severity estimation system 200 (e.g., the breathing signal receipt logic 222) may receive a breathing signal. The breathing signal may be generated through the use of a breathing sensor (e.g., the breathing sensor 212). The breathing signal may be representative of breathing activity of a patient over a time interval.

At 1104, the COPD severity estimation system 200 (e.g., the locomotion signal receipt logic 224) may receive a locomotion signal. The locomotion signal may be generated through the use of a locomotion sensor (e.g., the locomotion sensor 214). The locomotion signal may be representative of locomotive activity of the patient over the time interval. In some embodiments, the operations discussed with reference to 1102 and 1104 may be performed at least partially in parallel.

At 1106, the COPD severity estimation system 200 (e.g., the breathing signal receipt logic 222, the locomotion signal receipt logic 224, and/or the data provision logic 226) may determine whether the received breathing and locomotion signals have adequate characteristics for use in generating a COPD severity estimate. For example, if an inadequate number of samples of sufficient locomotive activity have been received, the breathing and/or locomotion sensor is improperly positioned or malfunctioning, or the signal(s) is contaminated with external noise, the received breathing and locomotion signals may not be adequate for use in generating a COPD severity estimate.

If the COPD severity estimation system 200 determines at 1106 that the received breathing and locomotion signals are not adequate for use in generating a COPD severity estimate, the COPD severity estimation system 200 may proceed to 1108 and generate a notification to the patient. This notification may include instructions to the patient (e.g., "Please walk at a normal pace for 45 seconds"), describe the detected error condition, or simply notify the patient that a COPD severity estimate will not be generated. The COPD severity estimation system 200 may then return to 1102.

If the COPD severity estimation system 200 determines at 1106 that the received breathing and locomotion signals are adequate for use in generating a COPD severity estimate, the COPD severity estimation system 200 may proceed to 1110 and determine whether one or both of the breathing and locomotion signals should be up-converted and/or down-converted so that the two signals are sampled at consistent times. Up- and/or down-conversion may be usefully performed when the breathing signal and the locomotion signal are sampled at different rates.

If the COPD severity estimation system 200 determines at 1110 that up-/down-conversion is to be performed, the COPD severity estimation system 200 may proceed to 1112 and perform up-/down-conversion. For example, in some embodiments, the breathing signal may be a discrete-time signal having a first sampling rate, and the locomotion signal may be a discrete-time signal having a second sampling rate different from the first sampling rate. If the first sampling rate is higher than the second sampling rate, the COPD severity estimation system 200 (e.g., the breathing signal receipt logic 222) may down-convert the breathing signal to match the second sampling rate (e.g., by interpolating the breathing signal and resampling the interpolated breathing signal at the second sampling rate). Alternatively, if the first sampling rate is higher than the second sampling rate, the COPD severity estimation system 200 (e.g., the locomotion signal receipt logic 224) may up-convert the locomotion signal to match the first sampling rate (e.g., by interpolating the locomotion signal and resampling the locomotion signal at the first sampling rate). Analogous operations may be performed if the first sampling rate is less than the second sampling rate.

The COPD severity estimation system 200 (e.g., the estimate generation logic 228) may then proceed to 1114 and determine an embedding dimension for the breathing and locomotion signals. As noted above, the embedding dimension determines the size of the vector representation of the breathing and locomotion signals for cRQA. In some embodiments, the COPD severity estimation system 200 (e.g., the estimate generation logic 228) may utilize a false nearest neighbors algorithm to determine an appropriate embedding dimension. In other embodiments, any suitable known technique for determining an appropriate embedding dimension may be used. In some embodiments, a component of the computing system 100 or an external component may determine an appropriate embedding dimension in advance (e.g., by applying the false nearest neighbors or other algorithm to data similar to the breathing and locomotion data), and the value of this embedding dimension may be stored in the storage device 206 for access by the estimate generation logic 228; in such embodiments, the operations of 1114 may not be performed in the illustrated order, or may not be performed by the COPD estimation system 200 at all. In some embodiments, an embedding dimension may be determined for each COPD severity estimate, while in some embodiments, a same embedding dimension may be used for all COPD severity estimates. In some embodiments, the embedding dimension may be 5.

The COPD severity estimation system 200 (e.g., the estimate generation logic 228) may then proceed to 1116 and determine a time delay for the embedding of the breathing and locomotion signals. As noted above, the time delay determines the spacing between the samples of the signals that make up the vector representation of the breathing and locomotion signals for cRQA. In some embodiments, the COPD severity estimation system 200 (e.g., the estimate generation logic 228) may utilize an average mutual information algorithm to determine an appropriate time delay. In other embodiments, any suitable known technique for determining an appropriate time delay may be used. In some embodiments, a component of the computing system 100 or an external component may determine an appropriate time delay in advance (e.g., by applying the average mutual information or other algorithm to data similar to the breathing and locomotion data), and the value of this time delay may be stored in the storage device 206 for access by the estimate generation logic 228; in such embodiments, the operations of 1116 may not be performed in the illustrated order, or may not be performed by the COPD severity estimation system 200 at all. In some embodiments, a time delay may be determined for each COPD severity estimate, while in some embodiments, a same time delay may be used for all COPD severity estimates. In some embodiments, the time delay may represent 150-350 milliseconds of data. When data is sampled at 60 Hz, for example, this may represent approximately 10-20 samples.

The COPD severity estimation system 200 (e.g., the estimate generation logic 228) may then proceed to 1118 and determine a radius for the embedding of the breathing and locomotion signals. As noted above, the radius determines how close a breathing and a locomotion vector have to be to be counted as a point for cRQA. In some embodiments, the COPD severity estimation system 200 (e.g., the estimate generation logic 228) may set the radius in order to achieve a particular percent recurrence. For example, the radius may be set to achieve a 2% recurrence. In other embodiments, the percent recurrence may be selected to be a percentage between 1% and 5% (as may be appropriate for behavioral data to achieve adequate sensitivity). In other embodiments, any suitable known technique for determining an appropriate radius may be used. In some embodiments, a component of the computing system 100 or an external component may determine an appropriate radius in advance (e.g., by using data similar to the breathing and locomotion data), and the value of this radius may be stored in the storage device 206 for access by the estimate generation logic 228; in such embodiments, the operations of 1118 may not be performed in the illustrated order, or may not be performed by the COPD severity estimation system 200 at all. In some embodiments, a radius may be determined for each COPD severity estimate, while in some embodiments, a same radius may be used for all COPD severity estimates.

The COPD severity estimation system 200 (e.g., the estimate generation logic 228) may then proceed to 1120 and may generate cross-recurrence data comparing the breathing and locomotion data. This cross-recurrence data may be generated in accordance with the expressions above, using any suitable computational techniques.

At 1122, the COPD severity estimation system 200 (e.g., the estimate generation logic 228) may generate one or more parameters of the cross-recurrence data generated at 1120.

The parameter(s) generated at 1122 may include any of the parameters discussed above, such as percent determinism, maximum diagonal line length, mean diagonal line length, or any other suitable parameter.

At 1124, the COPD severity estimation system 200 (e.g., the estimate generation logic 228) may compare the parameter(s) generated at 1122 to corresponding reference value(s). The reference value may take the form of any of the reference values discussed above, and the comparison may take the form of any of the comparisons discussed above.

At 1126, the COPD severity estimation system 200 (e.g., the estimate generation logic 228) may generate a COPD severity estimate based on the comparison. This estimate may take the form of any of the estimates discussed above.

At 1128, the COPD severity estimation system 200 (e.g., the estimate generation logic 228) may store the COPD severity estimate generated at 1126 in the storage device 206. The storage of the COPD severity estimate may be substantially permanent or may be temporary (e.g., in a buffer).

At 1130, the COPD severity estimation system 200 (e.g., the estimate notification logic 236) may provide the COPD severity estimate to a care provider computing device (e.g., the care provider computing device 110). The COPD severity estimate may be displayed on a display device of the care provider computing device (e.g., the display device 218) and/or stored on the care provider computing device.

At 1132, the COPD severity estimation system 200 (e.g., the estimate notification logic 236) may provide the COPD severity estimate to a patient computing device (e.g., the wearable computing device 102 and/or the patient personal computing device 104). The COPD severity estimate may be displayed on a display device of the patient computing device (e.g., the display device 218) and/or stored on the patient computing device.

Any of the signals, data, parameters, estimates, or other information used by the COPD severity estimation system 200 during its operation may be stored in the storage device 206 is any suitable data structure. For example, FIG. 13 is a representation of an illustrative data structure 1300 for storing data generated and/or used by the COPD severity estimation system 200, in accordance with various embodiments. The entries and fields of the data structure 1300 are simply illustrative, and various ones of the fields may be omitted or modified, or additional fields included, as suitable. Additionally, not all fields may be populated with data for each entry.

The data structure 1300 may include an entry for each COPD severity estimate for the patient; in FIG. 13, three example entries 1330, 1332, and 1334 are shown. The data structure 1300 may include a date/time field 1302 that may be used to store a date and/or time at which a COPD severity estimate for an entry was generated or a date and/or time at which the data used for a COPD severity estimate for the entry was collected. The data structure 1300 may include an embedding dimension field 1304 that may be used to store the embedding dimension associated with the entry. The data structure 1300 may include a time delay field 1306 that may be used to store a time delay for embedding associated with the entry. The data structure 1300 may include a radius field 1308 that may be used to store a cRQA radius associated with the entry. The data structure 1300 may include a percent recurrence field 1310 that may be used to store a percent recurrence associated with the entry. The data structure 1300 may include a percent determinism field 1312 that may be used to store a percent determinism associated with the entry. The data structure 1300 may include an entropy field

1314 that may be used to store an entropy associated with the entry. The data structure 1300 may include a maximum (diagonal) line length field 1316 that may be used to store a maximum diagonal line length associated with the entry. The data structure 1300 may include a mean (diagonal) line length field 1318 that may be used to store a mean diagonal line length associated with the entry.

The data structure 1300 may include a frequency ratio field 1320 that may be used to store a frequency ratio associated with the entry. The data structure 1300 may include a maximum cross-correlation field 1322 that may be used to store a maximum value of a cross-correlation associated with the entry. The data structure 1300 may include a BODE index field 1324 that may be used to store a BODE index associated with the entry (e.g., a BODE index determined at approximately the same time as the cRQA analysis associated with the entry). The data structure 1300 may include a GOLD classification field 1326 that may be used to store a GOLD classification associated with the entry (e.g., a GOLD classification determined at approximately the same time as the cRQA analysis associated with the entry). The data structure 1300 may include an EXACT score field 1328 that may be used to store an EXACT score associated with the entry (e.g., an EXACT score determined at approximately the same time as the cRQA analysis associated with the entry).

As noted above, the estimate notification logic 236 may cause the display of a visual representation of a COPD severity estimate (e.g., on the display device 218). FIG. 14 is a representation of an illustrative display 1400 for displaying data generated and/or used by the COPD severity estimation system 200, in accordance with various embodiments. The display 1400 may include a cRQA analysis section 1402, which may include plots or other ways of displaying current (and, optionally, past) cRQA parameters associated with the patient. For example, the section 1402 of FIG. 14 includes a plot 1410 depicting a patient's generated values of percent determinism 1420 over time. The plot 1410 also indicates a reference value 1430 against which the values of percent determinism 1420 may be compared (e.g., as discussed above with reference to the estimate generation logic 228). The section 1402 of FIG. 14 includes a plot 1412 depicting a patient's generated values of percent recurrence 1422 over time. The plot 1412 also indicates a reference value 1432 against which the values of percent recurrence 1422 may be compared (e.g., as discussed above with reference to the estimate generation logic 228). The section 1402 of FIG. 14 includes a plot 1414 depicting a patient's generated values of mean diagonal line length 1424 over time. The plot 1414 also indicates a reference value 1434 against which the values of mean diagonal line length 1424 may be compared (e.g., as discussed above with reference to the estimate generation logic 228). In some embodiments, the section 1402 of FIG. 14 may include a short summary of the COPD severity estimation (e.g., "elevated" or "not elevated") instead of or in addition to the plots 1410, 1412, and 1414.

The display 1400 may also include a section 1408 for other COPD indicators, such as the BODE index (shown along with a date of generation associated with the particular BODE index), the GOLD class (shown along with a date of generation associated with the particular GOLD class), and the EXACT score (shown along with a date of generation associated with the particular EXACT score). The display 1400 may also include a section 1404 for patient information and a section 1406 for patient notes. As shown in FIG. 14, the patent information section 1404 may provide one or more indicators of the patient's activity level (e.g., number of steps per day, number of bouts of movement per day, percentage of day active, etc.). This information may be provided (in raw or processed form) by the locomotion signal receipt logic 224 or other sensors. Information about the patient's physical activity may be relevant to the care provider, and may be displayed as a graph or other chart over time as discussed above with reference to section 1402.

Experimental Results Regarding the Effect of Voluntary and Involuntary Breathing Rhythms on Locomotor Respiratory Coupling in the Context of Estimation of COPD Severity Various embodiments of the COPD severity estimation system 200 (e.g., as instantiated in the computing system 100) may be used in the study setting discussed below.

Summary: A study was conducted to investigate the effect of voluntary and involuntary abnormal breathing rhythms on the ability to couple the locomotor and respiratory systems. To quantify coupling, three tools were examined: frequency ratio, cross-correlation, and cRQA. In Experiment 1, twelve young healthy controls were asked to walk at a self-selected speed and breathe either at their normal pace, a faster pace, or a slower pace to investigate the effect of voluntarily altering breathing rhythm on locomotor respiratory coupling. Further, to investigate the effect of mismatching frequencies on coupling, the same subjects were asked to walk at speeds that were +20% or −20% of their self-selected walking speed but were instructed to either breathe slower than normal or faster than normal. Position data from the right trochanter (sampled at 60 Hertz), right heel (sampled at 60 Hertz), and breathing data (18 Hertz) were recorded for three minutes and subjected to data reduction. Breathing data was interpolated to 60 Hertz and all three data sets were normalized, rendering them unitless. A one-minute segment (3600 data points) was then selected for analysis for each subject. The most common frequency ratio, maximum cross-correlation, cRQA radius, percent recurrence, percent determinism, entropy, maximum line length, and mean line length were calculated. Even though stepping frequency was constrained to the speed of the treadmill, the healthy young subjects were able to couple locomotion to the respiratory rhythm when walking at their self-selected pace. This indicates that bidirectionality exists between the two systems and that this could be due to a neural/central command driving mechanism. By voluntarily altering their breathing rhythm, the respiratory brain centers were able to coordinate this information regarding the abnormal rhythm with their locomotor centers, allowing these subjects to couple under abnormal breathing conditions without any problems. When subjects were instructed to walk at a slow speed and breathe at a faster rate than normal, the subjects coupled the two rhythms less often and for shorter lengths of time as compared with when they were asked to walk at a slow speed and breathe slowly. In Experiment 2, six patients with COPD and fourteen age-matched controls were tested to investigate the effect of involuntary, abnormal breathing patterns on locomotor respiratory coupling. As discussed above, patients with COPD represent a population that has abnormal breathing patterns due to the pathophysiology of the disease. Patients with COPD and age-matched controls were asked to walk on a treadmill for four minutes under a self-selected walking speed and speeds+/−10% and +/−20% of their self-selected speed. No instructions regarding breathing were given. Data treatment and extraction of the dependent variables were the same as in Experiment 1. Comparison of mean dependent variables was conducted between the two groups and between the five speeds. Additionally, to investigate the effect of age and disease on the dependent variables, patients with COPD, age-matched controls, and the healthy young adults (from Experiment 1) were compared during their self-selected walking paces. Patients with COPD demonstrated a stricter range of frequency ratios that represented more rigid and less complex coupling as well as demonstrating stronger temporal similarity and increased coupling strength. When patients with COPD were compared with young adults and age-matched controls at their self-selected speeds, patients with COPD demonstrated an increased number of times in which they coupled the two rhythms, and for different lengths of time, as compared with their age-matched controls. This suggests that patients with COPD demonstrate more rigid coupling, due to the abnormal breathing rhythms. Changes in speed elicited changes in cRQA percent determinism, entropy, maximum line length, and mean line length in both groups, demonstrating that coupling is in fact altered under different task demands. However, the majority of the adaptations to speed were elicited during the slowest walking speed, and coupling was tightest in patients with COPD. Furthermore, a significant interaction for entropy was found in which patients with COPD were able to couple the two rhythms together more often and for different lengths of time. From a dynamic systems theory point of view, preferred performance in certain situations can be along a continuum of very rigid to very random and patients with COPD appear to demonstrate a very rigid coupling pattern. They prefer a 1:1 or 2:1 coupling that is much tighter than their healthy counterparts, and it is very difficult for them to phase-shift into another behavioral state and a stronger coupling from cRQA results. Rehabilitation programs should be designed to utilize control parameters to try to move the behavioral attractor from this very rigid pattern into something more complex (e.g., 3:1 or 4:1). The cRQA tools studied in these experiments appear to be effective in estimating locomotor respiratory coupling and proved to be more sensitive to changes in condition, group, and speed relative to the most common frequency ratio and cross-correlation. These two combined experiments demonstrated that changes in voluntary and involuntary abnormal breathing rhythms can alter one's ability to couple his or her locomotor and respiratory system, and more so in involuntary abnormalities than voluntary abnormalities. Healthy young adults demonstrate more flexibility, and this may have assisted them in adapting to the task demands. Furthermore, involuntary abnormal breathing patterns have a significant influence on coupling.

Introduction: In some biological systems, there may be a mutual attraction between two rhythms, and eventually the rhythms will entrain to the intrinsic rate of the other. This natural desire to entrain is resisted by the rhythms' own intrinsic rates and may result in complex coupling between the two rhythms. In line with this concept of entrainment, coupling between movement and respiration in mammals, including humans, may be present. Coupling between locomotion and respiration can be lost through disease, for instance, in Parkinson's disease.

Three main hypotheses have been proposed that would elicit such entrainment between locomotion and respiration: 1) chemoreception, 2) central command, and 3) peripheral feedback mechanisms. The chemoreception hypothesis stipulates that carotid body receptors detect gas partial pressure changes or other metabolic changes and/or the effective value of oxygen concentration in the lungs influence respiratory control centers. The central command hypothesis specifies that motor efferent projections either directly or indirectly connect to respiratory centers in the brain stem. The peripheral feedback mechanisms hypothesis suggests that somatic afferents from the skeletal muscle tissue project to the respiratory control centers as well, including influences such as forces acting on the trunk and thorax and flexion and extension movements of the axial skeleton. Existing evidence in humans seems to lean toward a neural-mechanical influence more so than a metabolic influence on coupling between locomotion and respiration, and some researchers believe that the coupling between the cardiac and locomotor systems elicits a strong influence on the coupling between respiration and locomotion. The majority of existing models for the locomotion-respiration relationship have been criticized as being overly simplistic given the complexity of the relationship between movement and respiration.

Coupling between two or more biorhythms could also be the result of bidirectional information processing. In humans, existing evidence suggests that locomotion drives respiration, respiration drives locomotion, and that their influence on each other is bidirectional. However, it is not understood how voluntary control of respiration influences the entrainment to locomotion. Respiration is one of the few autonomic processes of the human body that can also be controlled through voluntary control. Asking an individual to force his or her natural breathing outside of a comfortable rhythm (i.e., breathe slower or faster than normal) without instructions regarding step pattern may in fact cause a disruption in the entrainment to locomotion. Furthermore, perturbations or speed changes that alter movement frequency may influence breathing frequency. Therefore, constraining stepping frequency to a rate that is outside of a person's comfortable pace may also exert alterations in breathing entrainment. Previous research has not adequately explored cognitive control of breathing and abnormal frequency of walking.

Although not of voluntary control, it was previously unknown how involuntary, abnormal breathing rhythms affect entrainment. That is, how does having poor respiration or abnormal lung function affect entrainment? As discussed above, COPD is defined in terms of fixed airflow limitation. Patients with COPD and asthmatics with severe airway obstruction demonstrate abnormal breathing rhythms, but previous research has demonstrated a not-significant loss in long-term dependence in COPD patients from one breath to the next (i.e., Brownian motion) as compared with asthmatics and age-matched controls (i.e., pink noise). A loss in memory or long-term dependence of breathing may be associated with aging, but it appears that the pathophysiology of COPD may cause even more degradation to long-term dependencies. Few studies have attempted to understand the role of altered breathing rhythms on entrainment, and those that have done something similar have done so by having healthy individuals breathe to an external stimulus or by instructing them to maintain a certain breath to movement frequency.

An aspect of coupling may be a resistance to perturbations. The most common way to test coordination is to perturb one or both of the rhythms. Speed is commonly used as a rehabilitation parameter. Typically in rehabilitation settings, patients are asked to increase or decrease walking speed.

The results of this study included improved approaches to quantifying and classifying the effect of 1) voluntarily altering breathing rhythms outside of one's preferred frequency on entrainment with locomotion and 2) an involuntary, abnormal breathing rhythm on locomotor respiratory coupling. In addition, the effect of speed perturbations was explored.

Experiment 1 included an investigation of the effects of voluntarily breathing slower or faster than normal under self-selected walking speeds, as well as faster and slower walking speeds, in healthy young adults.

Experiment 2 included an investigation of the effects of an involuntary, abnormal breathing rhythm on locomotor respiratory coupling. Patients with COPD were compared with age-matched controls.

In both experiments, coupling was investigated using several tools. First, an integer ratio was calculated for the number of heel strikes per breath. This technique has been used extensively within the locomotor respiratory coupling literature, and a 2:1 ratio was previously found to be the dominant ratio. Lower-order frequency ratios, such as a 1:1 or 2:1, have been interpreted as a "simple ratio" as opposed to a higher-order ratio, such as 3:1 or 3:2.

Cross-correlation was utilized to measure the degree of temporal similarity between two rhythms. Cross-correlation has been utilized previously to describe locomotor respiratory coupling.

Additionally, cRQA techniques were utilized to quantify coupling between the walking and breathing rhythms. As discussed above, unlike standard RQA, cRQA explores recurrences between two different data sets, rather than within one data set.

Experiment 1: Twelve healthy young adults ages 19 to 35 years old were recruited through word of mouth and participated in this study (Table 1). Subjects were included if they did not have a history of injury and/or disease that would affect their gait walking patterns.

Upon inclusion in the study, patients were asked to change into a form-fitting suit, and under the suit, they were asked to wear a wireless physiological monitor (BIOHARNESS 3; Zephyr Technology Corp., Annapolis, MD; 18 Hz) against their skin to measure chest movement (as a surrogate for breathing). The metallic material on the physiological monitor's harness was dampened with water before placing the straps against the skin. The investigator confirmed that the straps and harness would not slip during data collection, ensuring a tight fit. Reflective markers were placed on anatomical locations, bilaterally, according to a modified Helen Hayes marker set. Subjects were asked to choose a self-selected speed on the treadmill. A self-selected pace was defined for the subjects as a comfortable walking speed, a pace that they would walk from their vehicle into the building or across the campus. In order to choose their speed, subjects were allowed to control the speed of the treadmill, and once they mentioned they felt they had reached a comfortable walking speed, the investigator increased the speed slightly. The speed was increased until the subject reported that the treadmill was moving faster than they were comfortable walking. The treadmill was then slowed again in phases until subjects mentioned that it felt too slow. These steps were repeated until a speed was found that was a comfortable walking pace for the subject. This process took anywhere from five to ten minutes for most subjects.

Once a subject's comfortable walking speed was chosen, the subject was allowed to rest for a minimum of one minute. After the subject was well rested, he or she returned to the treadmill to complete three and a half minutes of walking on the treadmill at the self-selected pace with no particular instructions regarding the subject's breathing pace (NORM SELF). Three dimensional marker positions from the last three minutes of walking were recorded with a high-speed motion capture system (Motion Analysis Corp., Santa Rosa, CA; 60 Hz). Breathing data from the physiological monitor was synchronized and recorded simultaneously with the three dimensional marker positions via a multifunction data acquisition USB (NI USB-6218; National Instruments Corp., Austin, TX) and a custom LabVIEW program (National Instruments Corp., Austin, TX).

After completion of the NORM SELF condition, subjects were then asked to walk for three and a half minutes under six more, randomly assigned, conditions. The conditions were:

Walking at their self-selected pace but were asked to breathe slower than they are accustomed to doing (SLOW SELF). These same breathing instructions were given for each of the other two SLOW conditions.

Walking at their self-selected pace but were asked to breathe faster than they normally would (FAST SELF). The instructions were to breathe at a faster rate but not to the point in which they felt that they were hyperventilating or not getting enough air. These same breathing instructions were given for each of the other two FAST conditions as well.

Walking at a speed+20% faster than their self-selected pace and breathing slower than normal (SLOW+20%).

Walking at a speed+20% faster than their self-selected pace and breathing faster than normal (FAST+20%).

Walking at a speed−20% slower than their self-selected pace and breathing slower than normal (SLOW−20%).

Walking at a speed−20% slower than their self-selected pace and breathing faster than normal (FAST−20%).

A minimum of one minute of rest was given between each trial to prevent the onset of fatigue.

Each three-minute time series of marker position data and/or breathing data was then subjected to data reduction to calculate the dependent variables. A custom Matlab program (Matlab 2007, Mathworks, Inc., Concord, MA) was written to load the sagittal right trochanter data and right heel data along with the breathing data from each condition. The trochanter data set was chosen as it represents of the global vertical movement of the body during walking and was used in analysis of cross-correlation and cRQA. The coupling of breathing with the sacral or heel marker were also explored, but the movements of these markers were either too complex or too much off plane to truly represent the actual motion of walking. The heel data set was utilized to calculate frequency ratio.

Figure 15:
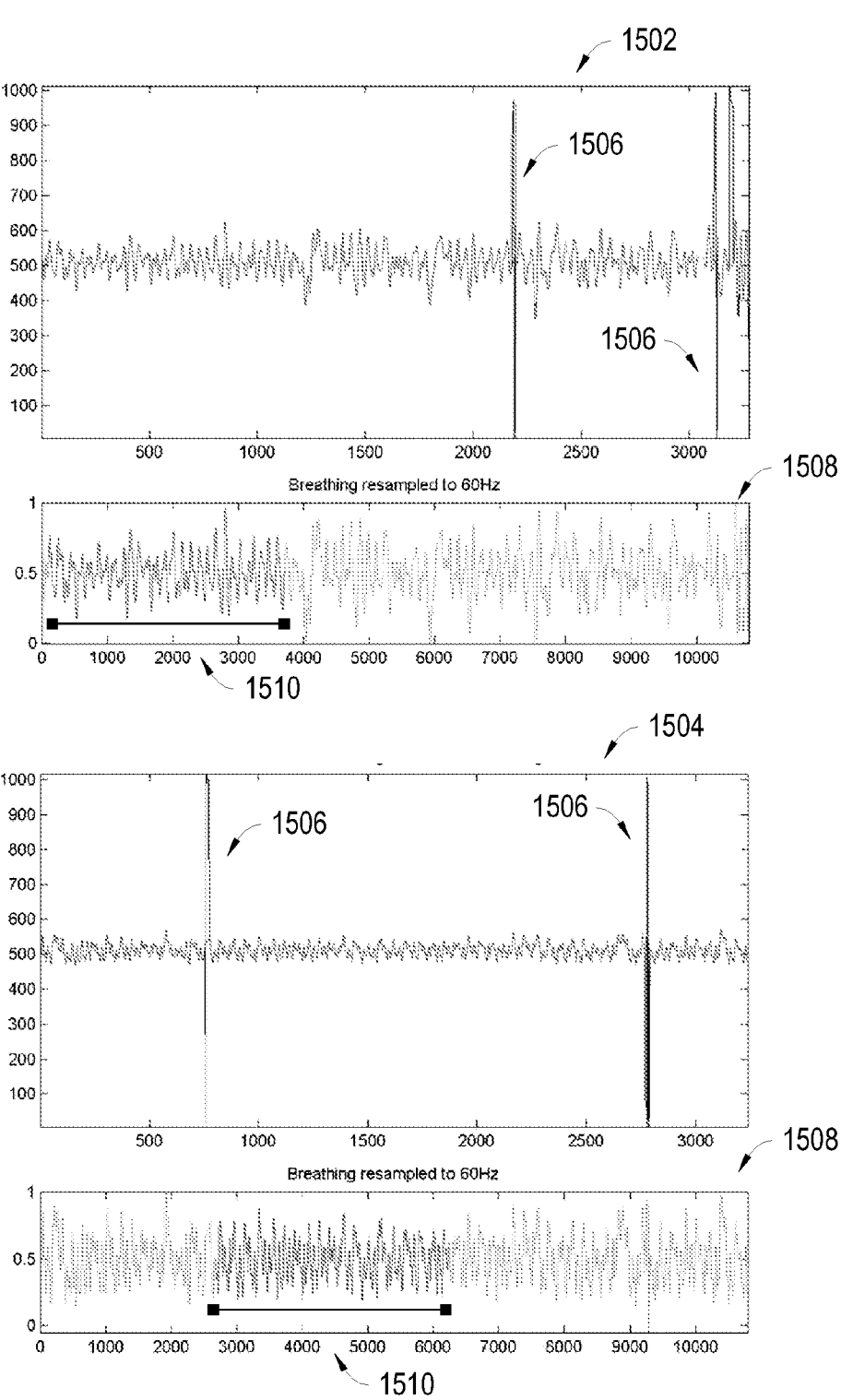
FIG. 15 includes graphs from the COPD severity estimation study illustrating representative segment selection for two healthy young adults walking at a self-selected pace with no breathing instructions.

Breathing data were plotted for spikes and outliers. Spikes and data points greater than three standard deviations from the mean were removed. A cubic spline was used to interpolate the removed data points. The breathing data were then interpolated to 60 Hz using a cubic spline. Breathing, trochanter, and heel data were normalized to the unit vector and, hence, rendered all data sets unitless. Finally, a one-minute segment of the trial was selected for analysis (3600 data points). FIG. 15 includes graphs 1502 and 1504 illustrating representative segment selection for two healthy young adults, respectively, from the NORM SELF condition. Selected one-minute segments from the data sets were used for data analysis. All locomotion data were visually inspected and no spikes or outliers were found in the data of FIG. 15. On the other hand, the respiration data were prone to spikes and outliers 1506. The normalized data, with the spikes and outliers 1506 removed, were plotted (1508) and a 3600 data point segment of the entire trial for each participant was selected for analysis (1510). Segments were selected as the first 3600-length segment available that had minimal treatment as far as removing outliers and spikes. Due to the nature of the wireless technology and sometimes due to the metallic material on the physiological monitor's harness not being wet enough, the breathing signal experienced some dropout for some conditions. Almost all trials had a minimum of 3600 data points that were not corrupted by spikes. The 3600 data points that were chosen for analysis belonged to the first available one-minute segment in the time series (as discussed above with reference to FIG. 15). Therefore, for a completely uncorrupted file, the first 3600 points were used.

Figure 16:
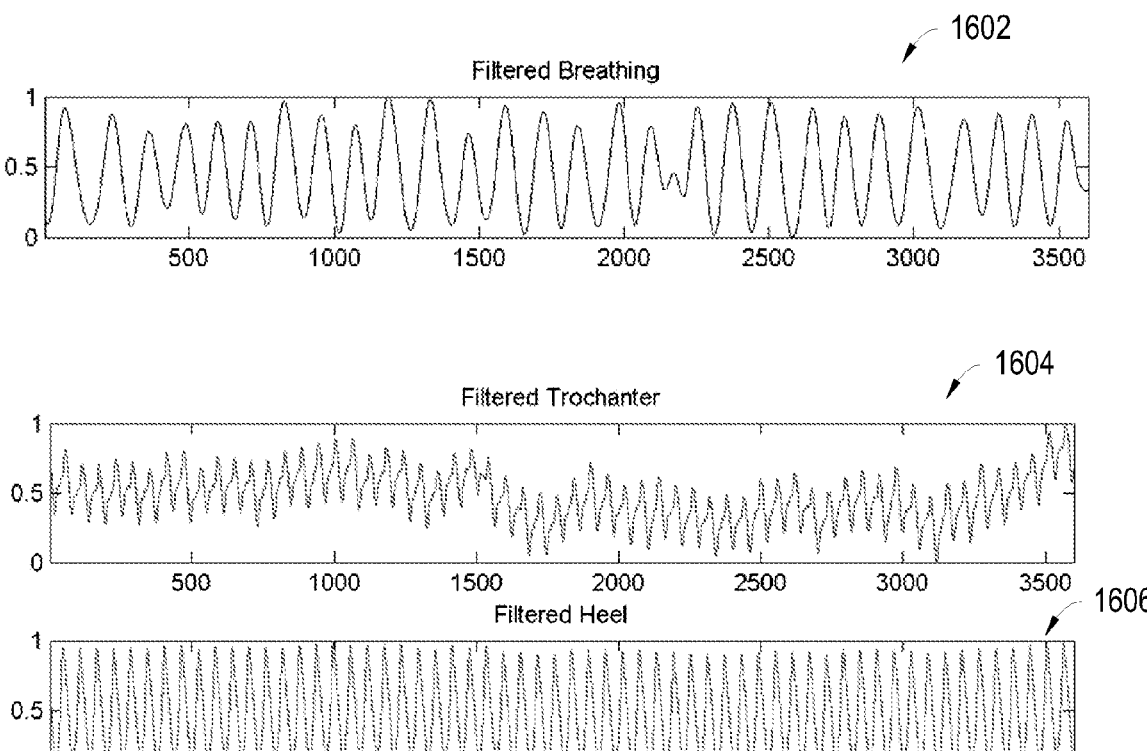
FIG. 16 includes graphs from the COPD severity estimation study illustrating filtered breathing and locomotion data from a representative healthy young adult for one minute of walking at a self-selected pace with no breathing instructions.

The same selected segment of breathing, trochanter, and heel data were then filtered and subjected to the following analysis for the calculation of dependent variables: frequency ratio, cross-correlation, and cRQA. The breathing data was filtered using a 10th order Butterworth filter at 0.5 Hz, and the trochanter and heel data sets were filtered using a 10th order Butterworth filter at 10 Hz. FIG. 16 includes graphs illustrating filtered breathing 1602 and locomotion (marker position at trochanter 1604 and heel 1606) data from a representative healthy young adult for one minute of walking during the NORM SELF condition. All data were normalized between 0 and 1. Breathing data were filtered using a cutoff frequency of 0.5 Hz, and all three of the marker position data sets were filtered using a cutoff frequency of 10 Hz.

A custom Matlab program was utilized to calculate the ratio of heel strikes to breaths. The presence of a heel strike was calculated as the local maximum of the derivative of the heel position data. Using existing methods, the discrete relative phase was calculated between the breathing data and the timing of heel strikes. Based on the discrete relative phase value, the number of heel strikes within a breath can be calculated. For instance, if the discrete relative phase is between 0° and 360°, there was one heel strike. However, if the returned value is between 360° and 720°, there were two heel strikes, and so forth.

For each breath taken during the one-minute data segment, the number of heel strikes was calculated. From there, the ratios (e.g., 1:1, 2:1, . . . , 11:1) were counted for each trial. The most utilized ratio was reported in addition to the percentage of that ratio being used. If more than one ratio was found to be the most commonly used, visual inspection was performed to see which ratio was repeated within the most consecutive breaths. This would represent a stronger coupling to that ratio, and therefore that was the ratio defined as the most common. Lastly, the total number of breaths and total number of heel strikes was recorded to confirm that the subjects followed instructions regarding the breathing rate and that they adapted to the speed alterations of the treadmill.

Using the Matlab function crosscorr, the breathing and trochanter data sets were used to determine the maximum cross-correlation value. Cross-correlation may be calculated as discussed above. Strengths of correlations were defined as follows: ±1.00 to 0.80=very strong; ±0.79 to 0.60=strong; ±0.59 to 0.40=moderate; ±0.39 to 0.20=weak; ±0.19 to 0=no relationship.

In order to perform cRQA, all time signals underwent analysis for time delay and embedding dimension. In order to find the time delay, the average mutual information algorithm was used. Average mutual information was run for each trial, providing a time delay specific for that trial. The mean and median time delays were then calculated for each condition. After inspecting the range of time delays for each condition, the mean time delay was chosen for all trials within that condition. The average time delays ranged from 12 to 16 for all conditions. Embedding dimension was determined using the false nearest neighbor algorithm. Again, embedding dimensions were inspected for each condition. Overall, the majority of all trials elicited an embedding dimension of five. Specifically, the range of embedding dimensions was from 5 to 7 with over 90% of all trials requiring an embedding dimension of 5. All trials were unfolded into 5 dimensions.

Using custom Matlab codes, cRQA was performed on the breathing and trochanter data. Using the input values of the time delay and embedding dimension, all attractors were unfolded into their appropriate state space, creating new time-delay vectors. The Euclidean distance between each data point in each vector was then calculated and stored into a matrix. The distances were rescaled to maximum distance.

Figure 17:
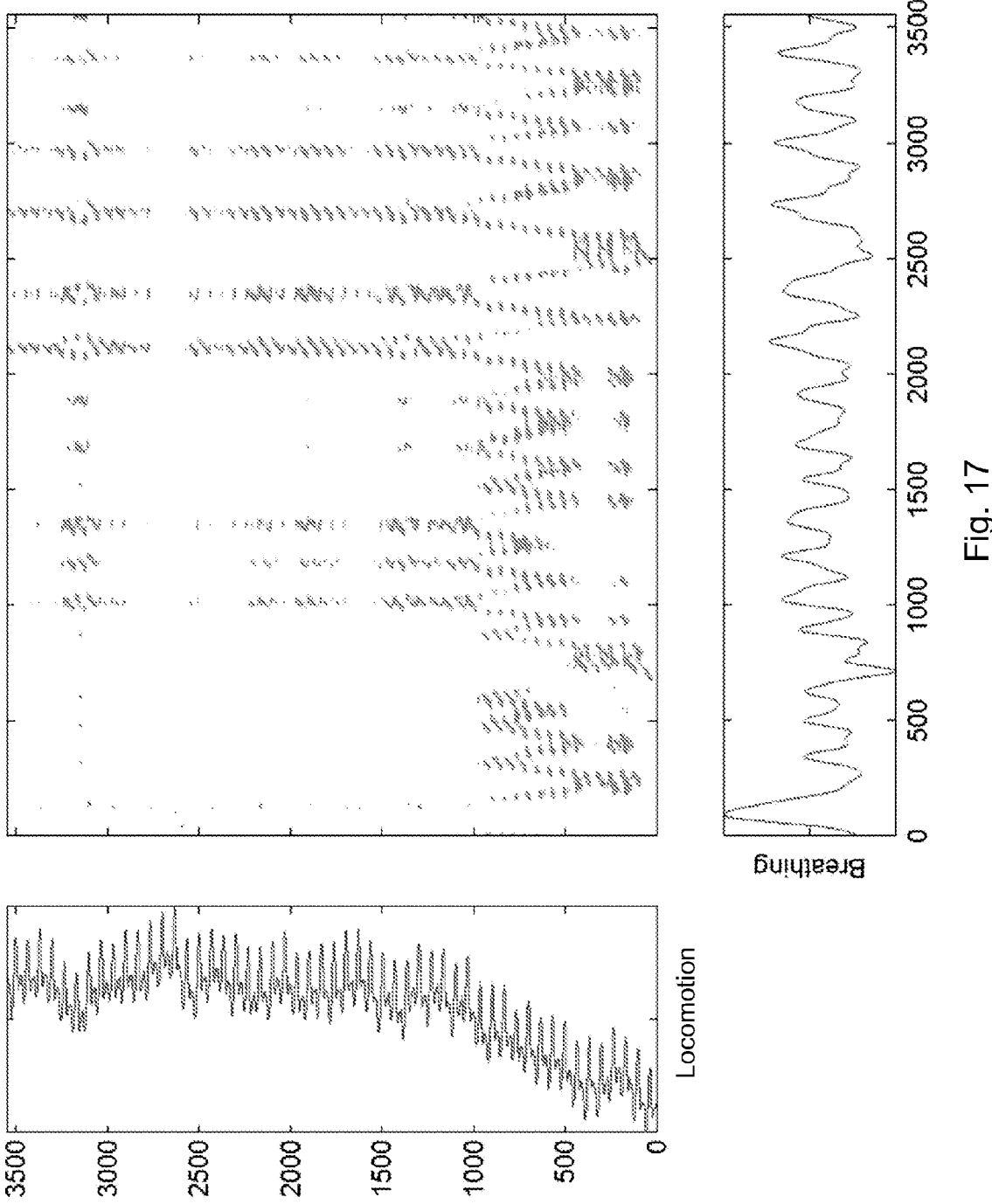
FIGS. 17-19 are recurrence plots of breathing and locomotion data for various subjects, along with the associated time series, in the COPD severity estimation study.
Figure 18:
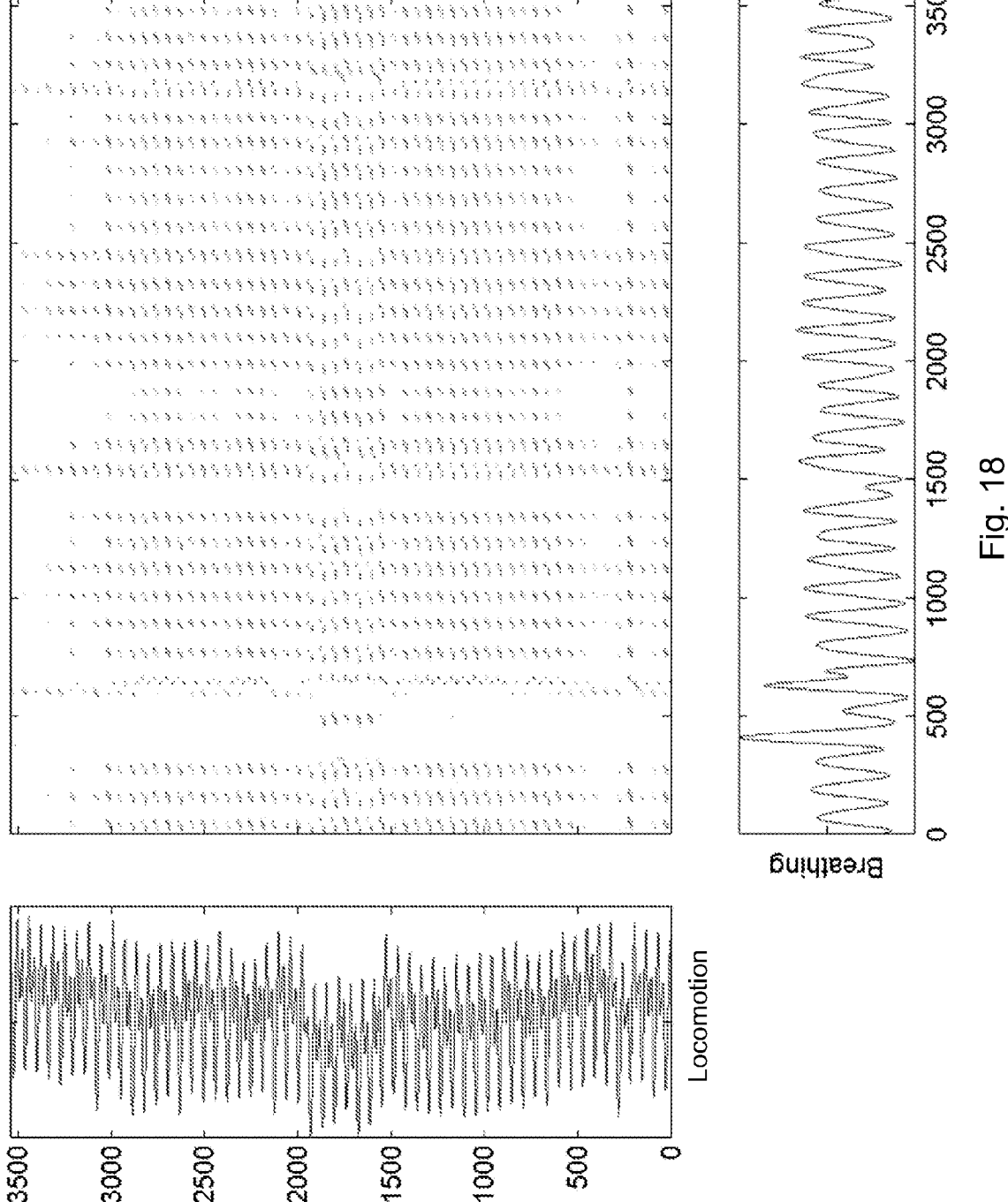
Figure 19:
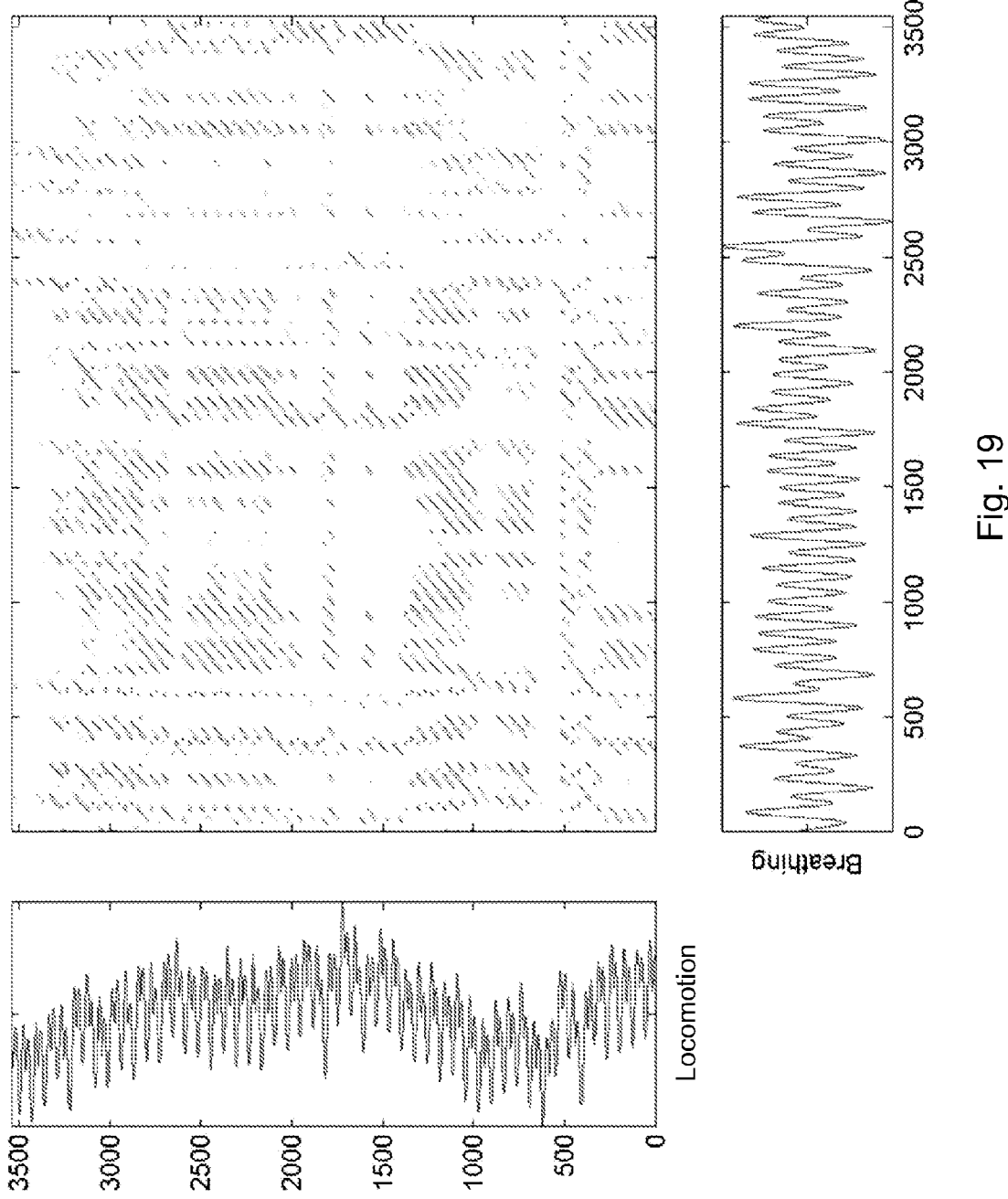

A recurrence plot was then derived from the distance matrix by the determined radius threshold. For example, FIG. 17 is a recurrence plot of breathing and locomotion (trochanter) data for a healthy young subject, FIG. 18 is a recurrence plot of analogous data for an older, age-matched control, and FIG. 19 is a recurrence plot of analogous data for a COPD patient, with each accompanied by the associated time series. As discussed above, distances within the distance matrix that were equal to or less than the radius were defined as recurrent at coordinates i and j. If the point i, j was determined as recurrent, then it appeared as a point on the recurrence plot. Therefore, the recurrence plot was a two-dimensional representation of points having a distance within the threshold of the radius. To set the radius for each trial, a radius was calculated that would provide for a 2% recurrence threshold. Percent recurrence, as discussed above, was defined as the number of recurrent points divided by the total number of possible recurrent points times 100. To achieve adequate sensitivity, the percent recurrence may be set at 1-5% for behavioral data. In FIGS. 17-19, the normalized and filtered breath time series is plotted along the X axis and the normalized and filtered locomotion series is plotted along the Y axis. All 3600 data points are unfolded into their state space and the Euclidean distance is calculated for each i, j coordinate. An i, j point on the recurrence plot that is indicated by a spot represents a Euclidean distance between the breathing and locomotion data that was equal to or less than the radius. Therefore, the recurrence plot is a two-dimensional representation of points having a distance is within the threshold of the radius. From this plot, the percent recurrence, entropy, maximum length of line, mean line length, and percent determinism can be calculated. Note that a graphical representation of the recurrence plot need not to be generated to generate the cRQA parameters discussed herein; instead, these parameters may be generated using some or all of the recurrence data that could also be used to generate a recurrence plot.

Analysis of the recurrence plot was then completed. A priori, it was determined that a minimum of six points in a row would be counted as a diagonal line. Six points was chosen because this represented 100 milliseconds of data, and any coupling happening under this time frame, for the purposes of this investigation, would be treated as spurious and/or due to reflex movement. The use of a minimum of 100 milliseconds of data in the definition of a diagonal line may also account for corticospinal latency. Once all lines longer than six consecutive points were counted, the length of the maximum line was determined and the mean length of the lines was calculated. The maximum length of a line may represent of the strength of the coupling between the attractors or rhythms. The mean line length may represent the average length of time that the two data sets are coupled.

The Shannon entropy was then calculated based on the distribution of diagonal line lengths, not for the time series, as discussed above.

Finally, percent determinism was calculated, as discussed above. In total, the dependent variables extracted from the cRQA analyses were radius, percent recurrence, the mean line length, maximum line length, the entropy of line lengths, and percent determinism.

The mean for each condition was calculated for most common frequency ratio, total number of breaths, total number of heel strikes, and maximum cross-correlation. In addition, the condition means from the dependent variables under the cRQA analysis were calculated. A repeated measures Analysis of Variance (ANOVA) was conducted to identify differences between the seven conditions (NORM SELF, SLOW SELF, FAST SELF, SLOW–20%, FAST–20%, SLOW+20%, FAST+20%) for the dependent variables listed above. Analysis was performed in SPSS (SPSS 20.0, IBM, Armonk, NY). Normality was examined for each dependent variable. The Greenhouse-Geisser correction was reported for all analyses that did not meet normality requirements. Tukey's post hoc comparisons were used if a significant main effect was found. The significance level was set at 0.05.

Results of Experiment 1: A significant main effect of condition was found for both total number of breaths ($F_{6,54}$:3.3, p=0.01) and total number of heel strikes ($F_{6,54}$: 10.1, p<0.001). This confirms that the subjects did in fact change their breathing patterns during the conditions as they were asked to do and adapted to changes in the treadmill speed. Through visual inspection, it can be seen that the most common frequency ratio was not altered even though the total number of breaths was different (Table 2). However, it is difficult to analyze this statistically, and therefore, the number of heel strikes from the most common ratio was analyzed and a significant main effect of condition was found ($F_{6,54}$:2.9, p=0.02). It was found that more heel strikes per breath were taken in the SLOW+20% condition as compared with the NORM SELF condition (p=0.01). In addition, the FAST–20% condition elicited significantly less heel strikes than the SLOW+20% condition (p=0.001).

The maximum cross-correlation elicited a significant main effect for condition ($F_{6,54}$:7.0, p=0.004) (Table 3). For the breath and the trochanter data sets, the maximum cross-correlation value was not significantly different between any of the self-selected pace conditions. However, differences were found for conditions involving changes in speed. The maximum cross-correlation value was significantly decreased in the SLOW+20% (p=0.01) and the FAST+20% (p=0.01) as compared with the NORM SELF condition. As compared with the SLOW SELF and FAST SELF, a significant decrease at SLOW+20% (p=0.001 and p=0.03, respectively) and FAST+20% (p=0.04 and p=0.04, respectively) was found. In addition, FAST–20% had a significantly increased maximum cross-correlation value as compared with SLOW SELF and FAST SELF as well (p=0.01 and p=0.03, respectively). Further, FAST–20% had also a significantly increased maximum cross-correlation value as compared with SLOW+20%, FAST+20% and SLOW–20% (p=0.003, p=0.01 and p=0.004, respectively).

For the breath and trochanter data sets, no main effect of condition was found for radius or percent recurrence (Table 4). On the other hand, a main effect of condition was found for percent determinism ($F_{6,54}$:2.8, p=0.02), entropy ($F_{6,54}$: 2.6, p=0.03), maximum line ($F_{6,54}$:5.9, p<0.001), and mean line ($F_{6,54}$:2.7, p=0.02). Percent determinism was significantly increased in the SLOW–20% as compared with SLOW SELF (p=0.03), FAST SELF (p=0.003), FAST+20% (p=0.02), and FAST–20% (p=0.02). Further, percent determinism was also significantly increased in FAST–20% as compared with FAST SELF (p=0.02). For entropy, SLOW+ 20% was significantly lower as compared with NORM SELF, FAST SELF, SLOW−20%, and FAST−20% (p=0.03, p=0.02, p=0.03, and p=0.02, respectively). For maximum line, SLOW−20% was significantly longer as compared with SLOW+20% (p=0.01). In addition, FAST−20% had a significantly longer maximum line as compared with NORM SELF (p=0.003), SLOW SELF (p=0.02), FAST SELF (p=0.01), and SLOW+20% (p=0.001). Both SLOW−20% and FAST−20% demonstrated significantly longer mean lines as compared with SLOW+20% (p=0.01 and p=0.03, respectively).

One purpose of Experiment 1 was to investigate the effect of voluntarily constricting breathing rates to either slower or faster than one's preferred rate on locomotor respiratory coupling. No significant differences were found between the NORM SELF, SLOW SELF, and/or FAST SELF conditions, indicating that voluntary alteration of breathing does not influence locomotor respiratory coupling. This provides support for bidirectionality between the two systems.

At least one previous study has indicated that using paced breathing could significantly increase coupling between running and breathing. The paced breathing was done by having the subjects breath to an acoustic signal that was triggered by the leg movement, thus constraining the subjects to breathe in pace with the leg movement. This explains why the use of paced breathing may have increased coupling. Another recent study demonstrated that using an auditory stimulus to synchronize breathing with pedaling during cycling worked better when subjects were instructed to pedal to the stimulus versus breathe in time with the stimulus. Even so, these authors did find that pacing the breathing rate to the auditory stimulus did have some effect on the coupling between breathing and cycling.

The investigation described above differs significantly from these two studies in that subjects were not constrained to breathe in time with their walking pace and/or breathe in time with a stimulus. In fact, the methodology was designed to discourage this type of strategy. Subjects were allowed to voluntarily control their breathing rate. The treadmill constricted the stepping frequency, and subjects were instructed to try to breathe either faster or slower than they normally would. This design was implemented to test the bidirectionality of respiratory action on the locomotor system and vice versa. The current results do support the hypothesis that bidirectionality exists between the two systems. Even though subjects walked on a treadmill, which inherently limits the variability allowed in stepping frequency, the healthy young subjects were able to still couple locomotion to the respiratory rhythm.

In addition, this provides further evidence for a neural/ central command driving hypothesis. First, brain stem controls to respiration have been clearly identified: the medial parabrachial/Kölliker Fuse complex in the dorsal pons regulates the phase switching between inspiration and expiration, and the pre-Bötzinger complex in the ventrolateral medulla functions as the respiratory rhythmogenesis hub. Second, through the advancement of brain imaging, it is known that supraspinal control is required during walking, not just a central pattern generator. In addition, in animal models, it has been shown that signals from the cervical and lumbar limb afferent inputs are conveyed to the brain stem respiratory centers, including the parabrachial/Kölliker Fuse complex. Additionally, the mesencephalic locomotor region, has been shown to have dorsal projections to the respiratory control centers and ventral projections to the reticulospinal tract (locomotion). Although these two findings have been identified in animals, there is translation to the human brain. Some researchers have shown that the organization of supraspinal locomotor centers identified in quadrupedal animals has been preserved with bipedal locomotion, providing further support for a neural control mechanism over locomotor respiratory coupling.

A secondary aim of this study was to investigate the effect of mismatching frequencies on coupling. For example, if subjects are walking faster, they may naturally want to breathe faster, but instructions were given to constrain their breathing to a slower rate. Partial support was found for the proposed hypothesis that alterations in speed that did not match the breathing frequency (e.g., SLOW+20% and FAST−20%) would cause a greater disruption to entrainment as opposed to the two matching frequencies (e.g., SLOW−20% and FAST+20%). The SLOW−20%, in which subjects walked slower and were instructed to breathe slowly, demonstrated significantly more patterns in line lengths and stronger coupling between the two rhythms, and the average length of time that the two data sets were coupled was longer as compared with the SLOW+20% condition. Subjectively, subjects commented that the SLOW+20% was "weird" and that they "had to really think about it." One subject commented that a "couple of times I forgot about it and had to come back to it." Still another mentioned that he had "conscious control, breathing would not match walking." It is possible that instructing subjects to breathe slowly while having them walk faster than their self-selected walking pace was the hardest condition presented to them.

If this was the case, it could be expected that having the subject walk slower than the self-selected pace, but breathe faster than normal, would also be difficult. Only one difference was found for the fast breathing mismatch conditions, the maximum cross-correlation value. In the FAST−20%, the maximum cross-correlation was found to be significantly greater than during the FAST+20%. This indicates that the strength of temporal similarity was coupled stronger during the mismatch condition; however, upon a closer look, the correlation values are 0.259 for FAST−20% and 0.113 for FAST+20%. Although significant, these correlation values are hardly meaningful. They are weak to no relationship, indicating that there may truly be no difference in coupling at the fastest walking pace. While preferred coupling may alter as speed, frequency, or workload is increased, this may not always be the case. There may be limits in which coupling can be achieved, and outside of these limits, movement no longer has an influence on the breathing rate.

The 20% increase in walking speed could also contribute to the lack of findings in the faster conditions. The subject population studied is a young, healthy, active group of subjects that may be used to navigating college campuses in which walking faster is not out of the ordinary. On the other hand, walking slower may not be something that they encounter on as frequent of a basis, thus explaining why the slower condition elicited changes in coupling, whereas the faster walking conditions did not. There may be a speed that elicits a breakpoint in locomotor respiratory coupling. This concept has been utilized by previous researchers to determine anaerobic threshold while cycling, in which it was confirmed that a point in which locomotor and respiratory rhythms are no longer coupled predicts anaerobic threshold.

Experiment 2: A total of six patients with COPD and 14 healthy age-matched controls were recruited and consented to participate in this study. COPD was determined based on reported previous diagnosis of the disease and confirmed with spirometry testing ratio of forced expiratory volume in one second to forced vital capacity (FEV₁/FVC) of less than 0.7. Spirometry testing was completed without a bronchodilator. Participants were excluded if they had a history of back or lower extremity injury or surgery that affected the subject's mobility or any other process limiting the ability to walk, including neurological disease or impairment.

Data collection procedures were the same as Experiment 1, except for the walking conditions. Both patients with COPD and healthy age-matched controls underwent the selection of their self-selected pace (SELF). The procedure was the same as Experiment 1. Once a subject's comfortable walking speed was chosen, he or she was allowed to rest for a minimum of one minute and then returned to the treadmill to complete four minutes of walking at that chosen speed. No instructions were given regarding breathing for any of the trials. Three-dimensional marker positions and breathing data for four minutes were recorded in a similar fashion to Experiment 1. After completion of the self-selected pace condition, subjects were then asked to walk for four minutes under four more, randomly assigned, conditions. The conditions were +/−10% and +/−20% of their self-selected pace.

Data treatment was the same as from Experiment 1, and the same dependent variables as in Experiment 1 were calculated from each trial. This included the most common frequency ratio, total number of breaths, total number of heel strikes, maximum cross-correlation, cRQA radius, percent recurrence, mean line length, maximum line length, entropy, and percent determinism. The mean for each group and speed was calculated for each dependent variable. A 2×5 repeated measures ANOVA was conducted in SPSS (SPSS 20.0, IBM, Armonk, NY) to determine the effect of group (patients with COPD and healthy age-matched controls) and speed (SELF, −10%, +10%, −20%, +20%) on each dependent variable. Normality was examined for each dependent variable. The Greenhouse-Geisser correction was reported for all analyses that did not meet normality requirements. Tukey's post hoc comparisons were used if a significant main effect of speed was found. In addition, to explore the effect of age and disease on the dependent variables, a 1×3 one-way ANOVA was used to compare healthy young adults (NORM SELF from Experiment 1), older age-matched adults, and patients with COPD during the SELF condition. The significance level was set at p<0.05.

Results of Experiment 2—Patients with COPD versus age-matched controls: A significant main effect of group (F₁,₁₄:5.7, p=0.03) and speed (F₄,₅₆:25.9, p<0.001) was found for the total number of heel strikes (Table 5). This result was anticipated as the walking speed in the patients with COPD was significantly decreased (Table 1). No interaction was found for the number of heel strikes. No main effect of group or speed and no interaction were found for number of breaths and the most common number of heel strikes per breath (Table 5). The most common frequency ratio utilized by both groups was a 2:1 strategy; however, the range of ratios commonly used differed between the two groups. The patients with COPD utilized a 1:1 ratio that was not found to be used commonly by the age-matched controls. The age-matched controls demonstrated a wider range of ratios that they commonly used within the trials.

A main effect of group was found for the maximum cross-correlation value (F₂,₂₅:5.9, p=0.03). The patients with COPD demonstrated a significantly greater maximum cross-correlation value as compared with their age-matched controls (Table 6). Neither a main effect of speed nor an interaction was found for maximum cross-correlation values.

No significant main effect of group, speed, and interaction was found for radius and percent recurrence. This confirms that the parameters used to determine percent determinism, entropy, maximum line length, and mean line length were the same for both groups at all speeds (Table 7). A main effect of group was found for maximum line length (F₂,₂₅: 6.5, p=0.02). Patients with COPD demonstrated a longer maximum line length than did the age-matched controls. Percent determinism, entropy, and mean line lengths did not elicit a main effect of group.

A main effect of speed was found for percent determinism (F₄,₆₀:4.6, p=0.003), entropy (F₄,₆₀:6.5, p=0.002), maximum line length (F₄,₆₀:4.1, p=0.01), and mean line length (F₄,₆₀: 5.4, p=0.01). For percent determinism, −20% was significantly greater as compared with SELF (p=0.009), −10% (p=0.02), +10% (p=0.001), and +20% (p=0.002). Entropy was significantly decreased during +10% speed as compared with SELF (p=0.03) and −20% (p<0.001). The −20% speed elicited significantly increased entropy as compared with −10% and +20% (p=0.03 and p=0.001, respectively). The maximum line length was shorter at +10% as compared with SELF (p=0.04), −10% (p=0.02), and −20% (p=0.02). In addition, the maximum line length at +20% was found to be significantly shorter than at −20% (p=0.02). Similar to the maximum line length, the mean of line lengths was shorter at +10% as compared with SELF, −10%, and −20% (p=0.01 for all three comparisons). In addition, the maximum line length at +20% was found to be significantly shorter than at −20% (p=0.01).

Figure 20:
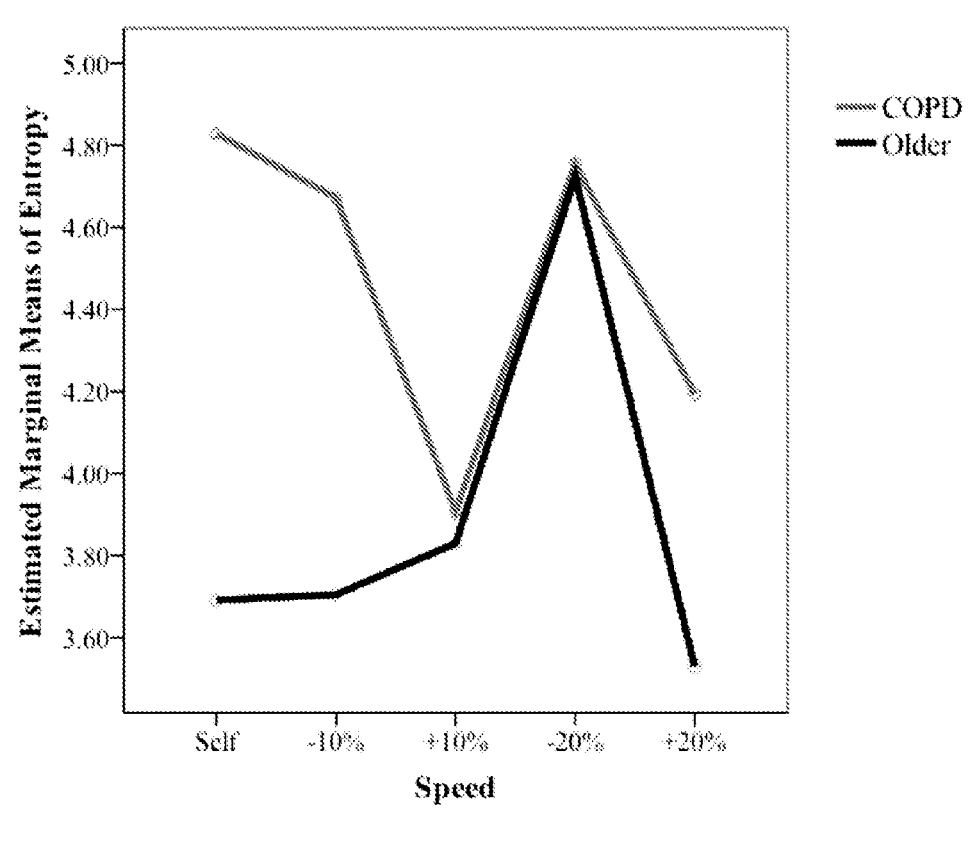
FIG. 20 illustrates the interaction of entropy between the breathing and locomotion time series in patients with COPD compared with the age-matched controls in the COPD severity estimation study.

One significant interaction was found for entropy (F₄,₆₀: 3.2, p=0.04). FIG. 20 illustrates the interaction of entropy between the breath and locomotion (trochanter) time series in patients with COPD compared with the age-matched controls. In FIG. 20, the following symbols represent significant difference from (±) SELF, (#) −10%, (@) +10%, and (^) −20%. The patients with COPD demonstrated decreased entropy at the fastest speeds; whereas the age-matched controls demonstrated lower entropy except at −20% where it was significantly increased, similar to the patients with COPD. No interaction was found for percent determinism, maximum line length, and the mean of line lengths.

Results of Experiment 2—Patients with COPD versus age-matched controls versus young healthy controls: Although 2:1 was the most common ratio used by all three groups, the range of ratios utilized was different between the groups. The patients with COPD were restricted in the ratio that they preferred to use, whereas the age-matched controls used a slightly larger range of ratios. Moreover, the healthy young adults used the widest range of ratios, from 2:1 to 9:1. The most common number of heel strikes in one breath was not significantly different between groups.

The maximum cross-correlation value was not significantly different between groups.

The radius and percent determinism were not significantly different among the three groups. On the other hand, the percent recurrence was significantly greater in the young controls as compared with the older age-matched controls (p=0.02). Entropy, maximum line length, and mean length of lines was significantly increased in the patients with COPD as compared with the older age-matched controls (p=0.02, p=0.009, and p=0.008, respectively).

One purpose of Experiment 2 was to investigate the effect of abnormal breathing rhythms, not under voluntary control, on locomotor respiratory coupling. The results indicate that patients with COPD demonstrate a less variable coupling and simpler frequency ratios as compared with the controls. Not only did patients with COPD demonstrate a 1:1 ratio that was not seen at all in their healthy counterparts, they also demonstrated higher temporal similarity (higher cross-correlation value) and increased strength of coupling (longer cRQA maximum lines), clearly demonstrating a less flexible and adaptable behavior. Furthermore, the effect of speed perturbations was investigated, as patients with COPD and their healthy counterparts were asked to walk at speeds slower and faster than their self-selected walking paces. Although the four cRQA parameters (percent determinism, entropy, maximum line length, and the mean length of lines) had a main effect of speed, of particular interest were the interactions. A significant interaction was found in which patients with COPD demonstrated more patterns in line lengths at the self-selected and slowest speeds (cRQA entropy).

Overall, patients with COPD did demonstrate alterations in their coupling as compared with age-matched controls, supporting the hypothesis that an involuntary, abnormal breathing rhythm can affect locomotor respiratory coupling. Patients with COPD did in fact elicit a more rigid coupling pattern, as indicated by the increased length of the maximum line and a slightly increased temporal relationship as indicated by the maximum cross-correlation. The cross-correlation values themselves demonstrate no relationship in the age-matched controls; however, the patients with COPD demonstrate a weak relationship between the two data sets. This indicates that although weak, there is more of a relationship in the patients with COPD as compared with the controls. Furthermore, based upon the Farey tree representing the hierarchy in the sine circle map, COPD patients demonstrate less flexibility due to their decreased range and simpler (less complex) coupling ratios. This is due to the fact that their most common frequency ratios were between 1:1 and 2:1; only during one speed did a patient with COPD use 3:1 as the most common ratio. A ratio of 1:1 indicates that both walking and breathing coupled together at the exact same frequency, and a ratio of 2:1 indicates that two steps were taken for one breath. This type of simple pattern has been interpreted as a loss of ability to utilize higher order ratios (e.g., 3:1, 3:2, 4:1) due to increases in task difficulty.

Moreover, when patients with COPD were compared with healthy young adults and older age-matched controls while walking at their self-selected speeds, clearer differences between the patients with COPD and their age-matched controls were uncovered. Here, it can be seen that indeed, patients with COPD demonstrate increased patterns in line lengths, increased coupling strength, and coupled locomotor and respiratory rhythms more often. These differences are seen between just the age-matched controls and the patients with COPD (Table 8). Due to the less conservative nature of this statistical test and that fewer comparisons are being tested, it is not surprising that these differences are seen here. Nevertheless, this truly demonstrates that an involuntary, abnormal breathing rhythm does in fact impact how the locomotor and respiratory systems couple.

As stated previously, there are at least two possible physiological mechanisms. One is due to chemoreception of effective oxygen concentration in the lungs, and the other is due to disruptions in neural input and outputs. The design of this study did not allow for investigation into the driving mechanism behind the locomotor respiratory coupling; however, there are a few inferences that can be considered. First, patients with COPD do suffer from dynamic hyperinflation or, simply, air trapping; the pathophysiology of the disease results in less elastic recoil of the lungs during expiration. Therefore, as these patients expire, less air leaves the lungs than what entered the lungs previously. Eventually this leads to a smaller and smaller tidal volume, increases in breathlessness, and worsening ventilation perfusion matching, resulting in hypoxemia that worsens with exercise. A decrease in the effective oxygen concentration in the lungs may with the ability of respiration to synchronize with movement. Second, patients with COPD suffer from abnormal body cell mass alterations, muscular protein degradation leading to muscle wasting/atrophy, impaired energy production and metabolic performance, and increased susceptibility to muscle fatigue and weakness. Furthermore, it appears that afferent sensory loss is present in these patients as well. Consequently, neural-mechanical mechanisms would also be disrupted in patients with COPD.

Alternatively, the mechanism could be unrelated to these physiological explanations. Some dynamic systems theory is based upon behavioral attractors and how preferred (i.e., stable) that attractor is. Preferred performance in certain situations can be along a continuum of very rigid to very random. This has been illustrated as the "depth of the well." If you have a small ball in a shallow well, small perturbations may cause the ball to move out of the well and into another. However, the opposite is true when the well is very deep. Patients with COPD demonstrate a "deep well," corresponding to a very rigid coupling pattern. They prefer a 1:1 or 2:1 coupling that is much tighter than their healthy counterparts, and it is very difficult for them to phase-shift into another behavioral state. Rehabilitation programs, designed from a dynamic systems theory perspective, may use control parameters to try to move the behavioral attractor from one state to another or, as in the previous illustration, from one well to another well. From this perspective, in the current study, speed was applied as a control parameter in an attempt to move subjects from one behavioral attractor to another. If the coupling is so tight that perturbations are not well tolerated, the use of perturbations such as speed is more detrimental than helpful. When the coupling is as tight as it was in the patients with COPD, locomotion may bring about too large of a change in their breathing dynamics, making it too difficult to keep a steady rhythm. This causes them to lock into these 1:1 and 2:1 coupling patterns even more so. Therefore, smaller perturbations at their comfortable walking speed should be considered. For example, giving COPD patients a stimulus to walk with a different pattern could elicit a small enough change in walking dynamics to cause a helpful change in breathing dynamics.

Further differences between the patients with COPD and their age-matched controls can be seen when speed perturbations are introduced. Speed alone elicited changes in cRQA percent determinism, entropy, maximum line length, and mean length of lines, demonstrating that coupling is in fact altered under different task demands. Interestingly, however, the speed that demonstrated the most differences from all the other speeds was the slowest speed, −20%. At −20%, both groups demonstrated an increased number of points being associated with a diagonal line, possibly indicating a more overall periodic movement pattern. The patterns in the lengths of lines were also significantly increased, as well as the length of the longest line and the mean length of lines. The slowest walking speed appears to have caused the patients with COPD to lock into this rigid pattern even more so.

In particular, patients with COPD demonstrated more patterns in line lengths during the self-selected speed and the −10% condition but had similar patterns in line lengths during the +10%, −20%, and +20% conditions (FIG. 20). The representative recurrence plot of the age-matched control (FIG. 18) shows a very distinct pattern in which the peaks of the breathing pattern relate to the valleys of the trochanter movement. This would indicate that breath inspiration was recurrent with the moment right before toe-off. Compared with the representative recurrence plot for the patient with COPD (FIG. 19), the patient with COPD clearly demonstrates longer diagonal lines (more strength in coupling) and without the distinct pattern in which inspiration is clearly recurrent with one portion of the gait cycle. Although the patterns in line lengths are different in the patients with COPD (entropy), the maximum line lengths were significantly longer. Taken together with the rigidity of the frequency ratio, this can been interpreted that the coupling is tighter and this will happen more often than in age-matched controls.

Experiment 2 has demonstrated that an involuntary, abnormal breathing rhythm does have an effect on locomotor respiratory coupling. In addition, speed perturbations can further affect one's ability to couple these two systems. Rehabilitation protocols may focus on techniques that can "push" these patients out of their tight coupling and cause them to explore other, less simple, frequency ratios. This may increase their repertoire of adaptable and flexible behavioral states.

Overall, the two experiments in this study investigated the effect of voluntary and involuntary abnormal breathing rhythms on the ability to couple the locomotor and respiratory systems. In Experiment 1, young healthy controls were asked to walk at a self-selected speed and breathe either at their normal pace, a faster pace, or a slower pace. Even though stepping frequency was constrained to the speed of the treadmill, the healthy young subjects were able to still couple locomotion to the respiratory rhythm. The current results provide further evidence that bidirectionality exists between the two systems and that this could be due to a neural/central command driving mechanism. As brain stem controls to respiration have been clearly identified, it has been shown that signals from the cervical and lumbar limb afferent inputs are conveyed to the brain stem respiratory centers. Further, the mesencephalic locomotor region has been shown to have projections to the respiratory control centers and to locomotor control. In the current study, by voluntarily altering breathing rhythm, the respiratory brain center was able to coordinate this information with the locomotor centers allowing these subjects to still couple under abnormal breathing conditions without any problems.

In addition, Experiment 1 also investigated the effect of mismatching frequencies on coupling. When subjects walked slower and were instructed to breathe slowly, healthy young subjects demonstrated significantly more patterns in line lengths and stronger coupling between the two rhythms, and the average length of time that the two data sets were coupled was longer as compared with when they were asked to walk slower but breathe faster. Subjectively, subjects commented that this mismatched condition was difficult to do and required a lot of concentration. It is possible that instructing subjects to breathe slowly while having them walk faster than their self-selected walking paces was the hardest condition presented to them. Walking slowly may not be a task that these individuals are presented with often, and future studies may want to consider a gradient of speeds to see if there is a speed that elicits a breakpoint in locomotor respiratory coupling.

In Experiment 2, patients with COPD and age-matched controls were tested to investigate the effect of involuntary, abnormal breathing patterns on locomotor respiratory coupling. Patients with COPD demonstrated a strict range of coupling ratios that represented a stabler and simpler coupling, as well as stronger temporal similarity and increased coupling strength. Moreover, when patients with COPD were compared with healthy young adults and older age-matched controls at their self-selected speeds, patients with COPD demonstrated increased patterns in line lengths, a greater coupling strength and couple locomotor, and respiratory rhythms more often as compared with their age-matched controls; hence, a very tight and rigid coupling pattern. Involuntary, abnormal breathing rhythm does in fact impact the ability of the locomotor and respiratory systems to couple. It causes coupling to become very simple, 1:1 as opposed to 3:1 or 4:1, and causes a very rigid behavioral state. From a dynamic systems theory perspective, this preferred performance is very rigid, and rehabilitation programs may be designed to use control parameters to try to move the behavioral attractor from one state to another.

Moreover, in Experiment 2, speed perturbations were introduced and the results confirmed that coupling is in fact altered under altered workloads (e.g., speed). It is interesting to note that the speed changes were elicited mainly at the slowest walking speed. It appears that walking at the slowest speed presented the tightest coupling of all speeds. Furthermore, a significant interaction for entropy was found when patients with COPD demonstrated more patterns in line lengths during differing speeds than their age-matched controls. Demonstrating that at the slower speeds, they were able to increase their ability to couple during different patterns or increase the number of patterns that allowed for entrainment.

Reporting of the most common frequency ratio did not demonstrate any significant changes between any of the groups, conditions, or speeds. The most common frequency ratio was almost always two heel strikes to one breath. This ratio is consistent with published literature. Although the ranges of commonly utilized frequency ratios are reported, this provides very little information about the strength of the coupling and/or how often the coupling is happening. Cross-correlation was also tested, as it has been used previously in locomotor respiratory coupling. However, cross-correlation was not a strong indicator of coupling in the current study. For most conditions, groups, or speeds, the cross-correlation was found to have a weak or no relationship. Although significant, these weak relationships do not add further information to the findings. As cross-correlation is a linear mathematical tool, it may not be able to capture the dynamics of two systems clearly. In addition, cross-correlation looks for the maximum correlation at one time-delayed point. This provides little to no information regarding coupling over time, and/or the strength of coupling over multiple evolutions of the two systems.

The cRQA was the third tool that was developed to quantify coupling in the present study. As cRQA is derived from the analysis of recurrence plots, it inherently is designed to quantify coupling and strength of coupling over time. This allows the user to quantify subtle nonlinear interactions. In the current study, strength of coupling over time, the average lengths of time that locomotion and respiration was coupled and the different complexities of the coupling were revealed. Based upon the findings within these two experiments, it appears that cRQA is an effective tool that can be used to describe locomotor respiratory coupling.

TABLE 1

| | Young Controls N = 12 | Older Controls N = 14 | Patients w/COPD N = 6 | $F_{2.29}$ | p |
|---|---|---|---|---|---|
| | Subject demographics for all subjects in both Experiments 1 and 2. Mean (standard deviation) are reported. | | | | |
| Gender | Males = 12 | Males = 12 | Males = 6 | | |
| Age (years) | 27.33 (5.48) | 66.00 (11.40) * | 63.67 (10.21) # | 61.85 | <0.001 |
| Height (cm) | 183.82 (7.03) | 177.12 (8.52) | 180.36 (8.74) | 2.25 | 0.12 |
| Weight (kg) | 88.10 (13.59) | 80.91 (15.01) | 109.70 (40.13) ^ | 3.90 | 0.03 |
| Preferred gait speed (m/s) | 1.33 (0.20) | 1.17 (0.31) | 0.83 (0.14) # ^ | 8.24 | 0.001 |

(Note:
* indicates significant difference between young and older controls;
# indicates significant difference between young controls and patients with COPD;
^ indicates significant difference between older controls and patients with COPD).

TABLE 2

Comparison of mean(standard deviation) frequency ratios between each of the seven walking conditions.

| Dependent Variable | NORM SELF | SLOW SELF | FAST SELF | SLOW +20% | FAST +20% | SLOW −20% | FAST −20% | $F_{6.54}$ | p |
|---|---|---|---|---|---|---|---|---|---|
| Range of most common frequency ratios | 2:1-5:1 | 2:1-9:1 | 2:1-7:1 | 2:1-6:1 | 2:1-5:1 | 2:1-8:1 | 2:1-4:1 | | |
| Most common frequency ratio/percent occurrence | 2:1/46.1% | 3:1/25.7% | 2:1/32.9% | 3:1/32.0% | 2:1/34.3% | 2:1/31.7% | 2:1/49.2% | | |
| Most common number of heel strikes in one breath | 2.6 (0.52) | 3.9 (2.23) | 3.0 (0.94) | 4.1 (1.37)‡ | 3.0 (1.05) | 3.2 (1.23) | 2.3 (0.67)^ | 2.9 | 0.02 |
| Total number of breaths | 17.4 (3.24) | 11.5 (4.20)‡ | 14.3 (5.70) | 11.5 (3.31)‡@ | 15.3 (5.40) | 12.1 (4.20)‡ | 14.0 (2.71)‡#^ | 3.3 | 0.01 |
| Total number of heel strikes | 45.0 (3.83) | 41.3 (6.68)‡ | 44.3 (5.36) | 44.3 (6.11) | 48.9 (3.25)‡#@^ | 36.6 (7.15)‡#@^† | 40.2 (3.68)‡@^† | 10.1 | <0.001 |

(Note:
The following symbols represent significant difference from
‡SELF,
SLOW SELF,
@FAST SELF,
^SLOW +20%,
†FAST +20%, and
£SLOW −20%.)

TABLE 3

Comparison of mean(standard deviation) cross-correlation (XC)
variables between each of the seven walking conditions.

| Dependent Variable | NORM SELF | SLOW SELF | FAST SELF | SLOW +20% | FAST +20% | SLOW −20% | FAST −20% | $F_{6.54}$ | p |
|---|---|---|---|---|---|---|---|---|---|
| Max XC* | 0.184 (0.074) | 0.161 (0.043) | 0.158 (0.067) | 0.107 (0.036)‡#@ | 0.113 (0.037)‡#@ | 0.160 (0.075) | 0.259 (0.107)#@^†£ | 7.0 | 0.004 |

(Note:
*indicates that the variable did not met the terms of normality and the Greenhouse-Geisser correction is reported.
The following symbols represent significant difference from
‡SELF,
SLOW SELF,
@FAST SELF,
^SLOW +20%,
†FAST +20%, and
£SLOW −20%.)

TABLE 4

Comparison of mean(standard deviation) cRQA variables between each of
the seven walking conditions for the breath and trochanter data sets.

| Dependent Variable | NORM SELF | SLOW SELF | FAST SELF | SLOW +20% | FAST +20% | SLOW –20% | FAST –20% | $F_{6.54}$ | p |
|---|---|---|---|---|---|---|---|---|---|
| Radius* | 14.8 | 14.7 | 15.5 | 14.9 | 15.6 | 14.2 | 16.6 | 0.9 | 0.43 |
| | (3.1) | (3.8) | (2.6) | (3.7) | (3.8) | (3.5) | (3.6) | | |
| % Recurrence | 2.5 | 2.4 | 2.3 | 2.3 | 2.4 | 2.4 | 2.4 | 1.0 | 0.43 |
| | (0.35) | (0.18) | (0.27) | (0.30) | (0.22) | (0.35) | (0.20) | | |
| % Determinism | 87.5 | 88.3 | 85.2 | 86.1 | 82.9 | 91.3 | 88.7 | 2.8 | 0.02 |
| | (5.2) | (5.3) | (6.2) | (7.5) | (9.5) | (3.6)#@† | (5.1)@£ | | |
| Entropy | 4.5 | 4.3 | 4.4 | 4.0 | 4.2 | 4.5 | 4.6 | 2.6 | 0.03 |
| | (0.35) | (0.44) | (0.45) | (0.55)‡@ | (0.62) | (0.64)^ | (0.52)^ | | |
| Max Line | 87.2 | 85.4 | 84.9 | 69.3 | 79.3 | 124.1 | 157.7 | 5.9 | <0.001 |
| | (28.3) | (39.7) | (40.5) | (24.6) | (36.5) | (58.6)^ | (55.9)‡#@^ | | |
| Mean Line | 14.6 | 14.3 | 14.4 | 12.7 | 13.1 | 15.8 | 16.2 | 2.7 | 0.02 |
| | (2.1) | (2.8) | (2.9) | (3.5) | (3.0) | (4.3)^ | (3.7)^ | | |

(Note:
*indicates that the variable did not met the terms of normality and the Greenhouse-Geisser correction is reported.
The following symbols represent significant difference from
‡SELF,
SLOW SELF,
@FAST SELF,
^SLOW +20%,
†FAST +20%, and
£SLOW –20%.)

TABLE 5

Comparison of mean (standard deviation) frequency ratios between patients
with COPD and the age-matched controls for each of the five walking speeds.

| Dependent Variable | | SELF | –10% | +10% | –20% | +20% | Group | | Speed | | Interaction | |
|---|---|---|---|---|---|---|---|---|---|---|---|---|
| | | | | | | | $F_{1.14}$ | p | $F_{4.56}$ | p | $F_{4.56}$ | p |
| Range of most common frequency ratios | Control | 2:1-3:1 | 2:1-6:1 | 2:1-3:1 | 2:1-3:1 | 2:1-3:1 | | | | | | |
| | COPD | 1:1-2:1 | 1:1-2:1 | 2:1 | 1:1-3:1 | 2:1 | | | | | | |
| Most common frequency ratio/percent occurrence | Control | 2:1/59.9% | 2:1/56.6% | 2:1/50.6% | 2:1/66.9% | 2:1/46.8% | | | | | | |
| | COPD | 2:1/56.7% | 2:1/59.4% | 2:1/56.5% | 2:1/46.2% | 2:1/62.4% | | | | | | |
| Most common number of heel strikes in one breath* | Control | 2.1 | 2.2 | 2.2 | 2.0 | 2.3 | 4.0 | 0.07 | 1.7 | 0.20 | 0.27 | 0.81 |
| | | (0.30) | (0.40) | (0.40) | (0.00) | (0.47) | | | | | | |
| | COPD | 1.8 | 1.8 | 2.0 | 1.8 | 2.0 | | | | | | |
| | | (0.45) | (0.45) | (0.00) | (0.45) | (0.00) | | | | | | |
| Total number of breaths | Control | 18.2 | 17.8 | 18.6 | 18.2 | 18.5 | 0.001 | 0.97 | 0.56 | 0.69 | 0.58 | 0.68 |
| | | (3.8) | (3.5) | (3.7) | (3.5) | (4.4) | | | | | | |
| | COPD | 18.4 | 17.4 | 17.0 | 19.2 | 19.0 | | | | | | |
| | | (3.2) | (3.8) | (3.3) | (4.1) | (2.2) | | | | | | |
| Total number of heel strikes | Control | 43.3 | 42.3 | 45.6 | 38.7 | 47.6 | 5.7 | 0.03 | 25.9 | <0.001 | 1.2 | 0.32 |
| | | (4.6) | (4.4) | (4.8)# | (5.2)‡#@ | (5.9)‡#@^ | | | | | | |
| | COPD | 38.8 | 36.2 | 39.0 | 34.6 | 40.8 | | | | | | |
| | | (4.3) | (3.3) | (4.8) | (3.4) | (4.5) | | | | | | |

(Note:

*indicates that the variable did not met the terms of normality and the Greenhouse-Geisser correction is reported.

The following symbols represent significant difference from

‡SELF,

–10%,

@+10%, and

^–20%.)

TABLE 6

Comparison of mean (standard deviation) cross-correlation (XC) between patients
with COPD and the age-matched controls for each of the five walking speeds.

| Dependent Variable | | SELF | −10% | +10% | −20% | +20% | Group $F_{1.15}$ | p | Speed $F_{4.60}$ | p | Interaction $F_{4.60}$ | p |
|---|---|---|---|---|---|---|---|---|---|---|---|---|
| Max XC* | Control | 0.18(0.06) | 0.19(0.11) | 0.15(0.05) | 0.21(0.11) | 0.12(0.06) | 5.9 | 0.03 | 0.22 | 0.85 | 3.1 | 0.05 |
| | COPD | 0.27(0.12) | 0.24(0.10) | 0.26(0.12) | 0.24(0.10) | 0.31(0.17) | | | | | | |

(Note:
*indicates that the variable did not met the terms of normality and the Greenhouse-Geisser correction is reported.
The following symbols represent significant difference from
‡SELF,
−10%,
@+10%, and
^−20%.)

TABLE 7

Comparison of mean (standard deviation) cRQA variables between patients with COPD and the age-
matched controls for each of the five walking speeds for the breath and the trochanter data sets.

| | | SELF | −10% | +10% | −20% | +20% | Group $F_{1.15}$ | p | Speed $F_{4.60}$ | p | Interaction $F_{4.60}$ | p |
|---|---|---|---|---|---|---|---|---|---|---|---|---|
| Radius | Control | 15.9(4.3) | 15.6(3.6) | 17.1(5.4) | 16.6(4.8) | 17.6(4.6) | 0.28 | 0.61 | 0.82 | 0.52 | 0.37 | 0.83 |
| | COPD | 15.3(2.8) | 15.3(2.1) | 17.2(2.8) | 15.5(3.5) | 15.3(2.1) | | | | | | |
| % Recurrence | Control | 2.2(0.15) | 2.4(0.28) | 2.4(0.24) | 2.5(0.29) | 2.4(0.35) | 0.20 | 0.89 | 0.84 | 0.51 | 1.0 | 0.40 |
| | COPD | 2.3(0.24) | 2.4(0.29) | 2.4(0.19) | 2.2(0.10) | 2.5(0.19) | | | | | | |
| % Determinism | Control | 79.4(13.0) | 80.8(13.2) | 81.6(10.1) | 89.8(5.8)‡#@ | 76.4(14.0)^ | 4.4 | 0.05 | 4.6 | 0.003 | 1.5 | 0.21 |
| | COPD | 91.6(4.9) | 91.9(3.8) | 85.9(6.5) | 93.3(3.8) | 87.5(6.3) | | | | | | |
| Entropy* | Control | 3.7(1.0) | 3.7(1.1) | 3.8(0.71)‡ | 4.7(0.68)#@ | 3.5(0.89)^ | 2.8 | 0.11 | 6.5 | 0.002 | 3.2 | 0.04 |
| | COPD | 4.8(0.67) | 4.7(0.53) | 3.9(0.80) | 4.8(0.70) | 4.2(0.89) | | | | | | |
| Max Line | Control | 74.6(39.7) | 78.3(35.8) | 65.7(33.6)‡# | 122.3(71.5)@ | 58.2(22.8)^ | 6.5 | 0.02 | 4.1 | 0.01 | 1.7 | 0.17 |
| | COPD | 129.2(44.0) | 146.0(56.3) | 91.3(38.7) | 127.0(56.6) | 106.8(54.8) | | | | | | |
| Mean Line* | Control | 11.7(3.7) | 12.2(4.6) | 11.8(3.2)‡# | 17.7(8.1)@ | 10.9(3.7)^ | 2.3 | 0.15 | 5.4 | 0.01 | 2.1 | 0.15 |
| | COPD | 17.9(5.4) | 16.2(3.9) | 12.3(2.9) | 17.4(5.0) | 14.1(4.8) | | | | | | |

(Note:
*indicates that the variable did not met the terms of normality and the Greenhouse-Geisser correction is reported.
The following symbols represent significant difference from
‡SELF,
−10%,
@+10%, and
^−20%.)

TABLE 8

Comparison of mean dependent variables between patients
with COPD, older age-matched controls and healthy
young controls at their self-selected speed.

| Dependent Variable | $F_{2.27}$ | p | |
|---|---|---|---|
| Most common number of heel strikes in one breath | 3.3 | 0.05 | |
| Maximum cross-correlation value | 3.4 | 0.05 | |
| cRQA radius | 0.8 | 0.47 | |
| cRQA percent recurrence | 4.4 | 0.02 | * |
| cRQA percent determinism | 3.2 | 0.05 | |
| cRQA entropy | 4.6 | 0.02 | ^ |
| cRQA maximum line length | 5.3 | 0.01 | ^ |
| cRQA mean line length | 5.5 | 0.01 | ^ |

(Note:
* indicates significant difference between young and older age-matched controls;
# indicates significant difference between young controls and patients with COPD;
^ indicates significant difference between age-matched controls and patients with COPD).

Figure 21:
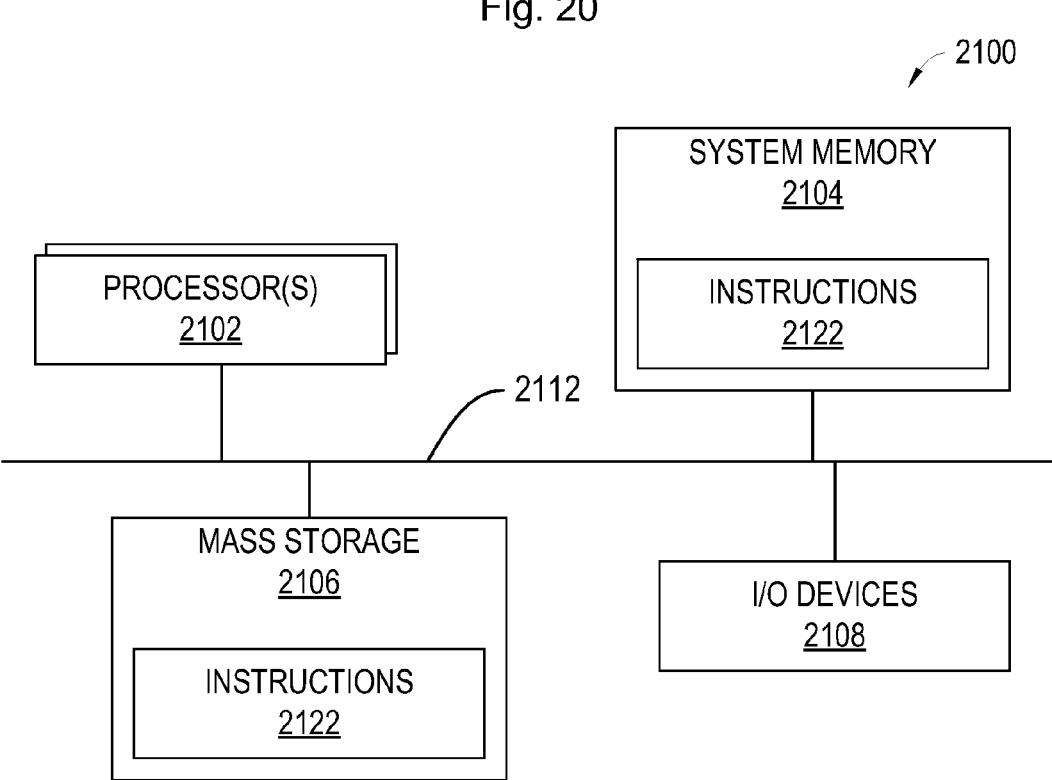
FIG. 21 is a block diagram of an example computing device that may be suitable for use in practicing various ones of the disclosed embodiments.

FIG. 21 is a block diagram of an example computing device 2100 suitable for use in practicing various ones of the disclosed embodiments. As shown, the computing device 2100 may include one or more processors 2102 (e.g., one or more processor cores) and a system memory 2104. For the purpose of this application, including the claims, the terms "processor" and "processor cores" may be considered synonymous, unless the context clearly requires otherwise. As used herein, the term "processor" or "processing device" may refer to any device or portion of a device that processes electronic data from registers and/or memory to transform that electronic data into other electronic data that may be stored in registers and/or memory. The processor(s) 2102 may include one or more microprocessors, graphics processors, digital signal processors, crypto processors, or other suitable devices.

The computing device 2100 may include one or more mass storage devices 2106 (such as diskettes, hard drives, solid-state drives, CD-ROMs, flash memory devices, and so forth). The mass storage device 2106 and/or the system memory 2104 may include any of the embodiments, or portions of the embodiments, of the storage device 206 discussed above with reference to FIG. 2. The system memory 2104 and the mass storage device 2106 may include any suitable storage devices, such as volatile memory (e.g., dynamic random access memory (DRAM)), nonvolatile memory (e.g., read-only memory (ROM), and flash memory. The computing system 2100 may include one or more I/O devices 2108 (such as display, keyboard, cursor control, network interface cards, modems, and so forth). The I/O devices 2108 may include any of the I/O devices 202 discussed above with reference to FIG. 2. The elements may be coupled to each other via a system bus 2112, which represents one or more buses. In the case of multiple buses, they may be bridged by one or more bus bridges (not shown).

Each of these elements may perform its conventional functions known in the art. In particular, the system memory 2104 and the mass storage device 2106 may be employed to store a working copy and a permanent copy of programming instructions implementing any of the methods disclosed herein (e.g., the method of FIG. 11), or portions thereof, herein collectively denoted as instructions 2122. Various methods and system components may be implemented by assembler instructions supported by processor(s) 2102 or high-level languages, such as, for example, C, that can be compiled into such instructions. For example, the computing device 2100 configured with suitable instructions 2122 may provide any suitable ones of the logic components disclosed herein.

The permanent copy of the programming instructions may be placed into permanent mass storage devices 2106 in the factory, or in the field, through, for example, a machine-accessible distribution medium (not shown), such as a compact disc (CD), or through a communication device included in the I/O devices 2108 (e.g., from a distribution server (not shown)). That is, one or more distribution media having an implementation of the agent program may be employed to distribute the agent and program various computing devices. The constitution of elements 2102-2112 are known, and accordingly will not be further described.

Machine-accessible media (including non-transitory computer-readable storage media), methods, systems, and devices for performing the above-described techniques are illustrative examples of embodiments disclosed herein. For example, a computer readable media (e.g., the system memory 2104 and/or the mass storage device 2106) may have stored thereon instructions (e.g., the instructions 2122) such that, when the instructions are executed by one or more processors 2102, the instructions cause the computing device 2100 to perform any of the methods disclosed herein.

In various implementations, the computing device 2100 may be a laptop, a netbook, a notebook, an ultrabook, a smartphone, a tablet, a personal digital assistant (PDA), an ultra mobile PC, a mobile phone, a desktop computer, a server, a printer, a scanner, a monitor, a set-top box, an entertainment control unit, a digital camera, a portable music player, or a digital video recorder. In some implementations, the computing device 2100 may be any other electronic device that processes data. In some embodiments, the COPD severity estimation systems and techniques may be implemented, at least in part, in a high-performance computing device. In some embodiments, the COPD severity estimation systems and techniques described herein may be implemented, at least in part, in handheld computing devices.

The following paragraphs provide examples of various ones of the embodiments disclosed herein.

Example 1 is a system for estimating severity of chronic obstructive pulmonary disease (COPD) in a patient, including: a first logic to receive a breathing signal representative of breathing activity of the patient over a time interval; a second logic to receive a locomotion signal representative of locomotive activity of the patient over the time interval; a third logic to provide breathing data and locomotion data to a fourth logic, wherein: the fourth logic is to generate an estimate of COPD severity in the patient by comparison of 1) a cross-recurrence quantification analysis (cRQA) parameter between the breathing data and the locomotion data and 2) a reference value, the breathing data is based on the breathing signal, and the locomotion data is based on the locomotion signal.

Example 2 may include the subject matter of Example 1, and may further specify that the first logic is to receive the breathing signal from a chest strap sensor coupled to the first logic.

Example 3 may include the subject matter of Example 2, and may further specify that the chest strap sensor is a resistive sensor.

Example 4 may include the subject matter of any of Examples 2-3, and may further specify that the first logic is included in a computing device, and a connector of the chest strap sensor is removably couplable with a connector of the computing device.

Example 5 may include the subject matter of Example 4, and may further specify that the computing device has a housing, and the housing is sized to be received in a pocket of the chest strap sensor.

Example 6 may include the subject matter of any of Examples 1-5, and may further specify that the second logic is included in a computing device having a housing, the second logic is to receive the locomotion signal from an accelerometer coupled to the second logic, and the accelerometer is included in the housing.

Example 7 may include the subject matter of Example 6, and may further specify that the first logic is to receive the breathing signal from a chest strap sensor coupled to the first logic, the first logic is included in the computing device having the housing, and the housing is sized to be received in a pocket of the chest strap sensor.

Example 8 may include the subject matter of any of Examples 1-7, and may further specify that the first logic, the second logic, and the third logic are included in a common housing.

Example 9 may include the subject matter of any of Examples 1-8, and may further include the fourth logic.

Example 10 may include the subject matter of Example 9, and may further specify that the first logic, the second logic, the third logic, and the fourth logic are included in a common housing.

Example 11 may include the subject matter of any of Examples 1-10, and may further specify that the fourth logic is included in a housing of a computing device remote from the third logic.

Example 12 may include the subject matter of Example 11, and may further specify that the third logic is to provide the breathing data and the locomotion data to the fourth logic by providing the breathing data and the locomotion data for storage in a storage device that is accessible to the fourth logic.

Example 13 may include the subject matter of Example 12, and may further specify that the storage device is remote from the third logic and from the fourth logic.

Example 14 may include the subject matter of any of Examples 1-13, and may further specify that the first logic and the second logic are included in a first housing, and the third logic is included in a second housing different from the first housing.

Example 15 may include the subject matter of Example 14, and may further specify that the second housing is a housing of a dock computing device having at least one connector to receive a mating connector of the first housing.

Example 16 may include the subject matter of Example 15, and may further specify that the first housing includes a storage device coupled to the first logic and the second logic, the first logic is to store the breathing data or the breathing signal in the storage device, the second logic is to store the locomotion data or the locomotion signal in the storage device, and the third logic is to read information stored in the storage device when the housing is mated with the dock computing device via the connectors.

Example 17 may include the subject matter of any of Examples 15-16, and may further specify that the dock computing device includes a fifth logic to charge a power supply included in the first housing and coupled to the first and second logic.

Example 18 may include the subject matter of any of Examples 14-17, and may further specify that the first housing includes a storage device coupled to the first logic and the second logic, the first logic is to store the breathing data or the breathing signal in the storage device, the second logic is to store the locomotion data or the locomotion signal in the storage device, and a wireless communication device is included in the first housing to provide information stored in the storage device for access by the third logic.

Example 19 may include the subject matter of any of Examples 14-17, and may further specify that the third logic is included in a smartphone.

Example 20 may include the subject matter of any of Examples 14-19, and may further specify that the second housing includes a wireless communication device to provide the breathing data and the locomotion data wirelessly from the third logic to the fourth logic.

Example 21 may include the subject matter of any of Examples 1-20, and may further specify that the system is to low-pass filter the breathing signal with a cutoff frequency of 0.5 Hz to generate the breathing data.

Example 22 may include the subject matter of Example 21, and may further specify that the first logic is to generate the breathing data by filtration of the breathing signal.

Example 23 may include the subject matter of any of Examples 21-22, and may further specify that the third logic is to generate the breathing data by filtration of the breathing signal.

Example 24 may include the subject matter of any of Examples 1-23, and may further specify that the breathing data is the breathing signal.

Example 25 may include the subject matter of any of Examples 1-24, and may further specify that the system is to low-pass filter the locomotion signal with a cutoff frequency of 10 Hz to generate the locomotion data.

Example 26 may include the subject matter of Example 25, and may further specify that the first logic is to generate the locomotion data by filtration of the locomotion signal.

Example 27 may include the subject matter of any of Examples 25-26, and may further specify that the third logic is to generate the locomotion data by filtration of the breathing signal.

Example 28 may include the subject matter of any of Examples 1-27, and may further specify that the locomotion data is the locomotion signal.

Example 29 may include the subject matter of any of Examples 1-28, and may further specify that the fourth logic is to provide the estimate of COPD severity to a fifth logic, and the fifth logic is to cause the estimate of COPD severity in the patient to be displayed on a display device.

Example 30 may include the subject matter of Example 29, and may further specify that the fifth logic is to cause the estimate of COPD severity in the patient to be displayed on the display device simultaneously with a BODE index for the patient, a GOLD classification for the patient, or an EXACT score for the patient.

Example 31 may include the subject matter of any of Examples 29-30, and may further specify that the fifth logic is to cause the estimate of COPD severity in the patient to be displayed on the display device simultaneously with a GOLD classification for the patient.

Example 32 may include the subject matter of any of Examples 29-31, and may further specify that the fifth logic is to cause the estimate of COPD severity in the patient to be displayed on the display device simultaneously with an EXACT score for the patient.

Example 33 may include the subject matter of any of Examples 1-32, and may further include: a fifth logic to receive a heart rate signal representative of a rate of heartbeats of the patient over the time interval; wherein the third logic is to provide heart rate data, based on the heart rate signal, to a sixth logic, and the sixth logic is to cause the estimate of COPD severity in the patient to be displayed on a display device simultaneously with a heart rate of the patient based on the heart rate data.

Example 34 may include the subject matter of any of Examples 1-33, and may further specify that the time interval is at least 45 seconds.

Example 35 may include the subject matter of any of Examples 1-34, and may further specify that the cRQA parameter between the breathing data and the locomotion data includes a percent determinism.

Example 36 may include the subject matter of Example 35, and may further specify that an increased percent determinism is associated with an estimate of greater severity of COPD.

Example 37 may include the subject matter of any of Examples 1-36, and may further specify that the cRQA parameter between the breathing data and the locomotion data includes a mean diagonal line length.

Example 38 may include the subject matter of Example 37, and may further specify that a diagonal line used in a determination of mean diagonal line length represents at least 100 milliseconds of breathing data and locomotion data.

Example 39 may include the subject matter of any of Examples 37-38, and may further specify that an increased mean diagonal line length is associated with an estimate of greater severity of COPD.

Example 40 may include the subject matter of any of Examples 1-39, and may further specify that the cRQA parameter between the breathing data and the locomotion data includes an entropy.

Example 41 may include the subject matter of Example 40, and may further specify that an increased entropy is associated with an estimate of greater severity of COPD.

Example 42 may include the subject matter of any of Examples 1-41, and may further specify that the cRQA parameter between the breathing data and the locomotion data includes a percent recurrence.

Example 43 may include the subject matter of Example 42, and may further specify that a decreased percent recurrence is associated with an estimate of greater severity of COPD.

Example 44 may include the subject matter of any of Examples 1-43, and may further specify that the fourth logic is to identify a predetermined embedding dimension and to utilize the embedding dimension in a determination of the cRQA parameter.

Example 45 may include the subject matter of any of Examples 1-44, and may further specify that the fourth logic is to identify a predetermined time delay, and to utilize the time delay in a determination of the cRQA parameter.

Example 46 may include the subject matter of any of Examples 1-45, and may further include a fifth logic to generate a prompt to the patient to begin locomotion.

Example 47 may include the subject matter of any of Examples 1-46, and may further specify that a receipt of the locomotion signal by the second logic is initiated by detection of locomotive activity of the patient.

Example 48 may include the subject matter of any of Examples 1-47, and may further specify that the fourth logic is to provide the estimate of COPD severity in the patient to a fifth logic, and the fifth logic is to provide the estimate of COPD severity in the patient to a remote computing device associated with a care provider.

Example 49 may include the subject matter of any of Examples 1-48, and may further specify that the breathing signal is a discrete-time signal having a first sampling rate, the locomotion signal is a discrete-time signal having a second sampling rate different from the first sampling rate, the third logic is to interpolate and resample the breathing signal to the second sampling rate when the first sampling rate is less than the second sampling rate, and the third logic is to interpolate and resample the locomotion signal to the first sampling rate when the second sampling rate is less than the first sampling rate.

Example 50 may include the subject matter of any of Examples 1-49, and may further specify that the reference value is a value of the cRQA parameter from a reference population.

Example 51 may include the subject matter of Example 50, and may further specify that the reference population is a population without COPD.

Example 52 may include the subject matter of any of Examples 1-51, and may further specify that the reference value is a previously obtained value of the cRQA parameter from the patient.

Example 53 may include the subject matter of any of Examples 1-52, and may further specify that the estimate of COPD severity in the patient is an indication that the patient's COPD has increased in severity from a previous time.

Example 54 may include the subject matter of any of Examples 1-53, and may further specify that the estimate of COPD severity in the patient is an indication that the patient's COPD is elevated with respect to a reference population.

Example 55 is a method for estimating severity of chronic obstructive pulmonary disease (COPD) in a patient, including: receiving, by a computing device, breathing data and locomotion data to a fourth logic, wherein the breathing data is representative of breathing activity of the patient over a time interval, and the locomotion data is representative of locomotive activity of the patient over the time interval; generating, by the computing device, an estimate of COPD severity in the patient by comparing 1) a cross-recurrence quantification analysis (cRQA) parameter between the breathing data and the locomotion data and 2) a reference value; and providing, by the computing device, the estimate of COPD severity for display.

Example 56 may include the subject matter of Example 55, and may further specify that the breathing data is generated via use of a chest strap sensor.

Example 57 may include the subject matter of Example 56, and may further specify that the chest strap sensor is a resistive sensor.

Example 58 may include the subject matter of any of Examples 55-57, and may further specify that the locomotion data is generated via use of an accelerometer.

Example 59 may include the subject matter of any of Examples 55-58, and may further specify that the computing device accesses the breathing data and the locomotion data from a storage device remote from the computing device.

Example 60 may include the subject matter of Example 59, wherein the computing device is a first computing device, and the breathing data and the locomotion data are stored in the storage device by a second computing device different from the first computing device.

Example 61 may include the subject matter of Example 60, and may further specify that the second computing device is a dock computing device to receive a wearable computing device including a breathing sensor and a locomotion sensor.

Example 62 may include the subject matter of any of Examples 55-61, and may further include low-pass filtering, by the computing device, the breathing data with a cutoff frequency of 0.5 Hz.

Example 63 may include the subject matter of any of Examples 55-62, and may further include low-pass filtering, by the computing device, the locomotion data with a cutoff frequency of 10 Hz.

Example 64 may include the subject matter of any of Examples 55-63, and may further specify that the display of the estimate of COPD severity in the patient includes a BODE index for the patient, a GOLD classification for the patient, or an EXACT score for the patient.

Example 65 may include the subject matter of any of Examples 55-64, and may further specify that the display of the estimate of COPD severity in the patient includes a GOLD classification for the patient.

Example 66 may include the subject matter of any of Examples 55-65, and may further specify that the display of the estimate of COPD severity in the patient includes an EXACT score for the patient.

Example 67 may include the subject matter of any of Examples 55-66, and may further specify that the display of the estimate of COPD severity in the patient includes a heart rate of the patient.

Example 68 may include the subject matter of any of Examples 55-67, and may further specify that the time interval is at least 45 seconds.

Example 69 may include the subject matter of any of Examples 55-68, and may further specify that the cRQA parameter between the breathing data and the locomotion data includes a percent determinism.

Example 70 may include the subject matter of Example 69, and may further specify that an increased percent determinism is associated with an estimate of greater severity of COPD.

Example 71 may include the subject matter of any of Examples 55-70, and may further specify that the cRQA parameter between the breathing data and the locomotion data includes a mean diagonal line length.

Example 72 may include the subject matter of Example 71, and may further specify that a diagonal line used in the determination of the mean diagonal line length represents at least 100 milliseconds of breathing data and locomotion data.

Example 73 may include the subject matter of any of Examples 71-72, and may further specify that an increased mean diagonal line length is associated with an estimate of greater severity of COPD.

Example 74 may include the subject matter of any of Examples 55-73, and may further specify that the cRQA parameter between the breathing data and the locomotion data includes an entropy.

Example 75 may include the subject matter of Example 74, and may further specify that an increased entropy is associated with an estimate of greater severity of COPD.

Example 76 may include the subject matter of any of Examples 55-75, and may further specify that the cRQA parameter between the breathing data and the locomotion data includes a percent recurrence.

Example 77 may include the subject matter of Example 76, and may further specify that a decreased percent recurrence is associated with an estimate of greater severity of COPD.

Example 78 may include the subject matter of any of Examples 55-77, and may further include identifying, by the computing device, a predetermined embedding dimension, and utilizing, by the computing device, the embedding dimension in the determination of the cRQA parameter.

Example 79 may include the subject matter of any of Examples 55-78, and may further include identifying, by the computing device, a predetermined time delay, and utilizing, by the computing device, the time delay in the determination of the cRQA parameter.

Example 80 may include the subject matter of any of Examples 55-79, and may further specify that the reference value is a value of the cRQA parameter from a reference population.

Example 81 may include the subject matter of Example 80, and may further specify that the reference population is a population age-matched to the patient.

Example 82 may include the subject matter of any of Examples 55-81, and may further specify that the reference value is a previously obtained value of the cRQA parameter from the patient.

Example 83 may include the subject matter of any of Examples 55-82, and may further specify that the estimate of COPD severity in the patient is an indication that the patient's COPD has increased in severity from a previous time.

Example 84 may include the subject matter of any of Examples 55-83, and may further specify that the estimate of COPD severity in the patient is an indication that the patient's COPD is elevated with respect to a reference population.

Example 85 may include the subject matter of any of Examples 55-84, and may further specify that the display of the estimate of COPD severity in the patient includes an indicator of an activity level of the patient.

Example 86 may include the subject matter of any of Examples 1-54, and may further specify that the display of the estimate of COPD severity in the patient includes an indicator of an activity level of the patient.

Example 85 is one or more computer readable media having instructions thereon that, in response to execution by one or more processing devices of a computing device, cause the computing device to perform the method of any of Examples 55-85.

Example 86 is a computing device comprising means for performing the method of any of Examples 55-85.

What is claimed is:

1. A patient monitoring apparatus, comprising a breathing sensor, a locomotion sensor, a display device and at least one processor, said at least one processor configured to:

receive, from the breathing sensor, a breathing signal representative of breathing activity of a patient over a time interval;

receive, from the locomotion sensor, a locomotion signal representative of locomotive activity of the patient over the time interval;

determine whether the received breathing signal and locomotion signal have adequate characteristics for use in generating a Chronic Obstructive Pulmonary Disease (COPD) severity estimate based on the breathing signal and locomotion signal, wherein the display device is configured to display a notification of inadequate characteristics for generating the COPD severity estimate;

when the received breathing signal or locomotion signal are determined as inadequate, then produce an instruction notification to amend a respective error condition; and when the received breathing signal and locomotion signal are determined as adequate, then generate the COPD severity estimate in the patient based on cross-recurrence quantification analysis (cRQA) of the breathing signal and locomotion signal, wherein the display device is configured to display a visual representation of the estimate of COPD severity.

2. The apparatus of claim 1, wherein the at least one processor is further configured to generate the COPD severity estimate by:

producing a vector representation of the locomotion signal and the breathing signal;

applying the cRQA analysis on the vector representation of the locomotion signal and the breathing signal to obtain a cRQA dataset;

calculating at least one cRQA parameter based on the cRQA dataset;

generating the estimate of COPD severity by comparing the cRQA parameter to a reference value; and generating a notification of the COPD severity estimate.

3. The apparatus of claim 2, wherein the at least one processor is further configured to produce the vector representation of the locomotion signal and the breathing signal by:

applying a false-nearest-neighbor algorithm on the locomotion signal and the breathing signal, to determine an embedding dimension of the vector representation of the locomotion signal and the breathing signal;

applying an average mutual information algorithm on the locomotion signal, to determine a time delay representing a spacing between samples of the locomotion signal, to produce the vector representation of the locomotion signal; and applying an average mutual information algorithm on the breathing signal, to determine a time delay representing a spacing between samples of the breathing signal, to produce the vector representation of the breathing signal.

4. The apparatus of claim 2, wherein the at least one processor is further configured to:

calculate a radius, representing minimal distance between the vector representation of the locomotion signal and the breathing signal to be counted as a cRQA point; and perform the cRQA analysis by comparing the vector representation of the breathing signal to the vector representation of the locomotion signal, based on the calculated radius, to generate the cRQA dataset.

5. The apparatus of claim 2, wherein the at least one processor is further configured to display the notification of estimate of COPD severity on a display device, simultaneously with at least one element selected from a list consisting of: a BODE (Body mass, airflow Obstruction, Dyspnea, and Exercise capacity) index for the patient, a GOLD (Global Initiative for Obstructive Lung Disease) classification for the patient, and an EXAcerbations of Chronic pulmonary disease Tool (EXACT) score for the patient.

6. The apparatus of claim 2, wherein the at least one processor is further configured to display the notification of estimate of COPD severity on a display device, simultaneously with an indicator of an activity level of the patient.

7. The apparatus of claim 2, wherein at least one cRQA parameter is a percent determinism parameter, and wherein the at least one processor is configured to calculate the percent determinism parameter value as a percentage of points that fall on a diagonal line within a plot representation of the cRQA dataset.

8. The apparatus of claim 7, wherein the at least one processor is configured to generate the notification of the COPD severity estimate, representing greater severity of COPD, when a value of the percent determinism parameter is increased in relation to the reference value.

9. The apparatus of claim 2, wherein at least one cRQA parameter is a mean diagonal line length, and wherein the at least one processor is configured to calculate a value of the mean diagonal line length as a mean length of a diagonal line length in a plot representation of the cRQA dataset.

10. The apparatus of claim 9, wherein the at least one processor is configured to generate the notification of the COPD severity estimate, representing greater severity of COPD, when a value of the mean diagonal line length is increased in relation to the reference value.

11. The apparatus of claim 2, wherein at least one cRQA parameter is an entropy parameter, and wherein the at least one processor is configured to calculate a value of the entropy parameter as a probability that a length of a diagonal line in a plot representation of the cRQA dataset is repeated.

12. The apparatus of claim 11, wherein the at least one processor is configured to generate the notification of the COPD severity estimate, representing greater severity of COPD, when a value of the entropy parameter is increased in relation to the reference value.

13. The apparatus of claim 2, wherein at least one cRQA parameter is a percent recurrence parameter, and wherein the at least one processor is configured to calculate a value of the percent recurrence parameter as a percentage of an area of a plot representation of the cRQA dataset that is occupied by cRQA points.

14. The apparatus of claim 13, wherein the at least one processor is configured to generate the notification of the COPD severity estimate, representing greater severity of COPD, when a value of the percent recurrence parameter is decreased in relation to the reference value.

15. The apparatus of claim 2, wherein the reference value is a value of the cRQA parameter calculated from a reference population, and wherein the at least one processor is configured to generate the notification of the COPD severity estimate, representing an indication that the patient's COPD severity is elevated with respect to the reference population.

16. The apparatus of claim 2, wherein the reference value is a value of the cRQA parameter obtained from the patient at a previous time, and wherein the at least one processor is configured to generate the notification of the COPD severity estimate, representing an indication that the patient's COPD severity has increased from the previous time.

17. The apparatus of claim 7, wherein the at least one processor is configured to up-convert or down-convert at least one of the locomotion signal and breathing signal, so that the breathing signal and locomotion signal are sampled at consistent times.

18. The apparatus of claim 1, wherein the error condition is selected from a list consisting of: an inadequate number of samples of sufficient locomotive activity have been received; the locomotion sensor being improperly positioned; the locomotion sensor malfunctioning; the locomotion signal being contaminated with noise; an inadequate number of samples of sufficient breathing activity have been received; the breathing sensor being improperly positioned; the breathing sensor malfunctioning; the breathing signal being contaminated with noise, an inadequate walking pace of the patient, and any combination thereof.

19. The apparatus of claim 1, wherein the notification of COPD severity estimate, is selected from a list consisting of an e-mail, a text message, a social media message, a message in a proprietary communication system, and an update of the patient's file in an electronic patient record system maintained by a healthcare facility.

20. The apparatus of claim 1, wherein the locomotion sensor is selected from a list consisting of a one-axis accelerometer, a two-axis accelerometer, a three-axis accelerometer, an Inertial Measurement Unit (IMU) that comprises a gyroscope, an IMU that comprises a three-axis accelerometer, a pressure sensor configured for use inside a patient's shoe or sock to detect steps, one or more wearable image capture devices, and any combination thereof.

21. The apparatus of claim 1, wherein the breathing sensor is selected from a list consisting of a wearable resistive strap, a wearable capacitive strap, a sensor configured to measure flow of air out of a patient's nose and/or mouth, and any combination thereof.

22. A method of estimating COPD severity by at least one processor, the method comprising:

receiving, from a first sensor, a first signal representative of breathing activity of a patient over a time interval;

receive, from a second sensor, a second signal representative of locomotive activity of the patient over the time interval;

producing a vector representation of the first signal and the second signal;

applying a cross-recurrence quantification analysis (cRQA) on the vector representation of the first signal and the second signal to obtain a cRQA dataset;

calculating at least one cRQA parameter value based on the cRQA dataset;

generating an estimation of COPD severity by comparing the cRQA parameter value to a reference value;

generating a notification of the COPD severity estimation; and displaying the notification of the COPD severity estimation on a display device.

* * * * *